US011312753B2

(12) United States Patent
Khlystov et al.

(10) Patent No.: US 11,312,753 B2
(45) Date of Patent: Apr. 26, 2022

(54) METHODS AND SYSTEMS TO PRODUCE LIGNIN-MODIFYING ENZYMES AND USES THEREOF

(71) Applicant: The Board of Trustees of the Leland Stanford Junior University, Stanford, CA (US)

(72) Inventors: Nikita A. Khlystov, Los Altos Hills, CA (US); Elizabeth Sattely, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 16/582,814

(22) Filed: Sep. 25, 2019

(65) Prior Publication Data
US 2020/0095291 A1 Mar. 26, 2020

Related U.S. Application Data

(60) Provisional application No. 62/736,191, filed on Sep. 25, 2018.

(51) Int. Cl.
*C07K 14/375* (2006.01)
*C12N 15/52* (2006.01)
*C12N 15/82* (2006.01)
*C12N 15/81* (2006.01)

(52) U.S. Cl.
CPC .......... *C07K 14/375* (2013.01); *C12N 15/52* (2013.01); *C12N 15/81* (2013.01); *C12N 15/8257* (2013.01); *C07K 2319/02* (2013.01); *C07K 2319/21* (2013.01); *C12Y 101/03007* (2013.01); *C12Y 101/99018* (2013.01); *C12Y 110/03002* (2013.01); *C12Y 111/01013* (2013.01); *C12Y 111/01014* (2013.01); *C12Y 111/01016* (2013.01)

(58) Field of Classification Search
CPC .......... C07K 2319/21; C07K 2319/02; C07K 14/375; C12Y 111/01014; C12Y 111/01013; C12Y 111/01016; C12Y 101/03007; C12Y 101/99018; C12Y 110/03002; C12N 15/81; C12N 9/0065; C12N 15/52; C12N 15/8257; C12N 9/0057; C12N 15/8246; C12N 9/0006
See application file for complete search history.

(56) References Cited

U.S. PATENT DOCUMENTS

| 6,617,435 B2 * | 9/2003 | Turpen | C12N 9/2402 530/427 |
| 10,472,688 B2 * | 11/2019 | Lau | C12Y 102/01 |
| 2012/0079627 A1 * | 3/2012 | Gampala | C12N 15/8216 800/300 |
| 2017/0233753 A1 * | 8/2017 | Parrow | C12N 9/0006 435/99 |

OTHER PUBLICATIONS

Bao et al., Direct over-expression, characterization and H2O2 stability study of active Pleurotus eryngii versatile peroxidase in *Escherichia coli*. Biotechnol Lett., 2012, vol. 34: 1537-1543. (Year: 2012).*
Kinnunen et al., Improved efficiency in screening for lignin-modifying peroxidases and laccases of Basidomycetes. Current Biol., 2017, vol. 6: 105-115. (Year: 2017).*
Martinez et al., Senescence-related changes in the leaf apoplast. J Plant Growth Regul., 2014, vol. 33: 44-45. (Year: 2014).*
Min et al., A dye-decolorizing peroxidase from Bacillus subtilis exhibiting substrate-dependent optimum temperature for dyes and b-ether lignin dimer. Sci. Reports., 2015, vol. 5: 8425, pp. 1-8) (Year: 2015).*
Wen et al., A R2R3-MYB gene LfMYB113 is responsible for autumn leaf coloration in Formosan sweet gum (Liquidamabar formosana Hance). Plant Cell Physiol., 2017, vol. 58(3): 508-521). (Year: 2017).*
Goodin et al., pGD vectors: versatile tools for the expression of green and red fluorescent protein fusions in agroinfiltrated plant leaves. The Plant J., 2002, vol. 31(3): 375-383. (Year: 2002).*
Mnich et al., Degradation of lignin b-aryl ether units in *Arabidopsis thaliana* expressing LigD, LigF and LigG from *Sphingomonas paucimobilis* SYK-6. Plant Biotechnol. J., 2017, vol. 15: 581-593. (Year: 2017).*
Ahmad et al., "Development of novel assays for lignin degradation: comparative analysis of bacterial and fungal lignin degraders", Molecular BioSystems, vol. 6, No. 5, 2010, pp. 815-821, https://doi.org/10.1039/B908966G.
Austin et al., "Production and field performance of transgenic alfalfa (*Medicago sativa* L.) expressing alpha-amylase and manganese-dependent lignin peroxidase", Euphytica, vol. 85, Feb. 1995, pp. 381-393.
Barr et al., "Pyridine Hemochromagen Assay for Determining the Concentration of Heme in Purified Protein Solutions", Bio-Protocol, vol. 5, No. 18, Sep. 20, 2015, pp. 1-7.
Berthet et al., "Disruption of LACCASE4 and 17 Results in Tissue-Specific Alterations to Lignification of *Arabidopsis thaliana* Stems", The Plant Cell, vol. 23, Mar. 2011, pp. 1124-1137.
Chanoca et al., "Lignin Engineering in Forest Trees", Frontiers in Plant Science, vol. 10, No. 912, Jul. 25, 2019, pp. 1-13.

(Continued)

*Primary Examiner* — Ganapathirama Raghu
(74) *Attorney, Agent, or Firm* — KPPB LLP

(57) ABSTRACT

Embodiments of the invention are generally directed to lignin-modifying enzymes and systems and methods of their manufacture. In many embodiments, the lignin-modifying enzymes are lignin-degrading enzymes capable of breaking down lignin into component parts that are usable for other purposes. Several embodiments are directed to systems for producing lignin-modifying enzymes in vivo, including in yeast and/or plant species, and certain embodiments are directed to methods of creating these systems, including transfecting the species to produce lignin-modifying enzymes.

20 Claims, 12 Drawing Sheets
Specification includes a Sequence Listing.

(56) References Cited

OTHER PUBLICATIONS

Clough et al., "Manganese peroxidase from the white-rot fungus Phanerochaete chrysosporium is enzymatically active and accumulates to high levels in transgenic maize seed", Plant Biotechnology Journal, vol. 4, No. 1, Sep. 5, 2005, pp. 53-62.
Conesa et al., "Studies on the Production of Fungal Peroxidases in *Aspergillus niger*", Applied and Environmental Microbiology, vol. 66, No. 7, Jul. 2000, pp. 3016-3023.
Daniel et al., "Pyranose Oxidase, a Major Source of H2O2 during Wood Degradation by Phanerochaete chrysosporium, Trametes versicolor, and Oudemansiella mucida", Applied and Environmental Microbiology, vol. 60, No. 7, Jul. 1994, pp. 2524-2532.
Fernandez-Fueyo et al., "Ligninolytic peroxidase genes in the oyster mushroom genome: heterologous expression, molecular structure, catalytic and stability properties, and lignin-degrading ability", Biotechnology for Biofuels, vol. 7, No. 2, Jan. 3, 2014, pp. 1-23.
Fernandez-Fueyo et al., "Lignin-degrading Peroxidases from Genome of Selective Ligninolytic Fungus *Ceriporiopsis subvermispora*", The Journal of Biological Chemistry, vol. 287, May 11, 2012, First Published: Mar. 21, 2012, pp. 16903-16916, doi: 10.1074/jbc.M112.356378.
Goodin et al., "Nicotiana benthamiana: Its History and Future as a Model for Plant-Pathogen Interactions", Molecular Plant-Microbe Interactions, vol. 21, No. 8, Sep. 2008, pp. 1015-1026.
Guillen et al., "Hydrogen-peroxide-producing system of Pleurotus eryngii involving the extracellular enzyme aryl-alcohol oxidase", Applied Microbiology and Biotechnology, vol. 41, Jun. 1994, pp. 465-470.
Hammel et al., "Ligninolysis by a purified lignin peroxidase", The Journal of Biological Chemistry, vol. 268, Jun. 15, 1993, p. 12274-12281.
Harvey et al., "HEx: A heterologous expression platform for the discovery of fungal natural products", Science Advances, vol. 4, No. 4, eaar5459, Apr. 11, 2018, pp. 1-14.
Hernandez-Ortega et al., "Fungal aryl-alcohol oxidase: a peroxide-producing flavoenzyme involved in lignin degradation", Applied Microbiology and Biotechnology, vol. 93, Jan. 17, 2012, pp. 1395-1410.
Isikgor et al., "Lignocellulosic biomass: a sustainable platform for the production of bio-based chemicals and polymers", Polymer Chemistry, vol. 6, No. 25, May 5, 2015, pp. 4497-4559.
Janusz et al., "Lignin degradation: microorganisms, enzymes involved, genomes analysis and evolution", FEMS Microbiology Reviews, vol. 41, No. 6, Nov. 2017, pp. 941-962.
Kersten, "Glyoxal oxidase of Phanerochaete chrysosporium: Its characterization and activation by lignin peroxidase", PNAS, vol. 87, No. 8, Apr. 1, 1990, pp. 2936-2940.
Kirk et al., "Ligninase of Phanerochaete chrysosporium. Mechanism of its degradation of the non-phenolic arylglycerol β-aryl ether substructure of lignin", Biochemical Journal, vol. 236, No. 1, May 15, 1986, pp. 279-287.
Lambertz et al., "Progress and obstacles in the production and application of recombinant lignin-degrading peroxidases", Bioengineered, vol. 7, No. 3, Jun. 13, 2016, pp. 145-154.
Lau et al., "Six enzymes from mayapple that complete the biosynthetic pathway to the etoposide aglycone", Science, vol. 349, No. 6253, Sep. 11, 2015, pp. 1224-1228.
Ligaba-Osena et al., "Reducing biomass recalcitrance by heterologous expression of a bacterial peroxidase in tobacco (*Nicotiana benthamiana*)", Scientific Reports, vol. 7, No. 17104, Dec. 6, 2017, pp. 1-18.
Lin et al., "Functional Expression of Horseradish Peroxidase in *E. coli* by Directed Evolution", Biotechnology Progress, vol. 15, No. 3, 1999, pp. 467-471.
Lopez et al., "Homologous and Heterologous Expression of Basidiomycete Genes Related to Plant Biomass Degradation", Gene Expression Systems in Fungi: Advancements and Applications, Apr. 5, 2016, pp. 119-160, https://doi.org/10.1007/978-3-319-27951-0_5.
Martinez et al., "Genome sequence of the lignocellulose degrading fungus *Phanerochaete chrysosporium* strain RP78", Nature Biotechnology, vol. 22, No. 6, Jun. 2004, Electronic Publication: May 2, 2004, pp. 695-700.
Martinez et al., "Purification and catalytic properties of two manganese peroxidase isoenzymes from *Pleurotus eryngii*", European Journal of Biochemistry, vol. 237, No. 2, Apr. 1996, pp. 424-432.
Michener et al., "Identification and treatment of heme depletion attributed to overexpression of a lineage of evolved P450 monooxygenases", PNAS, vol. 109, No. 47, Nov. 20, 2012, pp. 19504-19509.
Mnich et al., "Degradation of lignin β-aryl ether units in *Arabidopsis thaliana* expressing LigD, LigF and LigG from *Sphingomonas paucimobilis* SYK-6", Plant Biotechnology Journal, vol. 15, No. 5, May 2017, pp. 581-593.
Morawski et al., "Functional expression of horseradish peroxidase in *Saccharomyces cerevisiae* and *Pichia pastoris*", Protein Engineering, Design and Selection, vol. 13, No. 5, May 2000, pp. 377-384.
O'Leary et al., "The Infiltration-centrifugation Technique for Extraction of Apoplastic Fluid from Plant Leaves Using *Phaseolus vulgaris* as an Example", Journal of Visualized Experiments, vol. 94, No. e52113, Dec. 19, 2014, pp. 1-8.
Ragauskas et al., "Lignin Valorization: Improving Lignin Processing in the Biorefinery", Science, vol. 344, No. 6185, May 16, 2014, pp. 1246843-1-1246843-10.
Rakestraw et al., "Directed evolution of a secretory leader for the improved expression of heterologous proteins and full-length antibodies in *Saccharomyces cerevisiae*", Biotechnology and Bioengineering, vol. 103, No. 6, Apr. 1, 2009, 18 pgs.
Riley et al., "Comparative genomics of biotechnologically important yeasts", PNAS, vol. 113, No. 35, Aug. 30, 2016, pp. 9882-9887, https://doi.org/10.1073/pnas.1603941113.
Riley et al., "Extensive sampling of basidiomycete genomes demonstrates inadequacy of the white-rot/brown-rot paradigm for wood decay fungi", PNAS, vol. 111, No. 27, Jul. 8, 2014, pp. 9923-9928.
Sainsbury et al., "pEAQ: versatile expression vectors for easy and quick transient expression of heterologous proteins in plants", Plant Biotechnology Journal, vol. 7, No. 7, Sep. 2009, pp. 682-693.
Sheen, "Peroxidases in the Genus Nicotiana", Theoretical and Applied Genetics, vol. 40, Jan. 1970, pp. 18-25.
Smith et al., "Multiple Molecular Forms of Peroxidases and Esterases Among Nicotiana Species and Amphiploids", Journal of Heredity, vol. 61, No. 5, Sep. 1970, pp. 203-212.
Sollewijn Gelpke et al., "Homologous Expression of Recombinant Lignin Peroxidase in Phanerochaete chrysosporium", Applied and Environmental Microbiology, vol. 65, No. 4, Apr. 1, 1999, pp. 1670-1674, DOI: 10.1128/AEM.65.4.1670-1674.1999.
Tien et al., "Lignin Peroxidase of Phanerochaete chrysosporium", Methods in Enzymology, vol. 161, 1988, pp. 238-249.
Ulmer et al., "Rapid Degradation of Isolated Lignins by Phanerochaete chrysosporium", Applied and Environmental Microbiology, vol. 45, No. 6, Jun. 1983, pp. 1795-1801.
Vina-Gonzalez et al., "Functional expression of aryl-alcohol oxidase in *Saccharomyces cerevisiae* and *Pichia pastoris* by directed evolution", Biotechnology and Bioengineering, vol. 115, No. 7, Mar. 13, 2018, 24 pgs.
Wariishi et al., "In vitro depolymerization of lignin by manganese peroxidase of Phanerochaete chrysosporium", Biochemical and Biophysical Research Communications, Apr. 15, 1991, vol. 176, No. 1, pp. 269-275, https://doi.org/10.1016/0006-291X(91)90919-X.
Wariishi et al., "Lignin Peroxidase Compound III. Mechanism of Formation and Decomposition", The Journal of Biological Chemistry, vol. 265, No. 4, Feb. 5, 1990, pp. 2070-2077.
Wariishi et al., "Manganese(II) Oxidation by Manganese Peroxidase from the Basidiomycete Phanerochaete chrysosporium. Kinetic Mechanism and Role of Chelators", The Journal of Biological Chemistry, vol. 267, No. 33, Nov. 25, 1992, pp. 23688-23695.

\* cited by examiner

| | Lignin peroxidase (LiP) | Versatile peroxidase (VP) | Manganese peroxidase (MnP) | Laccase (Lac) | Pyranose oxidase (POx) | Cellobiose dehydrogenase (CDH) | Aryl alcohol oxidase (AAO) |
|---|---|---|---|---|---|---|---|
| *B. adusta* | 1/12 | 1/1 | 0/6 | 0/1 | 0/1 | - | 0/1 |
| *C. subvermispora* | 1/2 | - | 7/13 | 1/7 | - | 1/1 | 0/5 |
| *D. squalens* | - | 0/3 | 2/9 | 0/11 | - | 0/1 | 0/9 |
| *P. chrysosporium* | 10/10 | - | 5/5 | - | 0/1 | 1/1 | - |
| *P. eryngii* | - | 2/3 | - | 1/10 | - | - | 1/1 |
| *P. ostreatus* | - | 3/4 | 2/5 | 2/12 | - | 1/1 | 1/6 |
| *P. radiata* | 1/4 | - | 2/6 | 1/5 | 0/1 | 0/1 | 0/4 |
| *T. cinnabarina* | 0/4 | 0/2 | 0/3 | 1/5* | 0/2 | 1/1 | 0/3 |
| *T. hirsuta* | 0/9 | 0/2 | 0/7 | 1/7* | 0/1 | 0/1 | - |
| *T. versicolor* | 3/10 | 1/3 | 3/13 | 4/7 | 1/2 | 1/1 | 0/3 |

FIG. 2

SEQUENCE LISTING

```
<160> NUMBER OF SEQ ID NOS: 83

<210> SEQ ID NO 1
<211> LENGTH: 1095
<212> TYPE: DNA
<213> ORGANISM: Artificial Sequence
<220> FEATURE:
<223> OTHER INFORMATION: Codon Optimized

<400> SEQUENCE: 1
tacccatacg acgttcctga ttacgctgct acctgttcta acggtaagac tgtcggtgac      60
gcttcctgtt gtgcttggtt tgatgttttg gacgacattc aacaaaactt gttccacggt     120
ggtcaatgtg gtgctgaagc tcatgaatct attcgtttgg ttttccacga ctctatcgct     180
atttccccag ctatggaagc tcaaggtaaa ttcggtggtg gtggtgctga tggttcaatt     240
atgatcttcg acgacatcga aaccgctttc catccaaaca ttggtttgga cgaaattgtt     300
aagttgcaaa agccattcgt ccaaaagcac ggtgttactc caggtgactt tattgccttc     360
gctggtagag ttgctttgtc taactgtcca ggtgctccac aaatgaactt cttcaccggt     420
agagctccag ctacccaacc agctcccgac ggtttggtcc cagaaccatt ccacactgtt     480
gaccaaatta tcaacagagt taacgacgct ggtgaatttg acgaattgga attggtttgg     540
atgttgagcg ctcactccgt cgctgctgtt aacgacgtcg acccaaccgt tcaaggtttg     600
ccattcgact ccaccccagg tatcttcgac tcccaattct tcgttgaaac ccaattgaga     660
ggtaccgctt ttccaggttc cggtggtaac caaggtgaag tcgaatcccc attaccaggt     720
gaaattagaa tccaatccga ccacaccatt gctagagatt ctagaactgc ctgtgaatgg     780
caatccttcg ttaacaacca atctaagttg gtcgatgact ttcaattcat tttccttgcc     840
cttactcaac tgggtcagga cccaaacgct atgactgatt gttctgatgt tattccacaa     900
tccaagccaa ttccaggtaa cttgccattc tccttcttcc cagctggtaa gaccatcaag     960
gacgttgaac aagcttgtgc tgaaacccca ttcccaacct taactacctt gccaggtcca    1020
gaaacctccg ttcaaagaat cccaccacca ccaggtgctg aacaaaagtt gatttctgaa    1080
gaggatttgt gataa                                                    1095

<210> SEQ ID NO 2
<211> LENGTH: 1095
<212> TYPE: DNA
<213> ORGANISM: Artificial Sequence
<220> FEATURE:
<223> OTHER INFORMATION: Codon Optimized

<400> SEQUENCE: 2
tacccatacg acgttcctga ttacgctgct acttgttcta acggtgccac cgttggtgac      60
gcctcctgct gtgcttggtt cgacgttttg gacgatattc aacaaaactt gtttcaaggt     120
ggtcaatgtg gtgccgaagc tcacgaatcc atcagattgg ttttccacga tgccattgct     180
atttctccag ctatggaagc tcaaggtaag ttcggtggtg gtggtgctga tggttctatc     240
atgatctttg atgacatcga accaaacttc cacccaaaca tcggttttgga cgaaattatc     300 aacttacaaa agccattcgt tcaaaagcac ggtgtcactc caggtgcctt cattgctttc     360
```

-continued

```
gccggtgctg tcgccttgtc caactgtcca ggcgcccac aaatgaactt ctttactggt      420
agagctccag ccactcaacc agctccagat ggtttggtcc ctgaaccatt ccacaccgtt      480
gaccaaatta tcgccagagt caacgacgcc ggtgaattcg atgaattgga attggtttgg      540
atgttgtctg cccactctgt tgctgccgtt aacgacgtcg accctactgt tcaaggtttg      600
ccatttgatt ctacccctgg tatcttcgac tctcaattct tgtcgaaac tcaattcaga      660 ggtattttgt tcccaggttc cggtggtaac caaggtgaag ttgaatccgg tatggctggt      720
gaaatcagaa ttcaaactga tcacaccttg gccagagatt ctagaaccgc ttgtgaatgg      780
caatctttcg tcaacaacca atccaagctg gttagtgact ccaattcat cttcttggcg      840 ttaactcaat gggtcagga cccaaacgct atgactgatt gttctgacgt tatccctatt      900
tctaagccaa tcccaggtaa cttgcctttc tccttcttcc caccaggtaa gtccatgaag      960
gacgttgaac aagcctgtgc tgaaacccct ttcccatctt tggtcacttt gccaggtcct     1020
gctacctccg ttgctagaat cccaccacca ccaggtgccg aacaaaagtt gatttctgaa     1080
gaggatttgt gataa                                                      1095

<210> SEQ ID NO 3
<211> LENGTH: 1095
<212> TYPE: DNA
<213> ORGANISM: Artificial Sequence
<220> FEATURE:
<223> OTHER INFORMATION: Codon Optimized

<400> SEQUENCE: 3
tacccatacg acgttcctga ttacgctgct acttgttcta acggtaaggt tgttccagct       60
gcctcctgtt gtacctggtt taacgttttg tctgacattc aagaaaactt gttcaacggt      120
ggtcaatgtg gtgctgaggc tcacgaatct atccgtttgg ttttccatga tgctatcgct      180
atctccccag ctatggaacc caagcctcc tctgtcagag gtgctgacgg ttccattatg      240
atcttcgatg aaattgaaac taacttccac ccaaacatcg gtttggatga atcgttaga      300 ttgcaaaagc cattcgttca aaagcatggt gttaccccag tgatttcat tgctttcgct      360 ggtgctgtcg cttttgtcca ctgtccaggt gctccacaaa tgaacttctt cactggtaga      420 gcccagcta ctcaaccagc cccagacggt ttggtgccag aaccattcca ctcagttgac      480
caaatcatcg atagagtttt cgacgccggt gagttcgatg aattggaatt ggtctggatg      540
ttgtccgctc acagcgttgc tgctgctaac gacatcgatc caaacatcca aggtttgcca      600
ttcgattcca ctccaggtat tttcgactcc caattcttcg tcgaaactca attggctggt      660 accggttca ccggtggttc caacaaccaa ggtgaagttt cctctccatt gccaggtgaa      720
atgagattgc aatccgattt cttgatcgct cgtgacgcta gaaccgcttg tgaatggcaa      780
tctttcgtca caaccaatc aaagttggtt ccgatttcc aattcatctt cttggctttg      840
actcaattgg gtcaagaccc tgacgctatg accgattgtt ctgctgttat tccaatctcc      900
aagccagccc ctaacaacac tccaggtttc tccttcttcc caccaggtat gactatggat      960
gacgttgaac aagcttgtgc tgaaacccca ttcccaactt taagcacttt gccaggtcca     1020
gccacctctg ttgctagaat tccaccacca ccaggtgcag aacaaaagtt gatttctgaa     1080
gaggatttgt gataa                                                      1095

<210> SEQ ID NO 4
<211> LENGTH: 1095
<212> TYPE: DNA
```

<213> ORGANISM: Artificial Sequence
<220> FEATURE:
<223> OTHER INFORMATION: Codon Optimized

<400> SEQUENCE: 4

```
tacccatacg acgttcctga ttacgctgtt gcttgtccag acggtgttca caccgcttca    60
aacgctgcct gttgcgcttg gttcccagtt ttggatgaca tccaacaaaa cttgttccac   120
ggtggtcaat gtggtgctga agctcacgaa gctttgagaa tggttttttca tgactccatt   180
gccatttctc caaagttgca atctcaaggt aagttcggtg gtggtggtgc tgatggttcc   240
atcattactt tctcctctat cgaaaccacc taccacccaa acattggttt ggacgaagtc   300
gttgccattc aaaagccatt catcgctaag catggtgtta ctagaggtga cttcatcgcc   360
ttcgctggtg ctgttggtgt ctccaactgt ccaggtgctc acaaatgca attttttcttg   420
ggtagaccag aagctactca agctgctcca gacggtttgg ttccagaacc attccacact   480
attgaccaag tcttggctag aatgttggac gctggtggtt tgacgaaat tgaaactgtt   540
tggttgttgt ctgcccactc catcgctgct gccaacgatg tcgacccaac catttctggt   600
ttaccattcg actccacccc aggtcaattt gactctcaat tcttcgttga aactcaattg   660
agaggtaccg ctttcccagg taagaccggt atccaaggta ctgtcatgtc tccattgaag   720
ggtgaaatga gattgcaaac tgatcactta ttcgccagag actccagaac cgcttgtgaa   780
tggcaatcct ttgtcaacaa ccaaaccaag ttgcaagaag attttcaatt catttttcact   840
gccctatcta ctttgggtca cgacatgaac gctatgaccg actgttctga agttattcca   900
gccccaaagc cagttaactt tggtccatcc ttcttcccag ctggtaagac ccatgctgac   960
attgaacaag cctgtgcctc tactccttc ccaaccttga tcaccgctcc aggtccatcc  1020
gcttctgttg ccagaattcc accaccacca tctccaaacg aacaaaagtt gatttctgaa  1080
gaggatttgt gataa                                                   1095
```

<210> SEQ ID NO 5
<211> LENGTH: 1092
<212> TYPE: DNA
<213> ORGANISM: Artificial Sequence
<220> FEATURE:
<223> OTHER INFORMATION: Codon Optimized

<400> SEQUENCE: 5

```
tacccatacg acgttcctga ttacgctgct acttgtgcca acggtaagac cgttggtgac    60
gcttcttgtt gtgcttggtt cgacgtcttg gatgacatcc aagctaacat gttccacggt   120
ggtcaatgtg gtgccgaagc ccacgaatcc atcagattgg ttttccacga ctccatcgct   180
atctctccag ctatggaagc caagggtaag ttcggtggtg gtggtgccga cggttctatc   240
atgatcttcg atactatcga aaccgctttc cacccaaaca tcggtttgga cgaagttgtc   300
gctatgcaaa agccattcgt tcaaaagcac ggtgttactc caggtgactt cattgctttc   360
gccggtgctg ttgccttgtc aaactgtcca ggtgctccac aaatgaactt cttcactggt   420
agaaagccag ccacccaacc agctccagac ggtttggtcc agaaccatt tcacaccgtc   480
gatcaaatca ttgctagagt taacgacgct ggtgaattcg acgaattgga attggtttgg   540
atgttgtccg cccactctgt tgctgccgtc aacgacgttg acccaaccgt tcaaggtttg   600
ccattcgatt ctactccagg tatcttcgac tctcaattct tcgttgaaac tcaattcaga   660
ggtaccttgt tccaggttc cggtggtaac caaggtgaag tcgaatccgg tatggccggt   720
gaaattagaa tccaaactga tcacaccttg gctagagatt ctagaactgc ttgtgaatgg   780
```

```
caatccttcg ttggtaacca atctaagttg gtcgacgatt tccaattcat cttcttggct        840
ttgactcaat tgggtcaaga tccaaacgct atgactgact gttctgatgt tatcccattg        900
tctaagccaa tcccaggtaa cggtccattc tccttcttcc cacctggtaa gtctcactcc        960
gatattgaac aagcttgtgc cgaaactcca ttcccttcct tggtcacctt gccaggtcca       1020
gctacctctg ttgctagaat cccaccacac aaggctgaac aaaagttgat ttctgaagag       1080
gatttgtgat aa                                                           1092

<210> SEQ ID NO 6
<211> LENGTH: 1092
<212> TYPE: DNA
<213> ORGANISM: Artificial Sequence
<220> FEATURE:
<223> OTHER INFORMATION: Codon Optimized

<400> SEQUENCE: 6
tacccatacg acgttcctga ttacgctgcc acctgttcca acggtgctac cgtcggtgac         60
gcttccagct gtgcttggtt cgatgttttg gacgacattc aacaaaactt atttaacggt        120
gctcaatgtg gtgctgaagc tcacgaatcc attagattgg ttttccacga tgctatcgcc        180
atttctccag ctttggaatc tcaaggtaag tttggtggtg gtggtgccga cggttccatc        240
attttgttcg atgacattga aactaacttc cacccaaaca tcggtttgga tgaaatcgtc        300
aacttgcaaa agccatttat tcaaaagcac ggtgtcaccc aggtgacttc atcgctttc         360 gctggtgctg tcgctatgtc caactgtcca ggtgccccac aaatgaactt ctttaccggt        420
cgtgctccag ccactcaagc tgctccagat ggtttagtcc cagaaccatt ccatactgtc        480
gatcagatca tttctagagt caacgacgct ggtgaattcg acgaattgga attggtttgg        540
atgttgtccg ctcactccgt tgctgccgct aacgacgttg atccaaccat tcaaggtttg        600
gctttcgact ctactccagg tgtattcgac tcccagtttt tgttgaaaac ccaattgcgt        660
ggtactgctt tcccaggttc cggtggtaac caaggggaag ttgaatctcc attgccaggt        720
gaaatgagat tgcaatccga ttcttccatt gccagagatt ctagaaccgc ttgtgaatgg        780
caatccttcg ttaataacca atctaagtta gtctccgatt tccaattcat tttcttggcc        840
ttgacccaat tgggtgaaaa cccagatgct atgaccgatt gttctgacgt catcccaatc        900
tccaagccaa tcccaaacaa cgtccctttc tctttcttcc cagctggtaa gactatggct        960
gatgttgaac aagcctgtgc tgaaactcca tttccaactt tgaccaccct tgccaggtcca      1020 gaaacctccg tccaaagaat tccaccacca ggtgccgaac aaaagttgat ttctgaagag       1080
gatttgtgat aa                                                           1092

<210> SEQ ID NO 7
<211> LENGTH: 1095
<212> TYPE: DNA
<213> ORGANISM: Artificial Sequence
<220> FEATURE:
<223> OTHER INFORMATION: Codon Optimized

<400> SEQUENCE: 7
tacccatacg acgttcctga ttacgctgct acctgttcta acggtgcaac tgtctctgac         60
gcttcctgtt gtgcttggtt cgatgtcttg gacgatatcc aacaaaactt gttccaaggt        120
ggtcaatgtg gtgctgaagc tcatgagtct atcagattgg ttttcacga ctccatcgct         180 atctctccag ctatggaagc tcaaggtaag ttcggggggtg tggtgctga tggttccatc        240
```

```
atcatcttcg acaccatcga aactgctttc cacccaaaca tcggtttgga tgaaatcgtc    300
aacttgcaaa agccattcat cgctaagcat ggtgtcaccc caggtgactt catcgctttt    360
gctggtgctg ttgctttgtc caactgtcca ggttccccac aaatgaactt ctttaccggt    420
agagctcctg ccaccaaggc tgccctgac ggtttggtcc cagaaccatt ccacaccgtt     480
gatcaattga ttgaaagagt caacgacgct ggtcaattcg acgaattaga attggtttgg    540
atgttgtccg ctcattctgt tgctgctgtc aacgacgtcg atccaaccgt ccaaggtttg    600
ccattcgact ccactccagg tattttcgat tctcaatttt tcgtcgaaac ccaattgcgt    660
ggtttgactt tcccaggttc cggtggtaac caaggtgaag ttacctcccc attgccaggt    720
gaaatcagaa tccaaaccga tcacactttg gctcgtgact ccagaaccgc ttgtgaatgg    780
caatctttcg tcgccaacca atccaagctg gtcagtgact ccaattcat tttcttagct     840 ttgacccagt tgggtcaaga cccaaacgct atgaccgact gttccgacgt cattccaatt    900
tccaagccaa tcccaggtaa cttgcctttc tctttcttcc cagctggtaa gaccatgaag    960
gacgtcgaac aagcctgtgc tgaaactcca ttcccatcct tgaccacctt gccaggtcca    1020
gaaacttctg ttcaaagaat cccaccacct ccaggtgcag aacaaaagtt gatttctgaa    1080
gaggatttgt gataa                                                    1095
```

<210> SEQ ID NO 8
<211> LENGTH: 1095
<212> TYPE: DNA
<213> ORGANISM: Artificial Sequence
<220> FEATURE:
<223> OTHER INFORMATION: Codon Optimized

<400> SEQUENCE: 8

```
tacccatacg acgttcctga ttacgctgct acctgttcta acggtgccac cgttggtgac     60
gaatcttcct gcgcttggtt tgatgtttta gatgatatcc aagaaaactt gttccaaggt    120
gctcaatgtg gtgccgaggc tcacgaatcc attagattgg ttttccatga cgctatcgcc    180
atttccccag ctatggaagc ccaaggtcaa ttcggtggtg gtggtgctga tggttctatc    240
attatcttcg acaccattga aaccgccttc cacccaaaca tcggtttgga tgaaattgtt    300
aatttgcaaa agccattcat tgctaagcac ggtgtcaccc caggtgactt cattgctttc    360
gctggtgctg tcgctttgtc aaactgtcca ggtaccccac aaatgaactt cttcactggt    420
agagctccag ctacccaagc cgccccagac ggtttggtcc ctgaaccatt ccacaccgtc    480
gatcagttga tcaacagagt taacgacgct ggtcaattcg acgaattgga attggtctgg    540
atgttgtctg ctcattccgt tgccgctgtc aacgacgttg atccaactat tcaaggtttg    600
gcttttgact ccactcctgg tatcttcgat tctcaattct tcgttgaaac ccaattgaga    660
ggtactgctt tcccaggttc tggtggcaac caaggtgaag ttgaatctcc attgccaggt    720
gaaattagaa tccaaaccga ccacactttg gctagagatc caagaaccgc tgtgaatgg     780 caatccttcg ttgccaacca atctaagtta gttagtgatt ccaattcat cttcttggcc     840 ctaactcaat gggtcaaga cccaaacgct atgaccgatt gttccgatgt tatcccaatc    900
tccaagccaa ttccaggtga cttgccattc tctttcttcc cagctggtaa gaccgccgct    960
gatgtcgaac aagcttgtgc cgaaactcca ttcccatcct tgaccacctt gccaggccca    1020
gaaacttctg ttcaaagaat cccacccccca ccaggtgccg aacaaaagtt gatttctgaa   1080
gaggatttgt gataa                                                    1095
```

<210> SEQ ID NO 9
<211> LENGTH: 1083
<212> TYPE: DNA
<213> ORGANISM: Artificial Sequence
<220> FEATURE:
<223> OTHER INFORMATION: Codon Optimized

<400> SEQUENCE: 9

| | | |
|---|---|---|
| tacccatacg acgttcctga ttacgctgct acttgtgcta acggtgtcac tgttggtgat | 60 |
| gcttcctgtt gcgcctggtt tgatgttttg acgatatcc aagaaaactt gttccacggt | 120 |
| ggtcaatgtg gtgccgaagc tcacgaatcc attagattgg ttttccatga ctccatcgca | 180 |
| atttctccag ctatggaagc ccagggtaag ttcggtggcg gtggtgctga tggttctatt | 240 |
| atgatcttcg acgacatcga aaccgctttc cacccaaata tcggtttgga cgaaattgtc | 300 |
| aagttgcaaa agccattcgt tcaaaagcac aacgtcaccc caggtgattt tatcgctttc | 360 |
| gctggtgctg ttgccttgtc caactgtcca ggtgccccac aaatgaactt cttcactggt | 420 |
| agagctccag ccccagacgg tttggtccca gaaccattcc acaccgtcga tcaaattatc | 480 |
| tctagagtta acgatgctgg tcaattcgat gaattggaat tggtttggat gttatctgct | 540 |
| cactctgttc tgccgttaa cgacgttgac ccaaccgtcc aaggtttgcc attcgattcc | 600 |
| actccaggta ttttcgactc tcaattcttc gttgaaaccc aattgagagg taccgctttt | 660 |
| ccaggttccg gtggcaacca aggtgaagtc gaatccccat gcctggtga attcagaatc | 720 |
| caatcagatc acaccatcgc tagagattct agaaccgctt gtgaatggca atccttcgtc | 780 |
| aacaaccaaa gcaagctggt gagtgacttc caattcatct tcttggcctt gactcaatta | 840 |
| ggtcaagacc caaacgctat gaccgactgt tcagacgtta ttccacaatc taagccaatc | 900 |
| ccagggaatt taccattctc tttttttccca gctggtaaga ccattaacga tgttgaacaa | 960 |
| gcttgtgccg aaaccccatt cccaactttg actaccttgc caggtccaga aacctccgtt | 1020 |
| caaagaatcc caccaccacc aggtgctgaa caaaagttga tttctgaaga ggatttgtga | 1080 |
| taa | 1083 |

<210> SEQ ID NO 10
<211> LENGTH: 1089
<212> TYPE: DNA
<213> ORGANISM: Artificial Sequence
<220> FEATURE:
<223> OTHER INFORMATION: Codon Optimized

<400> SEQUENCE: 10

| | | |
|---|---|---|
| tacccatacg acgttcctga ttacgctgcc acctgttcca acggtaaaac tgtctcttct | 60 |
| gctgcttgtt gtgcttggtt cccaattttg caagacatcc aagaaaactt gtttaacggt | 120 |
| ggtcaatgtg gtgctgaagc tcatgaatcc ttgcgtttgg ttttcacga tgctattgct | 180 |
| atctccccag cattggaagc tcaaggtaag ttcggtggtg gtggtgctga cggttccatc | 240 |
| atggttttcg atactattga aaccaacttc cacccaaaca tcggtttgga cgaaattgtc | 300 |
| cgtctgcaaa aaccattcgt tcaaaagcac ggtgtcactc ctggtgattt catcgctttc | 360 |
| gctggtgctg ttggttttgtc caactgtcca ggtgccccac aaatgaattt cttcttgggt | 420 |
| agacctgctc aactaaggc tgctccagac ggtttggtca ccgaaccatt ccactctgtt | 480 |
| gaccaaattt tggctagaat ggctgacgct ggggaattcg atgaattgga aactgttgg | 540 |
| ttgttgtccg ctcactctgt cgctgctgct aacgatgttg acccaactag aaacggttta | 600 |
| ccattcgact ccaccccagg tatcttcgat acccaattct tcgttaagac tcaattggct | 660 |

| | | |
|---|---|---|
| ggtaccactt tcccaggttc cggtggtaac caaggtgaag ttatgtcccc cttggccggt | 720 | |
| gaaatgcgtt tacaaagtga cttcttgatt gctagagaca ctagaaccgc ttgtgaatgg | 780 | |
| caatcctttg ttaacaacca atctaagttg acttccgatt ccaattcat cttcgctgct | 840 | |
| ttgtctacct tgggtcatga tatgactacc atgaccgatt gttccgacgt tatcccaatt | 900 | |
| tccaagccat tgagaggtga ctctgctaga tttccagctg gtaaatctat gaaggacgtt | 960 | |
| gaacctgctt gtgctgaaac tccattccca actttggcta ctgctccagg tccagccact | 1020 | |
| tccgttgcta gagttccacc accaccaggt gctgaacaaa agttgatttc tgaagaggat | 1080 | |
| ttgtgataa | 1089 | |

<210> SEQ ID NO 11
<211> LENGTH: 1074
<212> TYPE: DNA
<213> ORGANISM: Artificial Sequence
<220> FEATURE:
<223> OTHER INFORMATION: Codon Optimized

<400> SEQUENCE: 11

| | | |
|---|---|---|
| tacccatacg acgttcctga ttacgctgcc acatgtccag atggtactca attgatgaac | 60 | |
| gctgaatgtt gtgctctatt ggctgttcgt gacgactac aaaacaacat gttcaacaac | 120 | |
| gaatgtggtg acgaagccca cgaagctttg agattgactt ccatgacgc cattgctatc | 180 | |
| tccccagcta tggaagctac cggtcaattc ggtggtggtg gtgctgacgg ttctatcatg | 240 | |
| atcttctcag acatcgaaac taagttccac ccaaacatcg gtttggatga agtcgtcgaa | 300 | |
| tccttcagac catttcaaca acgttctggt atgggtgttg ccgacttcat ccaattctcc | 360 | |
| ggtgctgttg gtacttctaa ctgtccaggt gccccaactt gaacgctttt catcggtaga | 420 | |
| aaggacgcta cccaagctgc tccagatggt ttagtcccag aaccattcca tgacgtcaac | 480 | |
| accatttttgg ctagatttaa cgacgctggt gacttcgacg agttagaaac cgtctggttc | 540 | |
| ttaatcgctc actccgtcgc tgctcaaaac gatatcgacc cagctgtctc tcacgctcca | 600 | |
| ttcgattcca ccccatccgt catggacggt caattttttca tcgaaaccca attgcgtggt | 660 | |
| gtcgaattca tcggtagtgg tggtatcgaa ggtgttgctg aatctccagt caagggtgaa | 720 | |
| ttcagattga tgagtgacca acaaatcgct agagataaca gaaccgcttg tgaatggcaa | 780 | |
| tcctttggta ctgaccaagc caagttgcaa accgttttcc aattcatctt cgaagctatg | 840 | |
| ggtcaattgg gtaccgaccc aaccaccttg atcgattgct ctgacgtctt gccagttcca | 900 | |
| ccacctttgt ccactgttcc acacttccca gctggtatca ccattaacga tgttgaacca | 960 | |
| gcttgtgctg aaaccccatt tccaaccttg ccaaccgacc caggtcctgc tactgctgtt | 1020 | |
| gctgccgttc aagagacga acaaaagttg atttctgaag aggatttgtg ataa | 1074 | |

<210> SEQ ID NO 12
<211> LENGTH: 1077
<212> TYPE: DNA
<213> ORGANISM: Artificial Sequence
<220> FEATURE:
<223> OTHER INFORMATION: Codon Optimized

<400> SEQUENCE: 12

| | | |
|---|---|---|
| tacccatacg acgttcctga ttacgctgtc acttgcccag acggttccat gaccgctaac | 60 | |
| gaagcctgtt gtgtcttgtt cccagtcttg gaagatattc aacaaaactt attcgatggt | 120 | |
| ggtttgtgtg gtgaagaagc ccatgaatct ttgagattga cttccacga cgctttcggt | 180 | |
| ttctccccag ccttgcaagc tcaaggtcaa ttcggtggtg gtggtgctga tggttctgtc | 240 | |

```
attgtttttg aagaaactga agctaacttt gctgctaaca tcggtatcga cgaaatcatt    300
aatgcccaaa agccattcat cgctagacac aacattaccc caggtgactt cgtccaattc    360
gccggtgctg tcggtgctgc caattgtcca ggtgctccac aattgcaatt catgttgggt    420
agaccaatgc cagtcgcttc ttctccagat ggtttaatcc ctgaaccatt cgacactgtt    480
gattctatca ttgaaagatt cgccgacgct ggtaacttca ctgaaaccga aattatctgg    540
ttgttgactg ctcactccat tgctgctgct gacgaagttg atccaactat cccaggtact    600
ccattcgact ctaccccagg tatttcgac agccaaatct tcattgaagt ccaattgaga    660
ggtacctctt tcccaggtac tggtggtaac caaggtgaag ttgaatcccc attgagaggt    720
gaattgagat tgcaatctga ctccgaattg gctagagata gccgtactgc ttgtgaatgg    780
caagccttcg tcgacaacgt cccaagaatg caaactttgt tctctgctgc catgtctacc    840
ttggctgtta ttggtcaaga cacttcccaa atggtcgact gttctgatgt tatcccagtc    900
ccaccaccac acaaggtac tgcccatatt ccagctggtg tgtctaacgc tgatattgaa    960
caagcctgtg ctaccgccgc tttcccatct tgccagtcg acccaggtcc agctacttcc   1020
gtcgccccag ttccaccagc agaacaaaag ttgatttctg aagaggattt gtgataa     1077

<210> SEQ ID NO 13
<211> LENGTH: 1077
<212> TYPE: DNA
<213> ORGANISM: Artificial Sequence
<220> FEATURE:
<223> OTHER INFORMATION: Codon Optimized

<400> SEQUENCE: 13
tacccatacg acgttcctga ttacgctgcc acttgtccag acggtaacac cgtcaccaac     60
gaagcctgtt gtttcttgtt cccaatcttg gaagatatcc aagctaacct gttcaacggt    120
ggtgaatgtg gttccgaagc tcacgaatct ttgagattga cttttccatga cgctattggt    180 ttctctccag ctttgaccgc tcaaggtcaa ttcggtggtg gtggtgctga tggttccgtt    240
atcaccttcg cttctatcga aactgcttac gccgctaacg ctggtatcga ggatattgtt    300
gctgaacaag ctcaattcgt cgccaagtac aatgttagtg ctggtgactt tgttcaattc    360
gctggtgctg tcggttttgtc taactgccca ggtgctccac aattggactt cgttatcggt    420
cgtccagctg ctactgctgc ttccccagac ggtttggttc agaaccattc gacaacgtc    480 acctctatct tggctagatt caacgacgct ggtggtttcg acccacaaca cgttgtctgg    540
ttgcttagct cacactccgt cgctgctgct gaattggttg accatccat cccaggcgct    600 ccattcgatt ctaccccagg ttttgttcgac actcaatttt tcattgaaac ccaattgact    660
ggtaccttgt ggccaggtac cgctaacaac caaggtgaag tcgaatcccc attgctaggt    720
gagattcgtt tgcaatcaga cttcttattg gctagagaca acagaaccgc ttgtgaatgg    780
caatcctttg ctaacgactt gtctagacaa caaactttgt tcaaggccgc tatgtccact    840
ttggctacca tcggtcaaga cacctccacc ttgactgatt gttccgacgt tatcccagtt    900
ccagctgctc cagttggtac tccacacttc ccagctggtt tgaccaacgc tgacgttgac    960
caagcctgta ccactgctgc ttttccaacc ttgtccaccg acccaggtcc agctacttcc   1020
gttgctccag tccctactgc agaacaaaag ttgatttctg aagaggattt gtgataa     1077

<210> SEQ ID NO 14
<211> LENGTH: 1089
<212> TYPE: DNA
```

<213> ORGANISM: Artificial Sequence
<220> FEATURE:
<223> OTHER INFORMATION: Codon Optimized

<400> SEQUENCE: 14

| | | | | | | |
|---|---|---|---|---|---|---|
| tacccatacg | acgttcctga | ttacgctgtt | gcttgtccag | acggtaagaa | cactgctacc | 60 |
| aacgctgctt | gttgttcttt | gttcgccgtc | cgtgacgaca | ttcaacaaaa | cttgttccac | 120 |
| ggtgctcaat | gtggtgaaaa | cgctcacgaa | tccttgagaa | ttactttcca | cgatgctatc | 180 |
| tctttctccc | cagctatgga | agctagaggt | caattcggtg | gtggtggtgc | tgacggtagt | 240 |
| attgctatct | ccctgatat | tgaaaccaac | ttccacgcta | acattggttt | ggacgaaatc | 300 |
| gttgccgaac | aagctccaat | tcaagctaga | cataatttgt | cccacgctga | cttcattatg | 360 |
| tttgctggtg | ctttgggtac | tctaactgt | ccaggtgctc | cacgtttgga | tttcttcttg | 420 |
| ggtagaaagg | acgctactag | accagcccct | gatggtttgg | ttccagaacc | attcgatacc | 480 |
| ttggaagatg | tttttgctag | attggctgac | gcttctgctg | gtgaattcga | tgaaatctta | 540 |
| acggtttggt | tattgaccgc | tcacaccatc | gctgctaccg | atcacttgga | ccctactatt | 600 |
| ccaggtaccc | caatggattc | taccccacac | atctgggaca | cccaattctt | catcgaaacc | 660 |
| caattgagag | gtactgcctt | cccaggtacc | ggtggtaacc | acggtgaagt | tatgtcccca | 720 |
| ttgaagggtg | aaattcgttt | gcaaaccgat | cacttattgg | ctcgtgactc | tagaacctct | 780 |
| tgtgaatggc | aatctttcgt | caacaaccaa | caaaaggctc | aagatatgtt | cgcctttgtt | 840 |
| ttccacgatc | tatccatgtt | gggtcaagac | ccagattctt | tgattgactg | ttccgaattg | 900 |
| atcccacagc | cagctccagt | catcggtaag | gctcacttcc | cagctggttt | gaccaacaag | 960 |
| gacattgaac | aagcctgtgc | tgacactcca | ttcccaacct | tgccaaccga | cccaggtcca | 1020 |
| aagaccactg | ttgctgcagt | tccaatcaac | tccgaacaaa | agttgatttc | tgaagaggat | 1080 |
| ttgtgataa | | | | | | 1089 |

<210> SEQ ID NO 15
<211> LENGTH: 1086
<212> TYPE: DNA
<213> ORGANISM: Artificial Sequence
<220> FEATURE:
<223> OTHER INFORMATION: Codon Optimized

<400> SEQUENCE: 15

| | | | | | | |
|---|---|---|---|---|---|---|
| tacccatacg | acgttcctga | ttacgctgtc | gcttgtccag | acggtgttaa | cactgccacc | 60 |
| aacgccgctt | gttgtcaatt | gttcgccgtc | cgtgacgact | tgcaagaaaa | cttgttccac | 120 |
| ggtggtttgt | gtaccgctga | agcccacgaa | tctttgagat | taactttcca | cgatgctatt | 180 |
| gctatctccc | cagccttgga | acaacaaggt | atttttggtg | gtggtggtgc | cgacggttct | 240 |
| atcgctatct | tctccgatat | cgaaaccgcc | ttccatccaa | acattggttt | ggacgaaatc | 300 |
| gttgaattgc | aaaagccatt | catcgctaga | cacaatctat | ctgttgctga | cttcatccaa | 360 |
| ttcgctggtg | ctatcggtgc | ttctaactgt | gccggtgccc | cacaattggc | tgcttttgtc | 420 |
| ggtagagttg | acgccaccca | accagctcca | gatggtttgg | tcccagaacc | attccatact | 480 |
| cctgaccaaa | tcttcgccag | attggctgac | gcttcccaag | gtgaattga | tgaaattttg | 540 |
| accgtttggc | tattggttgc | tcacaccgtt | gccgctgcca | acgacgttga | cccaaccgtc | 600 |
| ccaggttccc | cattgacag | caccccagaa | gtctgggata | tcaattctt | cgttgaagtt | 660 |
| ttattgaacg | gtaccacttt | cccaggtact | ggtgacaacc | aaggtgaagt | cgcttccca | 720 |
| attgccggtg | aattccgttt | gcaatctgac | ttcgctattg | ctagagactc | ccgtagcgcc | 780 |

```
tgtgaatggc aatcctttgt tgataaccaa ccaaaggctc aggctatgtt ccaattcgtt      840
ttccatgact tgtctatttt cggtcaagac attaactcct tggtcgattg tactgaagtc      900
gttccaatcc ctgctccatt gcaaggtgtc actcacttcc cagctggttt gactgttaac      960
gacattgacc aaccatgtgt tgaaacccca ttccctaccc taccaaccga ccctggtcca     1020
gctacctccg ttgctccagt tcctctacca gaacaaaagt tgatttctga gaggatttg     1080 tgataa                                                                1086

<210> SEQ ID NO 16
<211> LENGTH: 1101
<212> TYPE: DNA
<213> ORGANISM: Artificial Sequence
<220> FEATURE:
<223> OTHER INFORMATION: Codon Optimized

<400> SEQUENCE: 16
tacccatacg acgttcctga ttacgctgtt gcctgcccag acggtgtcaa caccgctacc       60
aacgctgctt gttgtcaatt gttcgctgtc agagaagatt gcaacaaaa cttattccac      120 ggtggtttgt gtaccgctga agctcatgaa tctttgagat taactttcca cgacgctatt      180
gccatctccc ctgctttgga agctcaaggt attttcggtg gtggtggtgc cgacggttct      240
atcgctattt cccagaaaat cgaaactaac ttccacccaa acatcggttt agacgaaatt      300
atcgagttgc aaaagccttt catcgctaga cacaacatct ccgttgctga tttcattcaa      360
ttcgccggtg ctatcggtgc tagcaactgt gctggtgctc acaattggc tgctttcgtt      420 ggtagaaagg acgccaccca accagctcca gatggtttag ttccagaacc atttcatacc      480
ccagatcaaa tcttcgacag attggctgat gcttctcaag gtgaattcga cccaattcta      540
accgtttggt tgttgactgc tcacaccgtc gccgctgcta acgacgttga tccaactaag      600
tccggtttgc cattcgactc caccccagaa ttgtgggaca cccaattctt cttggaaacc      660
caattgagag gtacttcttt cccaggttcc ggtggtaacc aaggtgaggt tgaatctcca      720
ttagctggtg aaatgagatt gcaatccgac cacaccatcg ctagagactc tagaactgct      780
tgcgaatggc aatctttcgt cgacaaccaa ccaaaggccc aacaaatgtt ccaattcgtt      840
ttccacgact tgtccatctt cggtcaagat atcaacacct tggttgattg tactgaagtc      900
gttccaattc cagctgaccc acaaggtcat acccacttcc cagccggttt gtccaacgct      960
gatatcgaac aagcttgtgc cgaaaccct ttcccaacct tcccaactga cccaggtcca     1020
aagaccgctg tcgctccagt tccaaagcca ccagctgcta gaaaggaaca aaagttgatt     1080
tctgaagagg atttgtgata a                                              1101

<210> SEQ ID NO 17
<211> LENGTH: 1110
<212> TYPE: DNA
<213> ORGANISM: Artificial Sequence
<220> FEATURE:
<223> OTHER INFORMATION: Codon Optimized

<400> SEQUENCE: 17
tacccatacg acgttcctga ttacgctgtt gcttgtccag acggtaagaa caccgctatt       60
aacgctgcct gttgctcttt gttcaccgct agagatgaca tccaaaagaa catgtttgat      120
ggtggtcaat gtaacgatat cgctcaccaa gctatcagat tgactttcca tgacgctgtc      180
gccttctctc caactttaac tgctcaaggt aagttcggtg taacggggc cgacggttcc      240
```

```
attatgacct tcgataccat tgaaaccaat ttccacccaa acattggttt ggatgaaatt      300
gttaacattg aaaagccatt cgctcaattc cacaacatga ctccaggtga ctttatccac      360
ttcgctggtg cttttggccgt caccaactgt ccaggtgctc aactttaac cttttctatc      420 ggtcgtccac caccagtcgc cgctgcccca gacggtttgg ttccagaacc atttcacact      480
gccgatcaaa tcttcgctag aatgttggat gctctacaat ttgacgaatt ggaaaccgtc      540
tggggtctta tcgctcacac tgtcggtgcc tccaatgatg ttgacccatc cattccaaga      600
accccattcg actctactcc atccattttc gatggccaat tttttattga tacacaattg      660
agaggtgaat tgttcccagg tcaaggtggt tgcaaggtg aagtcgaatc cccattgaag       720
ggtcaaatta gattacaatc tgatcacatt attgctagag actctagatc cgcctgtgaa      780
tggcaatctt tcgctaacga tcatgataag ttgaccaaca gatttcaatt tgtcatcgaa      840
actttggcca tggttggtca agacccaact aatatgatcg actgttccga agtcattccc      900
attccaaagg atttgaccgc tgctcaattg actccaatgt tcccagctgg taagactaac      960
gctgacgttg agcaagcttg tgctgacacc ccattcccat ccttcgccac tagaccaggt     1020
ccagccaccg ctgtcccacc agtcccatct gctaagaccg gtgccccagg ttccgaacaa     1080
aagttgattt ctgaagagga tttgtgataa                                      1110
```

<210> SEQ ID NO 18
<211> LENGTH: 1056
<212> TYPE: DNA
<213> ORGANISM: Artificial Sequence
<220> FEATURE:
<223> OTHER INFORMATION: Codon Optimized

<400> SEQUENCE: 18

```
tacccatacg acgttcctga ttacgctgcc acttgtgctg acggtagaac cactgctaac       60
gctgcctgtt gcgtcttgtt cccaatcttg gatgatattc aagaaaactt gttcgacggt      120
gctcaatgtg gtgaagaagt ccacgaatcc ttgagattga cttccacga cgccatcggt       180 ttctctccaa ccttaggtgg tggtggtgct gatggttcca ttatcgcctt cgatactatc      240
gaaaccaact tccagctaa cgctggtatt gacgaaattg tttcagctca aaagccattc       300
gttgctaagc ataacatttc cgctggtgat ttcatccaat tcgccggtgc tgttggtgtt      360
tccaactgtc ctggtggtgt tagaattcca ttcttcttgg gtagaccaga tgccgttgct      420
gcctccccag atcacttggt cccagaacca ttcgactccg ttgattctat cttggctaga      480
atgtctgacg ccggtttcag cccagtcgag gttgtctggt tattggcttc tcactccatt      540
gctgctgctg ataaggtcga cccatctatt ccaggtactc cattcgatag tactcctggt      600
gttttcgact ctcaattctt catcgaaacc caattaaagg gtagattgtt cccaggtact      660
gctgataaca agggtgaagc tcaatcccca ttgcaaggtg agattcgact tcaaagcgac      720
cacttgttgg ctagagatcc acaaaccgcc tgtgaatggc aatccatggt caacaaccaa      780
ccaaagattc aaaacagatt cgctgctact atgtccaaga tggccttgtt gggtcaagac      840
aagaccaagt taattgattg ctccgatgtt attccaactc caccagcttt ggtcggtgcc      900
gctcacttac cagccggttt cagtttgtcc gacgttgaac aagcttgtgc tgctacccca      960
ttcccagctt taactgctga cccaggtcca gttacttccg ttccaccagt cccaggttct     1020
gaacaaaagt tgatttctga agaggatttg tgataa                               1056
```

<210> SEQ ID NO 19
<211> LENGTH: 1056

```
<212> TYPE: DNA
<213> ORGANISM: Artificial Sequence
<220> FEATURE:
<223> OTHER INFORMATION: Codon Optimized

<400> SEQUENCE: 19
tacccatacg acgttcctga ttacgctgct acttgtgacg atggtagaac cactgccaac      60
gccgcttgtt gtatcttgtt cccaatttta gacgacattc aagaaaacct attcgacggt     120
gctcaatgtg gcgaagaagt ccatgaatct ttgagattga ccttccacga tgctattggt     180
ttcagcccaa ctttgggtgg tggtggtgct gatggttcta tcattgcttt cgacactatc     240
gaaactaact cccagctaa cgccggtatc gatgaaattg tctctgctca aaagccattc      300
gtcgctaagc ataacatctc cgctggtgac ttcatccaat tgctggtgc tgttggtgtc      360
tctaactgtc caggtggtgt cagaatccct tcttcctag gtagaccaga cgctgtcgct     420
gcttctccag accacttagt tccagaacca ttcgactccg tcgactctat tttggctaga    480
atgggtgacg ctggtttctc tccagttgaa gttgtctggt tgttggcttc tcacagtatt    540
gctgctgctg ataaggtcga cccatctatt ccaggtactc cattcgactc taccccaggt    600
gttttcgatt cccaattctt catcgaaact cagttaaagg gtagattgtt cccaggtacc    660
gctgacaaca agggtgaagc tcaatctcct ttacaaggtg aaattagatt gcaatctgat    720
cacttgttgg ctcgtgatcc tcaaactgcc tgtgaatggc aaagcatggt caacaaccaa    780
ccaaaaatcc aaaacagatt cgctgctacc atgtccaaga tggccttgtt gggtcaagac    840
aaaaccaagt tgattgattg ctctgacgtt atcccaactc caccagcttt ggtcggtgca    900
gctcacttgc cagctggttt ctccttgagc gatgttgaac aagcttgtgc tgctacccca    960
ttcccagctt tgactgctga cccaggtcca gtcactagcg ttccaccagt tccaggttcc   1020
gaacaaaagt tgatttctga agaggatttg tgataa                            1056

<210> SEQ ID NO 20
<211> LENGTH: 1056
<212> TYPE: DNA
<213> ORGANISM: Artificial Sequence
<220> FEATURE:
<223> OTHER INFORMATION: Codon Optimized

<400> SEQUENCE: 20
tacccatacg acgttcctga ttacgctgct acttgtgctg acggtcgtac caccgctaac      60
gctgcttgtt gtgtcttgtt cccaattttg gatgacatcc aagaaaactt gttcgatggt     120
gctcaatgtg gtgaagaagt tcatgaatct ttgagattga cctttcacga cgctattggt     180
ttctctccaa ctttgggtgg tggtggtgct gacggttcca tcattacctt cgataccatc     240
gaaaccaact ttcagctaa cgctggtatt gatgaaatcg tttccgccca aaagccattc      300
gttgctaagc acaacatttc tgctggtgac ttcatccaat cgctggtgc tgtcggtgtt     360
tctaactgtc caggtggtgt cagaatccca ttcttcttgg gtagaccaga tgctgttgct    420
gcttctccag accacttggt cccagaacca ttcgatagcg ttgacaccat cttggctaga    480
atgggtgatg ctggtttttc tgctgtcgaa gttgtctggt tgttggcttc tcattccatc    540
gccgccgctg acaaggtcga cccaagcatc ccaggtaccc cattcgactc tactccaggt    600
gtctttgact ctcaattttt catcgaaacc caattgaagg gtagattgtt ccctggtacc    660
ccagataaca agggtgaagt tcaatcccca ttgcaaggtg aaatcagatt gcaatctgac    720
cacttgttgg cccgtgatcc acaaaccgct tgtgaatggc aatctatggt caacaaccaa    780
```

| | |
|---|---|
| ccaaagatcc aaaacagatt tgctggtacc atgtctaaga tggctttgtt gggtcaagat | 840 |
| aaatctaagt tgatcgactg ttccgatatc attccaactc caccagcttt ggtcggtgct | 900 |
| gctcatttgc cagctggttt tctctttatct gacgtcgaac aagcttgtgc tgaaacccca | 960 |
| ttccctgctt tgaccgctga cccaggtcca gttacttctg ttccaccagt cccaggttct | 1020 |
| gaacaaaagt tgatttctga agaggatttg tgataa | 1056 |

<210> SEQ ID NO 21
<211> LENGTH: 1257
<212> TYPE: DNA
<213> ORGANISM: Artificial Sequence
<220> FEATURE:
<223> OTHER INFORMATION: Codon Optimized

<400> SEQUENCE: 21

| | |
|---|---|
| tacccatacg acgttcctga ttacgctgtc acttgtgcca ccggtcaaac taccgctaac | 60 |
| gaagcttgct gtgccttatt cccaattttg gaggatattc aaactaactt gttcgacggt | 120 |
| gctcaatgtg gtgaagaagt ccacgaatct ttgagattga ctttccatga cgctatcgct | 180 |
| ttttccccag ccttgactaa cgctggtcaa ttcggtggtg gtggtgctga cggttccatg | 240 |
| attatcttct ccgatactga accaaacttc acgccaact tgggtatcga cgaaatcgtt | 300 |
| gaagctcaaa agccattcat cgctagacac aacatttctg ccgctgattt catccaattc | 360 |
| gctggtgcta ttggtgtctc caactgtgct ggtgctccaa gattgaactt cttcttgggt | 420 |
| agaccagacg ctacccaaat cccaccagac gggttggtcc agaaccatt cgacagcgtt | 480 |
| gacaagatcc tatctagaat gggtgacgct ggtttcagca ctgtcgaagt cgtttggttg | 540 |
| ttgagttcac acaccatcgc cgctgccgac ttggtcgacc catctattcc aggtactcca | 600 |
| ttcgactcca ctccatctac cttcgactct caattcttct ggaaaccat gttgcaaggt | 660 |
| accgctttcc caggtactcc aggtaaccaa ggtgaagttg aatccccatt ggccggtgaa | 720 |
| atgagattac aatctgactt cttggtctac tctcgttccg cttgtgaatg caatctatg | 780 |
| gtcaacaaca tgccaaaaat ccaaaacaga ttcacccaag tcatgagaaa gttgagcttg | 840 |
| ttgggtcaca atcaagctga tttaatcgac tgctctgacg tcatccctgt tcctaagact | 900 |
| ttgactaagg ccgccacctt ccctgctggt aagtcccaag ccgacgttga aatcgtcgtc | 960 |
| gctgccactc cattccctgc tttggcttcc gacccaggtc cagttactgc tgttccacca | 1020 |
| gtctacgccc ctcacttggc tttgcacttg tttaacaaat tgacttactg tgccgctcgt | 1080 |
| ttgagaaagt gcctagatag aatcttgtgt tccagcttct cctttccatc cgaattctct | 1140 |
| gtccaaccat tatacaagtg taagatctgt tgtatttgtt ccatcccaga atacactgcc | 1200 |
| ttcccatgcg ctagattgcg tgaacaaaag ttgatttctg aagaggattt gtgataa | 1257 |

<210> SEQ ID NO 22
<211> LENGTH: 1056
<212> TYPE: DNA
<213> ORGANISM: Artificial Sequence
<220> FEATURE:
<223> OTHER INFORMATION: Codon Optimized

<400> SEQUENCE: 22

| | |
|---|---|
| tacccatacg acgttcctga ttacgctgct acctgtgccg gtggtcaagt cactgccaac | 60 |
| gctgcctgtt gtgttttgtt ccccatcttg gaagatttgc aacaaaactt attcgacggt | 120 |
| ggtgaatgtg gtgaagaagt ccacgaatct ttgagattaa ccttccacga cgctatcggt | 180 |
| ttctctccaa ccaagggtgg tggtggtgct gacggttccg tcttgacctt ctctgatcca | 240 |

-continued

| | |
|---|---|
| gaagttaact tcccagctaa cttaggtatt gacgaaatcg tcgaagctca aaagccattc | 300 |
| ttggctagac ataacatctc cgctggtgat ttggtccaat cgccggtgc tttaggtgtt | 360 |
| tccaactgtc ctggtgcccc aagaattcca ttcttcttgg gtagaccacc agccaaggcc | 420 |
| gcttctccaa tcggtttggt cccagaacct ttcgacaccg tcaccgacat cttggacaga | 480 |
| atgggtgacg ctggtttcgc tgccgtcgaa gttgtctggt tgttgtcctc tcacactatc | 540 |
| gctgctgccg accacgttga tgaatccatc ccaggtaccc cattcgactc caccccaagc | 600 |
| atcttcgact cccaattttt cattgaaact caattgagag gtacttcctt cccaggttct | 660 |
| ggtggtaacc acggtgaagt cgaatcccca ttggctggtg aaatcagatt gcaatccgat | 720 |
| cacctattgg ctagagactc cagaacctcc tgcgaatggc aatctatggt tgacaacatg | 780 |
| ccaaagattc aaaacagatt tgctgccacc atgttgaaga tgtctttgct tggtcaaaac | 840 |
| caagctgact taattgactg ttctgatgtt atcccaactc caccagcctt ggtcggtaag | 900 |
| gctcatttac cagccggtaa ggtccaatcc gacgttgaac aagcttgcgc caccactcca | 960 |
| ttcccagcta ttgccgctga tccaggtcca gttaccgctg tccctccagt tccaccatcc | 1020 |
| gaacaaaagt tgatttctga agaggatttg tgataa | 1056 |

<210> SEQ ID NO 23
<211> LENGTH: 1071
<212> TYPE: DNA
<213> ORGANISM: Artificial Sequence
<220> FEATURE:
<223> OTHER INFORMATION: Codon Optimized

<400> SEQUENCE: 23

| | |
|---|---|
| tacccatacg acgttcctga ttacgctgct acctgttctg gtggtcaaac cactgccaac | 60 |
| gatgcttgtt gtgtttggtt cgatgtcttg gatgacatcc aatccaactt gttccacggt | 120 |
| ggtgaatgtg gtgaaaacgc ccatgaaagc ttgagattga ttttccacga tgctattgcc | 180 |
| ttctccccag ctctaactgc tgccggtcaa ttcggtggtg gtggtgctga cggttctatc | 240 |
| atggctcaca ccgatgtcga aattcaatac gctgctaaca acggtttgga cgaaattatc | 300 |
| gaagaacaaa gaccattcgc tttgaagcat aacgttctt tcggggattt tattcaattc | 360 |
| gccggtgctg ttggtgtcgc taattgtaac ggtggtccac aaatcggctt cttcgctggt | 420 |
| agatccaacg actctcaacc agctccagat aaattggttc cattgccatc cgattccgtc | 480 |
| actgacattt tagcccgtgt cgccgatgct ggtttcgctc tgtcgaattt ggtctggatg | 540 |
| ttaatttccc acaccgtcgc cgctcaagat aaggtcgatg acagcattcc aggtaccca | 600 |
| ttcgactcta ctccatccga ttttgacgcc caattcttcg ttgaatctat gttgaatggt | 660 |
| actttaactc caggttccgc cttgcacgac ggtgaggtcc aatccccatt gccaggtgaa | 720 |
| ttcagattgc aatccgactt cttaatcggt agagatagca gaacctcctg tgaatggcaa | 780 |
| aagatgattg ctgatagagc caacatgttg caaaaattcg aacaaaccgt cttgaagttg | 840 |
| ttgggttttct ctcaatccgc cttgactgat tgctctgacg ttattccaat tgctaccggt | 900 |
| accgttgccg atccattctt gccagctggt aagactatgg ctgatatcga agccgcttgt | 960 |
| gctgctaccc cattcccaac tttgtccgcc gcttccggtc cagaaccac catcccagct | 1020 |
| gttccattag actccgaaca aaagttgatt tctgaagagg atttgtgata a | 1071 |

<210> SEQ ID NO 24
<211> LENGTH: 1083
<212> TYPE: DNA

<213> ORGANISM: Artificial Sequence
<220> FEATURE:
<223> OTHER INFORMATION: Codon Optimized

<400> SEQUENCE: 24

```
tacccatacg acgttcctga ttacgctgtc gcttgtccag acggtgttaa cactgccacc      60
aacgctgcct gttgtgcttt gttcgctgtc cgtgatgaca ttcaacaaaa cttgttcgat     120
ggtggtgaat gtggtgaaga agttcacgaa tctttgagat tgactttcca cgatgctatc     180
ggtatctctc catccatcgc tgctaccggt aagttcggtg gtggtggtgc cgatggtagc     240
attatgatct cgatgacat cgaaccaaac ttccatgcta acaacggtgt tgacgaaatt     300
atctccgctc aaaagccatt cgtcgctaag cacaacatga ctgccggtga tttcattcaa     360
ttcgccggtg ctgttggtgt ttccaactgt ccaggtgctc acaactatc tttcttctta     420
ggtagaccag ctgccactca accagctcca gacggtctag tcccagaacc attcgattct     480
gttaccgata tcttgaaccg tttcgctgat gccggtggtt tcactactca agaagttgtc     540
tggttgttgg cttctcactc tattgccgct gccgatcatg tcgacccaac catcccaggt     600
tccccattcg attctacccc agaaatcttt gacacccaat tctttgttga actttgttg      660
aagggtacct tgttcccagg tacttccggt aaccaagggg aagtcgaatc cccattggct     720
ggtgaaatca gattacaatc cgatgccgac ttcgctagag attctagaac tgcttgtgaa     780
tggcaatctt tgttaacaa ccaaccaaga atgcaagttt gttcaaggc tgctatgcaa     840
aagttgtcca tcttgggtca cgatttgact caaatgatcg actgctccga cgttatccca     900
gttccaccat ccaccgctgt cagaggttct cacttgccag ctggtaacac tttagacgat     960
atcgaacaag cctgtgcttc cacccccattc ccaactttga ccgccgaccc aggtccagcc    1020
acttctgttg ctccagttcc accatctgaa caaaagttga tttctgaaga ggatttgtga    1080
taa                                                                  1083
```

<210> SEQ ID NO 25
<211> LENGTH: 1134
<212> TYPE: DNA
<213> ORGANISM: Artificial Sequence
<220> FEATURE:
<223> OTHER INFORMATION: Codon Optimized

<400> SEQUENCE: 25

```
tacccatacg acgttcctga ttacgctgct gtctgtccag acggtaccag agtttcccac      60
gctgcttgtt gtgctttcat ccctttggct caagatttgc aagaaaccat tttccaaaac     120
gaatgtggtg aagatgccca tgaagtcatc agattgactt ccacgacgc tatcgccatc     180
tcccgttctc aaggtccaaa ggctggtggt ggtgctgacg gttccatgtt attgttccca     240
accgttgaac caaacttctc cgccaacaac ggtattgacg actccgttaa caacttgatc     300
ccattcatgc aaaagcacaa cactatttct gctgctgatt ggtccaatt tgctggtgct     360
gttgctttgt ccaactgtcc aggtgctcca agattggaat tcttggccgg tcgtccaaac     420
aagactattg ctgctgtcga cggtttgatc ccagaaccac aagattctgt cactaagatt     480
ttacaaagat cgaggatgc tgtggtttc accccattcg aagtcgtcag cttgttggct     540
tctcattctg tcgccgtgc tgacaaggtt gaccaaacca tcgatgctgc tccattcgac     600
tccactccat tcactttcga cacccaagtc ttttttggaag tcttattgaa gggtgtcggt     660
ttcccaggtt ccgctaacaa caccggtgaa gttgcttctc cattgccatt gggttccggt     720
tctgataccg gtgaaatgcg tttgcaatcc gatttcgcct ggctcacga tccaagaacc     780
```

```
gcttgtatct ggcaaggttt cgtcaacgaa caagctttca tggccgcttc ttttcgtgct      840
gctatgtcta agttggctgt tttaggtcac aacagaaact ccttgattga ctgctcagac      900
gtcgtcccag tcccaaagcc agctactggt caaccagcta tgttcccagc ttctaccggt      960
ccacaagatt tggaattgtc ttgtccatcc gaaagattcc aaccttgac cacccaacca     1020 ggtgcttccc aatctttgat cgcccactgt ccagacggtt ctatgtcctg tccaggtgtc     1080
caattcaacg gtccagctga acaaaagttg atttctgaag aggatttgtg ataa           1134
```

<210> SEQ ID NO 26
<211> LENGTH: 1137
<212> TYPE: DNA
<213> ORGANISM: Artificial Sequence
<220> FEATURE:
<223> OTHER INFORMATION: Codon Optimized

<400> SEQUENCE: 26

```
tacccatacg acgttcctga ttacgctgct gtttgtccag acggtactag agtcaccaac       60
gctgcttgct gtgctttcat tccattggcc caagatttgc aagaaacttt gttccaaggt      120
gactgtggtg aggatgctca tgaagttatc cgtttgacct tcacgatgc tattgctatc      180 tctcaatcct tgggtccaca agccggtggt ggtgccgacg gttcgatgtt gcacttccca      240
accatcgaac taacttctc cgccaacaac ggtattgacg attccgtcaa caacttgttg       300
ccattcatgc agaagcacga cactatttcc gctgccgatc ttgtccaatt cgccggtgct      360
gttgccttgt ctaactgtcc aggtgctcca agattggaat tcatggctgg tagaccaaac      420
accaccatcc cagccgtcga aggtttgatt ccagaaccac aagactccgt caccaagatc      480
ttgcaaagat cgaagatgc cggtaacttc tccccattcg aagttgtctc cttgttggct      540
tctcacactg tcgcaagagc tgataaggtt gatgaaacta ttgacgccgc tccattcgat      600
tctaccccat tcacttttga tacccaagtt ttccttggaag tcttgttgaa gggtaccggt      660
ttcccaggtt ccaacaacaa caccggtgaa gtcatgtccc cattgccatt gggttccggt     720
tctgataccg tgaaatgag attgcaatct gacttcgcct tggctagaga tgaaagaacc     780
gcctgtttct ggcaatcctt cgtcaacgaa caagaattca tggctgcttc ttttaaggct      840
gccatggcta agttggctat tttgggtcat tccagatctt ccttgatcga ttgctctgac      900
gttgtcccag tcccaaagcc agccgtcaac agcctgctca cttcccagc taccaaaggt     960 cctaaggatt tggatacctt gacttgtaag gctttgaagt tcccaacctt aacctctgac     1020
ccaggtgcta ccgaaacctt gattccacac tgttctaacg gcggtatgtc ttgtccaggt     1080
gttcaattcg atggtccagc cgaacaaaag ttgatttctg aagaggattt gtgataa       1137
```

<210> SEQ ID NO 27
<211> LENGTH: 1134
<212> TYPE: DNA
<213> ORGANISM: Artificial Sequence
<220> FEATURE:
<223> OTHER INFORMATION: Codon Optimized

<400> SEQUENCE: 27

```
tacccatacg acgttcctga ttacgctgct acttgtccag acggtaccaa ggttaacaac       60
gccgcttgtt gtgccttcat tccattggct caagacttgc aagaaactat cttccaaaat     120
gattgtggtg aagatgccca cgaagtcatt agattgacct ccatgatgc tattgctatt      180 tctcaatcta agggtccctc tgccggtggt ggtgctgacg gttccatgtt gttgttccca      240
```

```
accattgaac caaacttctc tgcaaacaac ggtattgacg attccgtcaa caacttgatc      300
ccattcatgc aaaagcacga cactatttct gctggtgata tcgtccaatt cgctggtgct      360
gtcgccttga ccaactgccc aggtgctcca caattggaat tcttggccgg tcgtccaaac      420
aagactattc cagctatcga tggtttgatt ccagaaccac aagattctgt cacctccatc      480
ttagaacgtt tcaaggatgc cggtaacttc tctccattcg aagtcgtttc tttgttggct      540
tcccattctg tcgccagagc tgacaaagtc gacgaaacca ttgacgccgc tccattcgat      600 actacccat ttgtttttga cactcaaatc ttcttggaag tcttgttgaa gggtgtcggt       660
ttcccaggta ccgctaacaa cactggtgaa gtcgcctccc cattgccatt aacctccggt      720
tccgacactg gtgaattgag attacaatcc gactttgcct ggctagaga tgaaagaact       780 gcctgcattt ggcaaggttt cgtcaacgaa caagccttga tggctgcttc tttcaaggcc      840
gctatggcta agttggccgt tttgggtcac gatagaaaca ccttggtcga ctgctccgat      900
gtcgttccag ctccaaagcc agccgtcaac aaaccagctt ccttcccagc tactaccggt      960
ccacaagact tggaattgtc ctgtaacact aagcctttcc caagtttgtc cgttgatgct     1020
ggtgctcaac aaaccttgat tccacactgt tccgacggtg atatgacctg tcaatccgtc     1080
caattcaacg gtccagctga acaaaagttg atttctgaag aggatttgtg ataa          1134

<210> SEQ ID NO 28
<211> LENGTH: 1134
<212> TYPE: DNA
<213> ORGANISM: Artificial Sequence
<220> FEATURE:
<223> OTHER INFORMATION: Codon Optimized

<400> SEQUENCE: 28
tacccatacg acgttcctga ttacgctgct gtttgcccag acggtaccag agtttccaac       60
gctgcttgtt gtgctttcgt tccattggcc caagacttgc aagaaacttt gtttatgggt      120
gattgtggtg aagatgctca cgaagtcatc agattaactt ccacgacgc tatcgccatt       180 tctcaatctc aaggtccaga agctggtggt ggtgctgacg gttccatgtt gttgtttcca      240
actatcgaac caaacttcga agccaacaac ggtattgacg actctgttaa caacttaatt      300
ccattcatgc aaaaacataa caccatctct gctgccgact tggttcaatt cgctggtgct      360
gttgctttgt ccaactgtcc aggtgcccca agattggaat tcttagctgg tagaccaaac      420
actactatcc cagctgttga aggtttgatt cctgaaccac aagattctgt taccaagatc      480
ttgcaaagat tcgaggacgc cggtaacttc tctccatttg aagttgtttc cttgttggcc      540
tcccactcta tcgctagagc cgacaaggtc gatgaaacta ttgacgccgc tccattcgac      600
tccacccctt tcaccttcga tacccaagtg ttcttagaag ttttgctaaa gggtactggt      660
tttccaggta ccgctaacaa cactggtgaa gtcgcctccc ctttgccatt gggttccggt      720
actgacactg gtgaaatgag attgcaatct gacttcgctt tagctcgtga ttccagaact      780
gcctgtatct ggcaatcttt cgtcaaccaa caagaattca tggccgcctc tttcaaggct      840
gctatgtcca agttggctat tttaggtcat tccagatcta atttgatcga ttgttccgac      900
gttgtcccag ttccaaagcc agctgttaac aagcctgcca ccttcccagc tactaagggt      960
ccacaagact tggaattgac ttgtacttct gaaaagtttc caactttgac cactgaccca     1020
ggtgccaccg aaaccttaat cccacactgc tctaacggtg gtatgtcttg cccagctgtc     1080
caattcgacg gtccagctga acaaaagttg atttctgaag aggatttgtg ataa          1134
```

<210> SEQ ID NO 29
<211> LENGTH: 1125
<212> TYPE: DNA
<213> ORGANISM: Artificial Sequence
<220> FEATURE:
<223> OTHER INFORMATION: Codon Optimized

<400> SEQUENCE: 29

```
tacccatacg acgttcctga ttacgctgcc gtttgtccag acggtacccg tgtctcccac      60
gccgcttgtt gtgctttcat tccattagct caagacttgc aagaaactat cttccaaaat     120
gaatgtggtg aagatgctca tgaagttatc agattgactt tcacgacgc tatcgctatt      180
tccagatctc aaggtccaaa ggctggtggt ggcgctgatg gttctatgtt gttattccca     240
accgtcgaac caaacttctc cgctaacaac ggtatcgacg attccgttaa caacttgatt     300
ccatttatgc aaaaacacaa caccatttcc gctgctgact ggtccaattc gctggtgcc      360
gttgctttgt ccaactgtcc aggtgctcca agattggaat tcttggccgg tagaccaaac     420
aagaccattg ctgctgtcga cggtttgatc ccagaaccac aagattctgt tactaagatt     480
ttgcagcgtt tcgaggatgc tggtggtttc actccattcg aagtcgttag tttgttggct     540
tcccactccg ttgctagagc tgataaggtt gaccaaacca ttgacgctgc tccatttgat     600
tcagtttttt tggaagtctt gttaaagggt gttggtttcc caggttctgc taacaacact     660
ggtgaagtcg cttctccact accattgggc tcaggttccg acaccggtga atgagattg      720
caatccgact tcgctttggc tcacgatcca cgtactgctt gtatttggca aggtttcgtt     780
aacgaacaag ttttatggc tgcctccttt agagctgcca tgtccaagtt agctgttttg      840
ggtcacaaca gaaacagctt gatcgactgt tccgacgttg tcccagtccc aaagccagct     900
actggtcaac cagccatgtt tccagcttcc accggtccac aagatttaga attgtcctgt     960
ccatctgaaa gattcccaac cttaaccacc caattaagat gtactgaagc tggtgcttcc    1020
caatctttga tcgctcattg tccagacggt tccatgtctt gtccaggtgt tcaattcaac    1080
ggtccagccg aacaaaagtt gatttctgaa gaggatttgt gataa                    1125
```

<210> SEQ ID NO 30
<211> LENGTH: 1164
<212> TYPE: DNA
<213> ORGANISM: Artificial Sequence
<220> FEATURE:
<223> OTHER INFORMATION: Codon Optimized

<400> SEQUENCE: 30

```
tacccatacg acgttcctga ttacgctaag accacttgtt ccaacggtgt tgtcgtccca      60
gacgctgtct gttgtgactt cgttcctttg gcctctgctt tgcaatctga agtcttgatg     120
ggtgattgcg gtgaggatgc tcatgaattg gttagattga ttttccacga cgctatcgct     180
attagccaat ccatgggtcc atctgctggt ggcggtgccg atggttcaat gttgattttc     240
ccaaccgttg aaccagcttt tttcccaaac ttgggtattg ctgactctgt taacaaccta     300
attccattct tgtctcaatt cccaaccatc tctgctggtg acttggtcca attcgctggg     360
gctgtcgcta tttccaactg tccaggtgct ccacaattgg aattccttgc tggtagacca     420
aacgctactc tccagctat cgacggtttg atccagaaac acaagacga tgttaccaag      480
attttggcta gattcaagga tgccggtaac ttctccccag ctgaggttgt cgctttgttg     540
gcttcccatt ctatcgctag agctgaccac gttgatccaa ctttggacgc cgctccattc     600
gactctaccc cattcgattt cgatacccaa attttcttgg aagttttgtt gaagggtgtc     660
```

| ggtttcccag gtttagccaa caacactggt gaagttagct ccccattgcc agtcaccgat | 720 |
| ggtaccgatg ttggtgaatt gcgtttgcaa tctgacttcg ctttggctag agatgaaaga | 780 |
| actgcttgtg cttggcaatc cttcgtcaac gaacaagaag ctatggctac cgcttttcaag | 840 |
| aacgctgtta agaagttggc cgttttgggt cacaacagaa acgatttggt tgactgttct | 900 |
| gctgtcgtcc cagttccaaa gccagctacc ggtactccag ctaccttccc tgcttccacc | 960 |
| ggtccacagg atttggaatt gacctgtact accgaaccat ccctacctt gtctactgct | 1020 |
| cctggtgctc aacaaacctt gattccacac tgttctgacg gtaccatgac ttgtaactct | 1080 |
| gtccaattcg atggtccagc taccaacttc ggtggtgccg acgattcaga acaaaagttg | 1140 |
| atttctgaag aggatttgtg ataa | 1164 |

```
<210> SEQ ID NO 31
<211> LENGTH: 1080
<212> TYPE: DNA
<213> ORGANISM: Artificial Sequence
<220> FEATURE:
<223> OTHER INFORMATION: Codon Optimized

<400> SEQUENCE: 31
```

| tacccatacg acgttcctga ttacgctgtc gcttgtccag atggtgtcaa cactgccacc | 60 |
| aacgctgttt gctgttcttt gttcgctgtc agagatttga tccaagacca attgttcgat | 120 |
| ggtggtgaat gtggtgaaga agttcacgaa tccttgagac ttactttcca cgacgccatt | 180 |
| ggtatctctc caaccatcgc ttctactggt gttttcggtg gtggtggtgc tgacggttcc | 240 |
| atcgctattt tcgctgaaat cgaaaccaac ttccacgcca caacggtgt cgatgaaatc | 300 |
| atcggtgaac aagcaccatt catccaaatg accaacatga ctactgctga cttcatccaa | 360 |
| tttgctggtg ctgttggtgt ttctaactgt ccaggtgctc cagccttgcc tgttttcgtt | 420 |
| ggtagaccag acgctactca accagcccct gacaagactg tcccagaacc attcgacacc | 480 |
| gttgactcca tcttggccag attcgctgat gccggtggtt tctcttccgc tgaagtcgtc | 540 |
| gctttgttgg cctctcacac tattgccgct gctgaccacg tcgatccatc tattcctggt | 600 |
| accccattcg acagcacccc agaaatcttc gatactcaat tcttcattga aacccaacta | 660 |
| cgtggtatct tgttcccagg taccggtggt aaccaaggtg aagtcgaatc cccattacac | 720 |
| ggtgaaatta gattgcaatc cgactccgaa ttggctagag attctagaac tgcctgtgaa | 780 |
| tggcaaagct tcgtcaacaa ccaagctaag atccaatccg ccttcaaggc cgctttcaga | 840 |
| aaaatgacta tcttaggtca ctctgaatcc tctttgatcg aatgttctga agtcatccaa | 900 |
| actccaccag ccttggaagg taacgctcac ttgccagccg tcaaactat gaacgacatc | 960 |
| gaacaagcct cgcgactac cccattccca tctttgtccg ctgatccagg cccagctacc | 1020 |
| tctgtcgccc ctgtcccacc atctgaacaa aagttgattt ctgaagagga tttgtgataa | 1080 |

```
<210> SEQ ID NO 32
<211> LENGTH: 1155
<212> TYPE: DNA
<213> ORGANISM: Artificial Sequence
<220> FEATURE:
<223> OTHER INFORMATION: Codon Optimized

<400> SEQUENCE: 32
```

| tacccatacg acgttcctga ttacgctgtc acctgttccg acggtaccgt cgtccctgac | 60 |
| tctatgtgtt gtgacttcat tccattggcc caagacttgc aatccatggt cttgcaaaac | 120 |
| gaatgtggtg aagatgctca cgaaatcatc agattgactt ccacgacgc catcgctatc | 180 |

```
tctcaatcct tgcctccatc cgccggtact ggtgctgatg gttccatgtt gttgttccct      240
ttggtcgaac cagaattcca agcctctaac ggtatcgacg attctgttaa caacttgatc      300
ccattcttgt ccagccaccc aaacattact gctggtgact tggtccaatt cgctggtgct      360
gttgccttga ctaactgtcc aggtgctcca agagaattgt tggctggtag aaagaatgct      420
gtcgctccag ctatcgacgg tttgattcct gttccacaag ataatgttag tactatccta      480
gctagattcg ctgacgccgg taacttttct ccattcgaag ttgtctcctt gttggcctct      540
cactctgtcg ctagagccga taaggttgac ccaactttgg acgctgcccc atttgatact      600
actccattta ctttcgacac ccaaatcttt ttggaagtct tgttgaaggg tgttggtttt      660
ccaggtttgg acaacaacac cggtgaagtc gcctccccat tgcccttcgg tgacacttcc      720
accggtggta cgacactgg tatgatgaga ttgcaatccg actttgcttt ggctagagat       780
gaacgtaccg cttgtttctg caaggtttc gtcgaccaac aagacttcat ggctcaatct       840
ttccaagctg ctttcgaaaa gatggccatc ttaggttcca acgctgccga tttgatcaac      900
tgttctgctg tcgttccaca atctgtcggt ccagttactg ttccagctac tttcccagct      960
accactggtc cccaagactt acaattgaat tgtacctccg aaaccttccc atctttgtcc     1020
attgacccag gtgctaccga aactttgatt ccacactgtc cagatggtac tgaagattgt     1080
ccatccttgc aattctctgg tcctgccact gactctccag aacaaaagtt gatttctgaa     1140
gaggatttgt gataa                                                      1155

<210> SEQ ID NO 33
<211> LENGTH: 1161
<212> TYPE: DNA
<213> ORGANISM: Artificial Sequence
<220> FEATURE:
<223> OTHER INFORMATION: Codon Optimized

<400> SEQUENCE: 33
tacccatacg acgttcctga ttacgctacc atttgtccag atggtactag agtctccaac        60
cacgtttgtt gtgatttcat cccattggct caagccttac aatccacttt gtacatgggt       120
gactgtggtg aggatgccca tgaaactatt agattgactt ccacgacgc catcgctatt        180 tctcaatccc aaggtccatc tgctggtggt ggtgctgatg gttccatgtt catttttcca       240
actgtcgaac cattcttcca cgctaacgca ggtattgatg actccgtcaa caacttgatt       300
ccattcttgt ctaagttccc aaccattacc gctggtgact taatccaatt cgctggtact      360
gtcgctttgt ctaattgtcc aggtgctcca caattggaat tttggctgg tagacctaac       420 gccaccgctc ctgccgttga cggtttgatt ccagaaccac aagacaacgt tactcatatc      480
ttggaaagat cgctgatgc tggtggtttc actccattcg aagtcgtttc tttgttggct       540
tctcacaccg tcgctagagc tgacaaggtc gacttgacca ttgatgctgc tccattcgac      600
tccactccat tcaccttcga cactcaaatc ttcctagaag ttttgttgaa gggtgtcggt      660
ttcccaggta ccgacaacaa cactggtgaa gttgaatctc cattgccatt gggtaacaac      720
aagcaaggtg gtaacgacac cggtgaaatg agattgcaat ctgacttcgc tttggcccgt     780
gacgacagaa ccgcatgttt ctggcaaggt ttcgtcaacg aacaagaata catgatgtcc      840
agcttcaaag ccgccatgtc caagttggct atcttgggtc ataacagaaa cgacttgatt      900
gactgttctg aagttgtccc aactcctaag ccaccagtcg gtaagccagc cacttttccca     960 gctaccactg gtccacaaga cttgcaattg acttgtaagt ctgaaagatt ccatccttg      1020
```

| accattgacc acggtgctag agaaaccttg atcccacact gttccaacgg gggtcaagac | 1080 |
| tgtccaactg ttcaattcac cggtccagct ggtgaggacg actctgaaca aaagttgatt | 1140 |
| tctgaagagg atttgtgata a | 1161 |

<210> SEQ ID NO 34
<211> LENGTH: 1161
<212> TYPE: DNA
<213> ORGANISM: Artificial Sequence
<220> FEATURE:
<223> OTHER INFORMATION: Codon Optimized

<400> SEQUENCE: 34

| tacccatacg acgttcctga ttacgctacc atttgtcctg atggtaccag agtctctaac | 60 |
| cacgtttgtt gcgacttcat ccctttggct caagctttgc aatccacttt gtacatgggt | 120 |
| gactgtggtg aagatgccca cgaaactatt agattgacct ccacgacgc tattgctatt | 180 |
| tcccaatctc aaggtccatc tgccggtggt ggtgctgatg gttccatgtt gattttccca | 240 |
| actgtcgaac cattcttcca cgctaacgct ggtattgacg actctgtcaa caacttgatc | 300 |
| ccattcttgg ataagttccc aaccattact gctggtgact tgattcaatt cgccggtact | 360 |
| gtcgccttgt ccaactgtcc aggtgcccca caattggaat ttttggctgg tcgtccaaac | 420 |
| gctaccgctc cagctgttga cggtttgatt ccagaaccac aagataacgt cactcacatc | 480 |
| ttggaaagat cgctgacgc cggtggtttc actccattcg aagtcgttag tttattggct | 540 |
| tctcacaccg tcgccagagc tgataaagtt gacttgacta ttgacgctgc tccattcgac | 600 |
| tctactccat ttactttcga cacccaaatc ttcttggaag tcttgttgaa gggtgttggt | 660 |
| ttcccaggta ccgacaacaa cactggtgaa gtcgaatctc cattgcccctt gggtaacaac | 720 |
| aagcaaggtg gtaacgaaac tggtgaaatg agattgcaat ccgacttcgc cttggctcgt | 780 |
| gatgacagaa ctgcttgttt ctggcaaggt ttcgtcaacg aacaagaata catgatgtca | 840 |
| tcattcaagg ctgctatgtc caagttggcc attttgggtc acaacagaaa cgacttgatc | 900 |
| gactgttctg aagttgtccc aaccccaaag ccaccagttg gtaagccagc ttccttccca | 960 |
| gctactactg gtccacaaga cctacaatta acttgtaagt ccgaaagatt cccatctttg | 1020 |
| accattgacc acggtgccca agaaaccttg atcccacatt gttccaacgg tggtcaagat | 1080 |
| tgtccaaccg ttcaattcac gggtccagct ggtgaagatg actctgaaca aaagttgatt | 1140 |
| tctgaagagg atttgtgata a | 1161 |

<210> SEQ ID NO 35
<211> LENGTH: 1158
<212> TYPE: DNA
<213> ORGANISM: Artificial Sequence
<220> FEATURE:
<223> OTHER INFORMATION: Codon Optimized

<400> SEQUENCE: 35

| tacccatacg acgttcctga ttacgctgtt acctgctctg atggtactgc tgttccagac | 60 |
| gctatgtgtt gtgatttcat tccattggct caagatctac aatcaatggt tttacagaat | 120 |
| caatgcggtg aagatgctca cgaaatcatt agattaacct tccatgacgc cattgctatc | 180 |
| tcccaatcct ggggtccatc cgccggtacc ggtgccgatg gttctatgtt gttgttccca | 240 |
| ttggtcgaac cagaattcgc tgcctccaac ggtattgacg attccgttaa caacttaatc | 300 |
| ccattcttgt cctctcaccc aaacatttca gccggtgact ggtccaatt cgctggtgct | 360 |
| gttgctttga ctaactgccc aggtgcccca agagtcaact tcttggctgg tagaaagaac | 420 |

```
gctgttgctc cagctatcga tggtttaatc ccagaaccac aagacaacgt cacctctatc        480
ttggctagat tcgccgatgc tggtaacttc tccccattcg aagttgtctc cttgttggct        540
tctcactccg ttgctagagc tgacaaggtt gacccaacct tagacgctgc tccattcgat        600
tccactccat tcaccttcga tacccaagtt ttcctagaag tcttgttgaa gggtgttggt        660
ttcccaggta ctgacaacaa tactggtgaa gtcgcctccc cattgccatt cggtgatact        720
tccaccggtg tcaacgatac tggtatgatg agattgcaat ctgacttcgc cttggctcgt        780
gacgaaagaa ctgcttgttt ctggcaatcc ttcgttgatc aacaggactt aatggcccaa        840
agtttccaag ctgctttcga aaagttggct atcttgggtt cctccgcagc tgatttggtt        900
aactgttccg ctgtcgttcc attgtccgtt ggtccagtca ccgccccagc taccttccct        960
gctactaccg ttccacaaga cttgcaatta acctgtacca ctgaaacctt cccatcctta       1020
tctattgatc aggtgctac cgaaaccttg atcccacact gtccagatgg ttccgaagat       1080
tgtccaactg tccaattctc tggcccagct accgactctc agaacaaaa gttgatttct       1140 gaagaggatt tgtgataa                                                      1158
```

<210> SEQ ID NO 36
<211> LENGTH: 1131
<212> TYPE: DNA
<213> ORGANISM: Artificial Sequence
<220> FEATURE:
<223> OTHER INFORMATION: Codon Optimized

<400> SEQUENCE: 36

```
tacccatacg acgttcctga ttacgctgcc gtctgtgctg acggtaccag agtttccaac         60
gctgcttgtt gtgccttcat tccattggct caagacttgc acgaaacctt gttcatgggt        120
gattgtggtg aagatgctca tgaagtcatc cgtttaactt ccacgacgc tgttgccatt         180 tcctcctcta tgggtccatc cgccggtggt ggtgccgatg ttctatgtt gttgttccca        240 accgtcgaac aaacttctc tgctaacaac ggtatcgacg attccgtcaa caacttaatc        300
ccattcttgt ccaagcacgc tgtctctgct ggtgacctag tccaattcgc tggtgctgtc        360
gccttgacca actgtccagg tgctccacaa ttggaattct tggctggtag accaaaccac       420
accattgctg ctatcgacgg tttgatccca gaaccacaag atgacgtcac caagattttg       480
gctagattcg aagatgccgg tggttttttcc ccattcgaag ttgttagttt gttggcttct        540
cataccgttg ccagagctga caaggttgat ggtactatcg atgccgctcc tttcgactct        600
actccattca ctttcgatac ccaagttttt tagaagtct tgttgaaggg taccggtttc        660
ccaggtacta caacaacac tggtgaagtt gcttccccat gccattgac gtccggtaac       720 gacactggtg aaatgcgtct gcagagtgat tcgccttgg ctagagatga agaaccgct         780 tgtttctggc aatctttcgt caacgaacaa gaattcatgg ctcaatcctt caaggctgct        840
atgtccaagt tggccgtttt gggtcactca agatcctctt tggtcgactg ttctgatgtt       900
gtcccagctc caaagccagc cgttaacaag ccagctactt tcccagctac taccggtcca        960
gatgatttgg aattgacttg caccgccgaa agattcccaa ccttgtccgt cgacccaggt       1020
gctcaacaaa ctttgatccc acactgttcc gatggtgatc aagtttgtgc caccgtccaa       1080
ttcactggtc cagctgaaca aaagttgatt tctgaagagg atttgtgata a                1131
```

<210> SEQ ID NO 37
<211> LENGTH: 1131
<212> TYPE: DNA

<213> ORGANISM: Artificial Sequence
<220> FEATURE:
<223> OTHER INFORMATION: Codon Optimized

<400> SEQUENCE: 37

```
tacccatacg acgttcctga ttacgctgct gtttgttctg acggtacccg tgtctccaac       60
tctgcttgtt gtgcctttat cccattggct caagatttgc aagaaacttt gttcatgaac      120
gactgtggtg aagatgctca cgaagtcatc agattgactt ccacgacgc tgttgccatt       180
tctcgttccc aaggtccatc cgccggtggt ggtgctgatg gttccatgct attgttccca      240
accgttgaac caaacttctc cgccaacaac ggtattgacg attctgtcaa caatttgatc      300
ccatttttgg ctaagcaccc tgtttccgct ggtgacctag tccaattcgc tggtgctatt      360
gctttgacta actgtccagg tgctccacaa ttggaattct ggctggtag accaaaccac       420
accattgctg ctgttgacgg tttgatccca gaaccacaag acgatgtcac taagatcttg      480
gctagattcg acgacgctgg tggtttctct ccattcgaag ttgttagctt gttggcttcc      540
cataccgttg ctagagctga taaggtcgac gaaactattg acgctgctcc attcgactct      600
actccattca ctttcgatac ccaagttttc ttggaagttt tgttgaaggg tgtcggtttc      660
ccaggtactg acaacaacac cggtgaagtc gcttccccat tgccattgac ttcaggtaac      720
gacactggtg aaatgagatt gcaatctgac ttcgctttgg ctagagattc agaactgct       780
tgtttctggc aaggttttgt taacgaacaa gaattcatgg ctcaatcttt caaagctgct      840
atgtccaagt ggctgtctt gggtcattct agatcagatt tgatcgactg ttccgatgtt       900
attccaaccc aaaaccagc tgtcaacaag ccagctactt cccagcctc taccggtcca        960
aaggacttgg aattgtcctg tttcgctgaa agattccca ctctaccagt caccctggt        1020
gctactcaaa ctttgatccc acactgttcc aacggtggtg aagattgtcc aacggttcaa      1080
ttcactggtc cagccgaaca aaagttgatt tctgaagagg atttgtgata a               1131
```

<210> SEQ ID NO 38
<211> LENGTH: 1134
<212> TYPE: DNA
<213> ORGANISM: Artificial Sequence
<220> FEATURE:
<223> OTHER INFORMATION: Codon Optimized

<400> SEQUENCE: 38

```
tacccatacg acgttcctga ttacgctacc atctgtccag acggtaccag agtttccaac       60
cacgcctgtt gtgctttcat tccattggct gaggatttgc aaaagactat cttcatgaac      120
gactgtggtg aggatgctca cgaagtcatt agattgacct ccacgacgc tgtcgctatt       180
tctagaaaat tgggtccaaa ggctggtggt ggtgctgacg ttctatgtt gttgttccca       240
accgttgaac caaacttctc cgctaacaac ggtatcgatg actctgttaa caacttgatt      300
ccattcatgg ctagacaccc aacagttagc gctggtgact ggttcaattc gctggtgcc      360
gttgctcttt ctaactgtcc agtgctcct cgtttggaat tcttggctgg tagaccaaac       420
catactatcg ctgctattga tggtttgatt ccagaaccac aagatgacgt cactaagatc      480
ttggaaagat tgatgatgc tggtggtttc accccattcg aagttgtctc cttgttggct       540
tcccacaccg ttgccagagc tgacaaggtc gatgaaacca tcgatgctgc tccattcgac      600
tccaccctt tcactttcga cacccaagtc tttttggaag tcttgttaaa gggtgtcggc       660
ttccctggta ccgataacaa cactggtgaa gttgcttccc cattgccaaa aggttccggt      720
aacgataccg gtgaaatgag attacaatct gacttcgctt tggctagaga tccaagaacc      780
```

| | | |
|---|---|---|
| gcttgtttct ggcaaggttt cgtcgacgaa caagaattca tggctgaatc tttcaaggcc | 840 | |
| gctatggcca agttggctat tttgggccac aacagagcct ccttgaccga ctgttccgat | 900 | |
| gttgtcccaa ttccaagacc agctgtcaaa agcctgcct ccttcccagc tactaccggt | 960 | |
| ccaaaggact tggaattgac ttgtagagct gaaagattcc aactttgac cgttgataga | 1020 | |
| ggtgctgtcc aagctttgat cccacactgt tccaacggtg tcaagattg tccatccgtt | 1080 | |
| caattcgacg gtccagccga acaaaagttg atttctgaag aggatttgtg ataa | 1134 | |

<210> SEQ ID NO 39
<211> LENGTH: 1059
<212> TYPE: DNA
<213> ORGANISM: Artificial Sequence
<220> FEATURE:
<223> OTHER INFORMATION: Codon Optimized

<400> SEQUENCE: 39

| | | |
|---|---|---|
| tacccatacg acgttcctga ttacgctgcc acctgtgctg gtggtcaagt caccgctaac | 60 | |
| gctgcttgtt gtgtcttgtt cccattaatg gaagatttgc aaaagaactt gttcgacgat | 120 | |
| ggtgcttgtg gtgaagatgc tcatgaagct ttaagattga cttccacga tgctatcggt | 180 | |
| ttctctccat ccagaggtgt catgggtggt gctgacggtt ctgttatcac cttctccgac | 240 | |
| accgaagtca acttcccagc taacttaggt atcgacgaaa ttgtcgaagc tgaaaagcca | 300 | |
| ttcttggcca gacacaacat ttctgctggt gatttggttc acttcgccgg tactttggct | 360 | |
| gtcaccaact gtccaggtgc cccaagaatc ccattcttct gggtagacc accagctaaa | 420 | |
| gccgcttccc caattggttt ggtcccagaa ccattcgaca tatcaccga tatcctagct | 480 | |
| agaatggacg atgctggttt cgttagtgtt gaagttgtct ggttgttgag cgctcattcc | 540 | |
| gttgccgctg ccgaccacgt cgacgaaacc atcccaggta ctccattcga ctctaccct | 600 | |
| aacttgttcg actctcaaat cttcattgaa acccaattgc gtggtatctc ttttccaggt | 660 | |
| accggtggta accacggtga agtccaatct ccattgaagg gtgaaatgcg tttgcaatcc | 720 | |
| gatcatttgt tcgcccgtga cgaccgtacc agctgtgaat ggcaatctat gaccaacgac | 780 | |
| caacaaaaaa tccaagacag attctccgac acctgttca agatgtccat gttaggtcaa | 840 | |
| aaccaagacg ctatgatcga ctgttctgac gttatcccag tcccagctgc tttggttacc | 900 | |
| aagccacact acctgctggt aaatctaag accgatgtcg aacaagcttg cgctaccggt | 960 | |
| gctttcccag ctttgggtgc tgacccaggt ccagtcacct ccgttccaag agtcccacca | 1020 | |
| gctgaacaaa agttgatttc tgaagaggat ttgtgataa | 1059 | |

<210> SEQ ID NO 40
<211> LENGTH: 1074
<212> TYPE: DNA
<213> ORGANISM: Artificial Sequence
<220> FEATURE:
<223> OTHER INFORMATION: Codon Optimized

<400> SEQUENCE: 40

| | | |
|---|---|---|
| tacccatacg acgttcctga ttacgctgtt acttgtgcta ctggtcaaac taccgctaac | 60 | |
| gaagcctgtt gtgctttgtt cccaattttg gaagatatcc aaactaactt gttcgacggt | 120 | |
| gctcaatgtg gtgaagaagt tcacgaatct tgagattga ccttccacga tgctattgct | 180 | |
| ttctccccag ccttgactaa cgctggtcaa ttcggtggtg gtgctga tggttctatg | 240 | |
| atcatcttct ctgacactga accaaacttc catgctaact gggtattga tgaaatcgtt | 300 | |

```
gaagctcaaa agccatttat cgcaagacac aacatctccg ctgctgattt catccaattc      360
gccggtgcta tcggtgtcac taactgcgcc ggtgctccaa gattgaactt cttcttgggt      420
agaccagacg ctacccaaat cccaccagac ggtttagtcc cagaaccatt cgattccgtt      480
gacaagatct tgtctagaat gggtgatgcc ggcttctcca ctgtcgaagt cgtgtggttg      540
ttgtctagcc acaccatcgc tgctgctgac ttggttgacc catctatccc aggtactcca      600
ttcgactcta ctccatctac cttcgatagc caattcttct tggaaactat gttgcaaggt      660
actgccttcc caggtactcc aggtaaccaa ggtgaagtcg aatctccatt ggctggtgaa      720
atgcgtttgc aatccgactt cttattggct agagactcca gatccgcttg tgaatggcaa      780
agcatggtca caacatgcc aaagattcaa aacagattca ctcaagttat gagaaagttg       840
tccttgttgg gtcacaacca agctgacttg atcgactgtt ctgatgttat tccagtccca      900
aagactttga ccaaggccgc taccttccca gccggtaagt cccaagctga cgtcgaaatc      960
gttgtggccg ctactccatt cccagccttg gcttctgatc caggtccagt caccgccgtt     1020
ccaccagtcc caccatctga acaaaagttg atttctgaag aggatttgtg ataa           1074

<210> SEQ ID NO 41
<211> LENGTH: 1056
<212> TYPE: DNA
<213> ORGANISM: Artificial Sequence
<220> FEATURE:
<223> OTHER INFORMATION: Codon Optimized

<400> SEQUENCE: 41
tacccatacg acgttcctga ttacgctgct acctgtgccg acggtagaac cactgccaat       60
gctgcttgtt gtgtcttatt cccaatttg gacgatatcc aagaagctct attcgatggt       120
gccgaatgcg gtgaagaagt ccacgaatcc ttgagattga cttttccacga tgctatcggt      180 ttctccccaa ccaagggtgg tggtggtgct gacggttcca tcgttacttt tgacgaaatt      240
gaaactgctt tccacgctaa cggtggtatc gatgacattg tcgacgctca aaagccattc      300
attgccagac acaacatctc tgctggtgac ttcatccaat tcgccggtgc tgtcggtgtt      360
tccaattgtc caggtgctcc aagattgaac ttcttattgg gtagaccacc agctactgct      420
gcctccccaa acggtttgat tccagaacca ttcgatactg tcactgatat tttggctaga      480
atgggtgacg ctggtttctc cccagaagaa gttgttgcct tgttggctag ccatagcgtc      540
gctgccgctg accacgttga tgaaactatc ccaggtaccc cattcgactc tactccaggt      600
gaattcgatt cccaattctt cattgaaact caattgagag gtaccgcttt ccctggtgtc      660
ggtggtaacc aaggtgaagt cgaatcccca ttggctggtg aaatcagaat ccaatccgat      720
catgacttag ccagagattc cagaactgct tgtgaatggc aatctttcgt caacaaccaa      780
gctaagttgc aatctgcctt caaggctgct atggataagt tggctacttt gggtcaagac      840
agatctaagt taatcgactg ttccgatgtc atccctgtcc caaagccttt gcaatccaag      900
gcccacttcc cagctggttt gaccatgaac aacatcgaac aagcttgtgc ttctactcca      960
ttcccagctt tgactgctga cccaggtcca gtcactaccg ttccaccagt cccaccatcc     1020
gaacaaaagt tgatttctga agaggatttg tgataa                              1056

<210> SEQ ID NO 42
<211> LENGTH: 1074
<212> TYPE: DNA
<213> ORGANISM: Artificial Sequence
<220> FEATURE:
<223> OTHER INFORMATION: Codon Optimized
```

<400> SEQUENCE: 42

```
tacccatacg acgttcctga ttacgctgcc aagtgttcta agggtagaac tgcttccaac      60
gacgcttgtt gtgtctggtt cgatgttttg gatgatatcc aagaaaactt gttcgacggt     120
ggtgaatgtg gtgaagaagt ccatgaatct ttaagattga ctttccacga tgccattggt     180
ttctccccag ctttgacccg tcaaggtaaa ttcggtggtg gtggtgctga cggttccatc     240
atgttgttct ctgacattga aactaacttc gccgctaaca acggtgttga cgacatcgtc     300
gaacaacaaa agccaatcgc tatcaaacac caagtttcct ttggtgactt catccaattt     360
gctggtgccg tcggttcctc taactgtgct ggtggtccac gtattcaatt cctggccggt     420
agatccaacg tcaccaagcc atccccagat cacctagtcc cagaacccctt tgactctgtt     480
acctccatct ggctagaat gggtgatgct ggtttcaagc ctgacgaggt tgttgctttg     540
ttggccagcc attccgttgc tgcccaagat accatcgacc caaagttggc tggtcaccca     600
tcgactcta ctccatctga ctttgacagt caattcttg ttgaaaccctt gttaaagggt     660
accttgattc aggtgactc cttgcataag ggtcaagtca agtccccatt gccaggtgaa     720
ttcagattgc aatccgacga gttgttggct agagactcca gaacctcttg tgaatggcaa     780
tcctttatttt ctaacccaaa ctccatggtc ccaaagttcg aaagagctat ggctaagatg     840
gctaccttgg gtcaaaaccc aaagaagttg attgattgtt ctgaagtcat cccagtccca     900
cgtggtagag ttaagcaacc gaccttacct gcgggtaaga ctattaagga catcgaagcc     960
tcctgtagaa aggctccatt cccacgtttg ccaaccgaca agggtacttt cacctctatc    1020
ttgccagtcc catcctccga acaaaagttg atttctgaag aggatttgtg ataa           1074
```

<210> SEQ ID NO 43
<211> LENGTH: 1065
<212> TYPE: DNA
<213> ORGANISM: Artificial Sequence
<220> FEATURE:
<223> OTHER INFORMATION: Codon Optimized

<400> SEQUENCE: 43

```
tacccatacg acgttcctga ttacgctgct acctgtgctg acggtaacac tgtcactaac      60
gctgcttgct gtgtcttgtt ccctatcttg gaagatattc aaaccaactt gttcgatggt     120
ggtgaatgtg gtgaagaagt tcacgaatct ttgagattga ccttccacga cgccatcggt     180
ttctccccat ctagaggtgg tggtggtgct gacggttcct taatcaccctt ctccgaaatc     240
gaaacccccat tccatgccaa cttgggtatc gacgaaattg tcgaagctca aaagccattc     300
gttgctaagc acaacatctc cgccggtgat tcatccaat tcgctggtgc cgtcggtgtc     360
tctaactgtc aggtgccccc acgtctacaa ttcttcttgg gtagaccaga cgctgttgct     420
ccagctccag atttgacggt cccagaacct ttcgacagcg tcgactccat cttggctaga     480
ttcgctgatg ccggtttctc tccagctgaa gttgttgctt tgttggcctc gcataccatc     540
gctgccgccg acaacgtcga cccaactatc ccaggtactc catttgactc tactccatct     600
gctttcgact cccaattctt cgttgaaacc caattgcgtg gtacttcctt cccaggtacc     660
gctggtaacc aaggtgaagt tgaatcccca ttgagaggta aatgagatt gcaatctgac     720
tccgaattgg ctagagatcc aagaaccgcc tgtgaatggc aatctttcgt caacaaccaa     780
tccaagttgc aatccgcttt caaggctgct atgttaaagt tgtccttggt tgctcaagac     840
aagtctaagt tggtcgactg ttctgacgtt atcccagtcc ccccaaccctt gaacgccgcc     900
```

| | |
|---|---|
| gctcacttcc cagctggttt gaccaagaac gatgttgaac aagcttgcgc tgccacccca | 960 |
| ttcccagctt tgactaccga cccaggtcca gtcaccgccg ttccaccagt tattccagct | 1020 |
| ttgttgccag aacaaaagtt gatttctgaa gaggatttgt gataa | 1065 |

```
<210> SEQ ID NO 44
<211> LENGTH: 1068
<212> TYPE: DNA
<213> ORGANISM: Artificial Sequence
<220> FEATURE:
<223> OTHER INFORMATION: Codon Optimized

<400> SEQUENCE: 44
```

| | |
|---|---|
| tacccatacg acgttcctga ttacgctgct acttgttccg gtggtagaac caccgcccac | 60 |
| gcttcttgtt gtatctggtt cgacgtcctg gacgacatcc aagaaaactt gtttgacggt | 120 |
| ggtgaatgcg gtgaagaagt tcatgaatcc ttgagattga ccttccacga cgctatcggt | 180 |
| ttctccccaa agttgttctt gcaaggtaag ttcggtggtt taggtgctga cggttccatc | 240 |
| atggctcact ctgaaatcga aactgctttc ccagctaact gggtgttga cgaaatcatt | 300 |
| gaagctcaaa gaccattcgc cattaaacac aaagttagct ttggtgactt catccaattc | 360 |
| gccggtgctg ttggtgtttc aactgtgct ggtggtgcta gaattccatt ccacgctggc | 420 |
| agattgaacg tttctttgcc atccccagat ctattggttc cagaaccatc ggattctgtt | 480 |
| gacaccatct ggctagaat gggtgatgct ggttctctccc caaacgaagt cgttgacttg | 540 |
| ttgatctctc acaccgttgc tgctcaagac aacgttgacc caaccatccc aggtacccca | 600 |
| ttcgattcca ctcaaaactc ttttgacgcc caattcttcg tcgaaacctt gttgaagggt | 660 |
| tctattactc caggtaacgg taccaacaga ggtcaatcct tatcccctat cccaggtgaa | 720 |
| ttcagattga cttctgactt cttgttggct cgtgacgcga gaactgcctg tgaatggcaa | 780 |
| tccttcatca ccgaccatgc ctccatggtt tctaagtttg aaaaggtcat ggataagatg | 840 |
| tccaccttgg gtcaaattag agctttgttg actgactgtt ctgacgtcat tccagttcca | 900 |
| aaggttgctt taaccaagac cccaaccttg ccagctggta agcttggc tgacatcgaa | 960 |
| gctgcttgtc gtgctactcc attcccagct ttgaccgccg acccaggtcc agttaccacc | 1020 |
| gtcccaccag ttgaacaaaa gttgatttct gaagaggatt tgtgataa | 1068 |

```
<210> SEQ ID NO 45
<211> LENGTH: 1170
<212> TYPE: DNA
<213> ORGANISM: Artificial Sequence
<220> FEATURE:
<223> OTHER INFORMATION: Codon Optimized

<400> SEQUENCE: 45
```

| | |
|---|---|
| tacccatacg acgttcctga ttacgctgtt acttgttctg acggtaccgt tgttccagac | 60 |
| tccgtctgtt gtgaattcat tccattgaga gaagctttga cgaccaagt tattcaatcc | 120 |
| gattgtggtg aggatgctca cgaattattg agattgactt ccacgacgc catcgctatt | 180 |
| tcccaatctt tgggtccttc cgctgggggt ggtgctgacg gttctatgtt gttattccca | 240 |
| accgtcgaac cagcttttctt cgccaacttg gtatcgctg actccgttaa caatttgatc | 300 |
| ccattcatgt cccaattccc aaacatctcc ccaggtgact tggtccaatt cgctggtgct | 360 |
| gttgccatta ctaactgtcc aggtgctcca caattggaat tcttggctgg tagaccaaac | 420 |
| ggtactgcac cagctatcga tggtttgatc ccagaaccac aagattccat tgacgatatc | 480 |
| ttggctagat tcgacgacgc tggtggtttc actccattcg aagttgtttc tctgttggct | 540 |

```
tcccatactg ttgctagagc tgaccacgtc gacccaacct tggacgctgc tccatttgac    600
tctaccccat tcaccttcga tacccaaatc ttcttggaag ttttgttgaa gggtaccggt    660
ttcccaggta ccgacaacaa caccggtgag gttgccagcc caattccagt tactaacggt    720
accgatgttg tgaattgag attgcaaagc gacttcggtt tggctcacga ttccagaacc     780
gcttgtttct ggcaaggttt cgtcaaccaa caagatttca tggcccaatc tttcaaggct    840
gctatggcca agttggctgt tttgggtcac aacgctgctg atttggttaa ctgttccgcc    900
gttattccaa ccccattgcc agctactggt aagccagcta ccttcccagc tactttgggt    960
ccagacgatt tggaattgtc ttgtaccacc gaaccattcc catctctaac taccgaccca   1020
ggtgcccaag aaaccttaat tcctcactgt tctgatggtt ccatggactg tgagtctgtt   1080
caatttgacg gtccagctac taacttcggt ggtgatgacg atgatgacga ttctgaacaa   1140
aagttgattt ctgaagagga tttgtgataa                                    1170
```

<210> SEQ ID NO 46
<211> LENGTH: 1158
<212> TYPE: DNA
<213> ORGANISM: Artificial Sequence
<220> FEATURE:
<223> OTHER INFORMATION: Codon Optimized

<400> SEQUENCE: 46

```
tacccatacg acgttcctga ttacgctacc gtctgttccg atggtaccgt cgttccagac     60
tctgtctgtt gcgaattcgt cccattggct caagctttgc aaaaggaagt tttgatgggt    120
gattgtggtg aggatgctca cgaattattg agattgactt ccacgacgc catcgctatt     180 tccagatcta agggtccatc cgctggtggt ggtgccgacg ttctatgtt gatcttccca     240 accgtcgaac cagcttttctt cgctaacttg ggtatcgctg actctgtcaa caatttgatt    300
ccattcttgt cccaattccc aaagatctct gctggtgact tggtccaatt cgctggtgcc    360
gttgccgtcg gtaactgtcc aggtgcccca caattggaat ccgtgccgg tagaccaaac    420 gccaccgccc cagctatcga aggtttgatt ccagaaccac aaaacaacat taccgaaatt    480
ttggaaagat tcgacgacgc tggtggtttt tcccccattcg aagtcgtttc tttgttggct    540
tcacatactg tcgccagagc cgatcacgtc gacccaacct tggatgctgc tccattcgac    600
tctactcctt tcactttcga tacccaaatt ttttggaag ttttgttgaa gggtgtcggt     660
ttcccaggta ccggtaacaa cactggtgaa gttttcctccc cattgccagt ctcttctggt    720
accgacgtcg tgaattgag attgcaatcc gacttcggtt tagctcacga tgaacgtact    780
gcctgtttct ggcaaggttt cgttaatgaa caagaattca tggcccaatc cttcaaagcc   840
gctatggcta agttggctgt cttgggtcac aacgccgacg atttggtcga ctgttccgct    900
gtcgtcccaa agccaaagcc agccaccggt aagccagctt ccttcccagc aaccaagggt   960
ccaaaggact tggaattgtc ctgtacttct aagaagttcc aaccttgac caccgaccac   1020 ggtgctcaag aaactttgat cccacactgt tccaacggtt ccatgaattg taccactgtc   1080
caattcgatg gtccagccac caacttcgac ggtgatgact ccgaacaaaa gttgatttct   1140
gaagaggatt tgtgataa                                                 1158
```

<210> SEQ ID NO 47
<211> LENGTH: 1080
<212> TYPE: DNA
<213> ORGANISM: Artificial Sequence
<220> FEATURE:

<223> OTHER INFORMATION: Codon Optimized

<400> SEQUENCE: 47

| | |
|---|---|
| tacccatacg acgttcctga ttacgctgtc gcttgtccag acggtgttaa caccgctact | 60 |
| aacgctgctt gttgtcaatt gttcgctgtc cgtgacgaca ttcaaaagaa cttgtttgat | 120 |
| aacggtgaat gtggtgaaga tgttcacgaa tccttgagat tgaccttcca tgacgccatc | 180 |
| ggtttctcca gatctgctga agctaatggt actttcggtg gtggtggtgc cgatggttcc | 240 |
| atcagcatct tcgcttccat tgaaaccaac ttccacgctt ccttgggtat cgatgaaatc | 300 |
| gtcggtgaac aagctccatt catcgctaga cacaatttaa ccgttggtga tttcatccaa | 360 |
| ttcgctggtg ctgttggtgt ttctaactgc ccaggtgccc aagattgca attcttgttg | 420 |
| ggtagaccaa acgctaccca accagctcca gacaagacta tcccagaacc attcgacacc | 480 |
| gttgattcca tcttggccag attcttggac gctgctgatt tctctcctgc tgaagttgtt | 540 |
| gctttattgg cttcccacac tattgctgct gctgacgaag tcgacccaac cattccaggt | 600 |
| actccattcg actccacccc agaattgttt gatactcaat tcttcatcga aacccaattg | 660 |
| agaggtaccg gtttcccagg taccgctggt aaccaaggtg aagttttatc cccattgcca | 720 |
| ggtgaaatga gattgcaatc tgactccgaa ttggccagac tccagaacc gcttgtgaa | 780 |
| tggcaatcta tggttaacaa ccaatctaag atgatgaccg ctttcgccgc tgccatggct | 840 |
| aagttggctg tcatcggtca agacgtttct caattgattg actgttccga agttatccca | 900 |
| atgccaccac caccagcttc cgctgctcac ttcccagccg tttatccaa cgctgatgtt | 960 |
| gaacaagcct gtgctgaaac tccattccca accttgcaaa ccgaccctgg tccagaaacc | 1020 |
| tctgtcgctc cagttccacc atccgaacaa aagttgattt ctgaagagga tttgtgataa | 1080 |

<210> SEQ ID NO 48
<211> LENGTH: 1077
<212> TYPE: DNA
<213> ORGANISM: Artificial Sequence
<220> FEATURE:
<223> OTHER INFORMATION: Codon Optimized

<400> SEQUENCE: 48

| | |
|---|---|
| tacccatacg acgttcctga ttacgctgtc acttgtgctt ccggtcaagt tacctccaac | 60 |
| gctgcttgtt gtgccctatt cccagtcatc gatgatattc aagccaatat gttcgacggt | 120 |
| ggtgaatgta acgaagatgt tcacgaatcc ctaagattga ccttccacga tgccatcggt | 180 |
| atttcccgta aggctaacaa ggccggtgtc tttggtggtg gtggtgccga cggttccatc | 240 |
| gctattttcg ctgacattga aactaacttt cacgctaaca acggtgttga tgaaatcatt | 300 |
| gacacccaag ctccaatcat cgctagacat aacctaacca ctgctgactt catccaattc | 360 |
| gccggtgcta ttggtgtttc taactgtcca ggtgccccaa gattggatgt cttttttgggt | 420 |
| agaaaggatg ctacccaacc agccccagac ttgaccgttc ctgaaccatt cgatgacgtc | 480 |
| actaagattt ggctagatt cgatgacgcc ggtaagttct cctctgacga agttgttgcc | 540 |
| ttgttggttt ctcacaccat tgctgctgct gaccacgttg atccaactat tccaggtacc | 600 |
| ccattcgact ccacccccaga attattcgac acccaattct tcatcgaaac ccaattgcaa | 660 |
| ggtactttgt tcccaggtaa cggttccaac caaggtgaag ttatgtcccc attgagaggt | 720 |
| gaaattagat tgcaatccga cttcttgttg gctagagatt ctagaaccgc ttgtgaatgg | 780 |
| caatccttcg ttaacaacca atacaaattg caatccgctt tcaaggctgc tttccgtaag | 840 |
| atgactatct tgggttccaa ggaacacaac ttgattgatt gttctgatgt tgtcccaact | 900 |

```
ccaccagccc cagcttctaa agctcacttg ccagccggtt tgaccagaca agatgttcaa    960
caagcttgca acaagaaggc cttcccaacc ttgccaaccg acccaggtcc agtcacttcc   1020
gttgccccag tcccaccctc cgaacaaaag ttgatttctg aagaggattt gtgataa     1077
```

<210> SEQ ID NO 49
<211> LENGTH: 1080
<212> TYPE: DNA
<213> ORGANISM: Artificial Sequence
<220> FEATURE:
<223> OTHER INFORMATION: Codon Optimized

<400> SEQUENCE: 49

```
tacccatacg acgttcctga ttacgctgtt gcttgtccag atggtgtcaa caccgctacc     60
aacgccgctt gttgtcaatt gttcgctgtt cgtgacgata tccaacaaaa cttattcgac   120
ggtggtgaat gtggtgaaga agttcacgaa tccttgcgtt taaccttcca cgacgctatc   180
ggtatctccc cttctatcgc ttcccgtggt caattcggtg gtggtggtgc tgacgggtcc   240
attgctttgt ttgaagatat tgaaactaac ttccacgcta acttgggtgt tgatgaaatt   300
atcgacgaac aaagaccatt catcgccaga cacaacttga ccactgctga cttcattcag   360
tttgccggtg ctatcggtgt ttccaactgt ccaggtgctc acaattgga tgtttttatt   420
ggtagaccag acgccaccca accagcccca gatttgaccg ttccagaacc atttgacacc   480
gtcgactcta ttattgaaag attctccgat gctggtggtt tcactccagc tgaaatcgtt   540
gctttgttgg tttctcacac catcgctgca gctgaccacg tcgacccatc catcccaggt   600
accccattcg attccacccc agaagaattc gacactcaat tctttatcga aactcaattg   660
agaggtacct tgttcccagg tactggtggt aaccaaggtg aagttgaatc cccattaaga   720
ggtgaattgc gtttgcaatc agattccgaa ttggccagag attccagaac cgcttgcgaa   780
tggcaatcct tcgtcaacaa ccaagctaag ttgcaatccg cttcaaggc tgctttcaga   840
aagatgactg ttttgggtca cgacgaatcc ttgttgattg aatgctccga attggtccca   900
actccaccac cagccaccctc tgttgctcac ttccctgctg gtttgtccaa cgctgacgtc   960
gaacaagcct gtgctgaaac cccattccca actttaccaa ccgatccagg tccagttact  1020
actgttgctc cagttccacc atccgaacaa aagttgattt ctgaagagga tttgtgataa  1080
```

<210> SEQ ID NO 50
<211> LENGTH: 2328
<212> TYPE: DNA
<213> ORGANISM: Artificial Sequence
<220> FEATURE:
<223> OTHER INFORMATION: Codon Optimized

<400> SEQUENCE: 50

```
tacccatacg acgttcctga ttacgctcaa tccgcttctc aattcactga cccaactacc     60
ggtttccaat tcaccggtat taccgatcca gtccacgacg ttacttacgg tttcgttttc   120
ccaccattgg ccacctctgg tgcccaatct accgaattca tcggtgaagt cgttgcccca   180
attgcttcca gtggatcgg tattgctttg gtggtgctta tgaacaacga tttgttactg   240
gtcgcctggg ctaacggtaa ccaaattgtc tcttctacca gatgggccac cggttacgtt   300
caaccaaccg cttacaccgg taccgctact tgaccacct tgccagaaac caccattaat   360
agtacccatt ggaagtgggt cttagatgt caaggttgta ctgaatggaa caacggtggt   420
ggtatcgacg tcacctccca aggtgttttg gcttgggctt tctctaacgt cgccgttgat   480
```

```
gacccatctg acccacaatc caccttctcc gaacatactg atttcggttt cttcggtatc    540
gactactcca ccgctcactc agccaactac caaaattact tgaacggtga ctctggtaac    600
ccaaccacta cctctactaa gccaacctcc acctcctcct ccgtcaccac cggtccaact    660
gtctccgcca ctccatacga ttacattatc gtcggtgctg gtccaggtgg tatcatcgct    720
gctgaccgtt tgtctgaagc cggtaagaag gtcttgttgt tggaaagagg tggtccatct    780
actaagcaaa ccggtggtac ctacgttgct ccatgggcta cctcttccgg tttgactaag    840
ttcgacatcc caggtttgtt cgaatctttg ttcaccgatt ctaacccatt ctggtggtgt    900
aaggacatca ctgtctttgc tggttgtttg gtcggtggtg gtacctccgt taacggtgct    960
ttgtactggt acccaaacga tggtgacttc tctagctctg tcggttggcc atcctcctgg   1020
accaaccatg ccccatacac ctccaagctt agcagtagat tgccatccac cgatcaccca   1080
tccactgacg gtcaaagata cttggaacag tcctttaacg ttgtctccca attgttgaag   1140
ggtcaaggtt acaaccaagc taccattaac gataacccaa actacaaaga ccacgttttc   1200
ggttactctg ccttcgactt cttgaacggt aaaagagccg tccagtcgc tacctacttg    1260
caaactgctt tggctagacc aaacttcacc ttcaagacca cgttatggt tagtaacgtc    1320
gttagaaacg gttcccaaat tttaggtgtc caaaccaacg acccaacttt gggtccaaac   1380
ggtttcattc cagttacccc aaaaggtaga gtcatcttgt ctgctggtgc tttcggtact   1440
tccagaattt tgttccaatc aggtatcggt ccaactgaca tgatccaaac cgttcaatct   1500
aacccaactg ccgctgctgc tttgccacca caaaaccaat ggatcaactt gccagtcggt   1560
atgaacgccc aagacaaccc atccatcaac ttggtttca cccacccatc catcgacgct   1620
tacgaaaact gggccgacgt ttggtctaac ccaagaccag ctgacgccgc tcaatacttg   1680
gctaaccaat ccggtgtctt tgctggtgct tcccccaaagc taaacttctg gagagcatac   1740
tctggttccg acggtttta cagatacgct caaggtaccg tccgtccagg tgctgcttcc   1800
gtcaactcct ccttgccata caacgcctct caaattttca ccattactgt ttacttgtct   1860
accggtatcc aatccagagg tcgtattggt atcgacgctg ctttgagagg tactgtcttg   1920
accccaccat ggctagtcaa ccctgtcgac aagaccgttt tgttgcaagc cttgcacgac   1980
gtcgtttcca acatcggttc cattccaggt ttaactatga ttaccccaga tgtcacccaa   2040
actttggaag aatacgtcga cgcttacgat ccagcgacta tgaactcaaa ccattgggtc   2100
agttccacca ccatcggttc ctctccacaa tccgctgtcg ttgactctaa tgttaaggtt   2160
ttcggtacta caaacctatt cattgtcgac gccggtatca ttccacactt gcctaccggt   2220
aacccacaag gtactttgat gtctgctgct gaacaagctg ctgctaagat cttggcctta   2280
gctggtggtc agaacaaaa gttgatttct gaagaggatt tgtgataa              2328
```

<210> SEQ ID NO 51
<211> LENGTH: 2331
<212> TYPE: DNA
<213> ORGANISM: Artificial Sequence
<220> FEATURE:
<223> OTHER INFORMATION: Codon Optimized

<400> SEQUENCE: 51

```
tacccatacg acgttcctga ttacgctcaa tccggttctt cctacactga cccagacaac     60
ggttttgttt tcaacggtat taccgatcca gtttacggtg tcacctacgg tgttgttttc    120
ccagaaccat cttcttccgg tacctaccca gacgaattca ttggtgaaat tgtcgcccca    180
ttgaccgctg aatggattgg tgtttccttt ggtggtgcta tgttagactg tttgttgttg    240
```

```
gtcgcttggc caaaccaaaa ctccattgtc gcttctacta gatacgcaac cgattacgtc    300
caaccaactg aatacgacgg tccagttttg actactttgc catcctccta cgtcaactcc    360
actcactgga agtacgttta cagatgtcaa aattgtacta cttggcaagg tggtggtatc    420
tctttgggtg gtactggtgt tttggcttgg gcttactcca acgtcggtgt cgatgaccca    480
tctgacccag aatctaactt cttagaacac accgatttcg gtttcttcgg tgaaaacttc    540
ggtcaaactg aaaacgctaa ctacaataat tacgttaacg gtaatccagg tacaccgact    600
tcaaccccac caactacttc tccaaccggt ccaactacta cttcaccagc ttccccacca    660
accgcttctg ctaccccata cgactacatc attgtcggtg ctggtgccgg tggtatcatt    720
gctgctgata gattgtccca aaacaacaag aaggtcttgt tgttggaaag aggtggtcca    780
tccactggtg aaaccggtgg tacttacgtt gccgactggg ctgaaggtac caacttaact    840
aagttcgata ttccaggttt gttcgaatct atgttcgacg atccagatcc atggtactgg    900
tgttccgatg ttacttttcta cgctggttgt ttgttaggtg gtggtactag tgtcaacggt    960
gctttgtact ggtacccaac cgataccgat ttctctactg ctagaggttg gccatcctcc   1020
tggtctaacc accaagctta cactaatgct atgactcaga gattgccatc cactgaccat   1080
ccatctactg atggtgaaag atacttggaa caatctgccc aagttgctat gcaattattg   1140
aacgctcaag ttattacca gctaccatc aacgattctc cagattccaa ggatcacgtc   1200
tacggttact ctgctttcga cttcattaac ggtaaaagag gtggtgtcgt tgctacctac   1260
cttcaaactg ctaaccaaag atctaacttc gtctacaagg actacacttt ggttagttct   1320
gtcgtcagaa atggttccca aatcttgggt gtccaaacta caacactgc cattggtcca   1380
aacggtttta tcccttttgaa cccaaacggt agagtcatct tgtccgctgg gtctttcggt   1440
actccaagaa tcttattcca atctggtatt ggtcctactg acatgttgca aaccgttcaa   1500
caaaacgctg ctgtcgctgc caacatgcca tccgaaagcg actggattaa cttgccagtc   1560
ggtatgaacg tttccgacaa cccatctatc aacttggttt ttactcaccc atccatcgac   1620
gcttacgata actgggctga cgtctggact gacccacgtc cagccgacgc tgctcaatac   1680
ttggcttccc aatctggggt tttcgccggt gcttctccaa aattgaactt ctggagagat   1740
tacgaaggtt ccgatggtat tcaaagatcc gctcaaggta ctgtcagacc aggtgctgct   1800
tctgtcaaca ccactttgcc atacaacgct tcccaaatct tcactattac cgtttacctg   1860
agtagtggta tcacttccag aggtcgtatc ggtgtgaccg ctggtttgaa cgccgtcgct   1920
ttggaaaacc catggttgac tgaccctgtc gataaggttg tcttgatcca agctttggaa   1980
gatgttatct ctaccttgcc atccgtccca gatttgacta tgatcactcc agattctggt   2040
atgaccttgg aagaatacgt cgatttgtac gacccatcta ctatgtgttc caaccactgg   2100
gttggttctg ctaagatggg tacttcctct gatactgctg ttgtcgacga aaacgctaag   2160
gttttcaaca ccgataattt gttcgttatt gacgcttcta tcgttccatc cttgccagtc   2220
ggtaacccac acggtactgt catgtctgct gccgaacaag ctgtcgctaa catcttggct   2280
ttgtccggtg gtccagaaca aaagttgatt tctgaagagg atttgtgata a            2331
```

<210> SEQ ID NO 52  
<211> LENGTH: 2310  
<212> TYPE: DNA  
<213> ORGANISM: Artificial Sequence  
<220> FEATURE:  
<223> OTHER INFORMATION: Codon Optimized

```
<400> SEQUENCE: 52
tacccatacg acgttcctga ttacgctcaa gtcgccgctc catacgtcga ctctggtaac      60
ggtttcgtct ttgacggtgt cactgaccca gttcactccg tcacctacgg tatcgttttg     120
ccacaagctt ctacttccac tgaattcatt ggtgaattcg tcgctccaaa cgaagctcaa     180
tggatcggtt tggctttggg tggtgctatg attggtaact tgttgttggt cgcttggcct     240
aacggtaata aaattgtttc ctcgccaaga tacgctactg gttacacttt gccagctgct     300
tacgctggtc caaccatcac tcaattgcct tcttcctccg ttaactccac ccactggaag     360
ttcgttttca gatgccaaaa ctgtactgct tggaacggtg gttccatcga cccatccggt     420
accggtgttt tcgcttgggc tttctccaat gtcgctgttg acgatccatc cgacccaaac     480
tcttctttcg ctgaacacac cgatttcggt ttttttcggta tcaactttcc agatgctcaa     540
tcctccaact accaaaacta cttggctggt aacgctggta ccccaccacc aacctctgtc     600
ccatccggtc catcctctac tactactacc actggtccaa ctgccactgc tactcctttc     660
gactacatcg ttgtcggtgc tggtccaggt ggtttggtta ccgctgacag attgtccgaa     720
gccggtaaga agtcttgtt gttggaaaga ggtggtccat ctacggctga aactggtggt     780
acttacgatg ctacttgggc taagtccgca aacttgacca agttcgacgt cccaggtttg     840
ttcgaaacct tgttcactga cactaaccca ttctggtggt gtaaggacac caatttcttt     900
gctggttgtt tgttgggtgg tggtacttct gtcaacggtg ctttgtactg gtacccaaac     960
tctagagact tctccactgc ttctggttgg ccatcctctt ggtctaacca ccaaccattc    1020
actgataagt tgaagcaaag attgccatcc accgaccacc catctgccga tggtcaaaga    1080
tacttagaac aatccgctac tgtcgtccaa caattgttgt ctggtcaagg ttactcccaa    1140
atcaccatca acgtaaccc tgactccaag gatcacgttt tcggtttctc tgctttcgac    1200
ttcttgaacg gtcaacgtgc tggttccgtc gctacttact tcgaaactgc tttggctaga    1260
aagaacttcg tctacaagga caacgtcctt gttactcaag ttattagaaa cggttctact    1320
atcttgggtg tcagaactaa cgataacacc ttgggtccag acggtgttgt cccattgaac    1380
ccaaacggta gagtcatctt gtccggtggt agcttcggta ctccacgtat tttgtttcaa    1440
tcaggtatcg gtccaaccga tatgttgcaa accgtccaat ccaacgctca agctgctgct    1500
aacttgccac acaatccgta atggattgat ttgccagtcg gtcaatccgt ttctgataac    1560
ccttccatca acttggtttt tacccaccca tccatcgacg cttacgacaa ctgggctgat    1620
gtttggtcca acccaagacc agctgatgct caacaatact tgcagtctag atccggtgtc    1680
ttggctggtg cttctttgaa gttgaacttc tggagagctt acggtggttc cgacggtatc    1740
actggttacg ctcaaggtac cgttagacca ggtgctgctt ctgttaacac ttccgtcgct    1800
tacaacgctt ctgaaatttt cactactact ttgtacttgt ctaacggtat ccaatcccgt    1860
ggtagaattg gtgtcgacgc taccttgaac gctaaggctt tggttaaccc atggttgact    1920
aactctgttg ataagaccgt tttgttgcaa gctttgcacg atgttacttc caccatgaaa    1980
aacgttagtg gtttgactat gatcactcca gacaacacta tgactctaga acaatacgtt    2040
gctgcttacg atccagctac catgtgttct aaccactggg ttggtgctgc taagatgggt    2100
acctcttcct ccactgctgt cgttgacgaa aacgctaagg ttttttaacac cgataacttg    2160 ttcatcgtcg acgcctctat cattccatct ttgccaatcg gtaacccaca aggtgtcttg    2220
atgtccgctc tgaacaagc tgtttctaga attttggctc tagctggtgg tcctgaacaa    2280
aagttgattt ctgaagagga tttgtgataa                                     2310
```

<210> SEQ ID NO 53
<211> LENGTH: 2313
<212> TYPE: DNA
<213> ORGANISM: Artificial Sequence
<220> FEATURE:
<223> OTHER INFORMATION: Codon Optimized

<400> SEQUENCE: 53

| | |
|---|---|
| tacccatacg acgttcctga ttacgctcaa gtcgctgccc catacgtcga ttccggtaac | 60 |
| ggtttcgtct ttgacggtat tactgatcca gtttaccacg tcagttacgg tatcgttttg | 120 |
| ccacaagcta ccacttcctc cgaattcatc ggtgaaattg tcgctccatt ggatgctaag | 180 |
| tggatcggtt tggctttggg tggtgctatg atcggtgacc tattgatcgt cgcttggcca | 240 |
| aacggtaacg aaattgtttc ctccaccaga tatgctaccg cttaccaact gccagatgtt | 300 |
| tacgctggtc aactatcac tactttgcct tcctccttgg tcaactccac tcactggaag | 360 |
| tttgttttca gatgtcaaaa ctgtacctct gggaaggtg gtggtggtat cgacccaact | 420 |
| ggtactggtg ttttttgcttg ggcttactcc tctgtcggtg ttgatgaccc atctgaccca | 480 |
| aacaccacct tccaagaaca caccgacttc ggtttcttcg gtattaactt tccagacgct | 540 |
| caaaacagta actaccaaaa ctacttgcaa ggcaacgctg gtactccacc accaacctct | 600 |
| actccatctg gtccaaccac cacttccaag cctaccggtc aactgcttc tgctaccca | 660 |
| tacgattaca tcattgtcgg tgccggtcct ggtggtatca ttgctgccga ccgtttgtct | 720 |
| gaagctggta agaaggttat cttgttggaa agaggtggtc catccaccgc tgaaactggt | 780 |
| ggtacctact acgctccatg ggctaagtcc caaaacttga ctaaattcga tattccaggt | 840 |
| ttgttcgaat ctatgttcac cgacccaaac ccatggtggt ggtgtaaaga cactaacttc | 900 |
| ttcgctggtt gtttgttggg tggtggtact tctgtcaacg gtgctttgta ctggttacca | 960 |
| tctgacgctg atttctctac cgccaacggt tggccaacta actggggtaa ccatgctcca | 1020 |
| tacacctcca gttgaagca cgtttgcca tctactgacc acccatccgc tgacggtaac | 1080 |
| agatacttgg aacaatccgc taccgttgtc tcccaattgt tgcaaggtca aggttaccaa | 1140 |
| caaatcacca ttaacgacaa cccagattac aaggaccatg tctttggtta ctctgctttc | 1200 |
| gacttcatca acggtcaaag agctggtcca gttgctacct acttccaaac tgcttccgct | 1260 |
| agaagcaact tcgtctacaa ggactacacc ttggtttcac aagtcttgag aaacggttcc | 1320 |
| actatcaccg tgtcagaac taacaacact gctttgggtc agacggtat cgtcccattg | 1380 |
| aacccaaacg tagagttat tttggctgct ggttctttcg gtaccccctag aatcttgttt | 1440 |
| caatctggta ttggtccaac tgacatgatt caaaccgttc aatccaaccc aactgccgct | 1500 |
| gctaacttgc caccacaatc tgaatggatt aacttgccag ttggtcaagg tgtttccgac | 1560 |
| aacccatcta ttaacttggt tttcacccca ccatccatcg acgcttacga aaactgggct | 1620 |
| gacgtttggt ccaacccaag accagctgac gctcaacaat acttgcaatc cagatctggt | 1680 |
| gttttcgctg gtgcttcccc aaagttgaac ttctggagag cttacggtgg ttccgacggt | 1740 |
| aagaccagat atgctcaagg tactgttaga ccaggtgctg cctccgtcaa cacttccgtt | 1800 |
| gcttacaacg cctcccaaat tttccaccatc accgtttact tatctgaagg tattacctcc | 1860 |
| agaggtagat ggggtgtcga cgcagctttg aacatgaaag ctattactac cccatggttg | 1920 |
| accgatccag ttgacaagac tattttgttg caagcttttgc acgacgttgt ttccaacatc | 1980 |
| aacaacgtcc ctggtttgac cttgattacc cccgatcaca cccaaacttt ggaacaatac | 2040 |

```
gttgctgctt acgacccagc taccatgtgc tctaaccact gggtcggtgc tgccaagatc   2100
ggttcctccc catctactgc tgttgttgac gaaaacacca aggttttaa caccgacaac    2160 ttattcattg ttgacgcttc tattatccca tccttgccag tcggtaaccc tcacggtgct   2220
ttgatgtctg ccgctgaaca agctgccgct aagatcttgg ctttggctgg tggtccagaa   2280
caaaagttga tttctgaaga ggatttgtga taa                                2313

<210> SEQ ID NO 54
<211> LENGTH: 1566
<212> TYPE: DNA
<213> ORGANISM: Artificial Sequence
<220> FEATURE:
<223> OTHER INFORMATION: Codon Optimized

<400> SEQUENCE: 54
tacccatacg acgttcctga ttacgctact aactctggta ttggtccagt taccgacttg     60
agaatctcca acgccgttgt ctctccagac ggtttttctc gtgacgccgt cgttgtccaa    120
ggtcaattcc catccccatt aatcaagggt aacaaggggt acatgtttaa gttgaacgtc    180
attaaccaat acaagatact gccttaaac acttctactt ccatccactg gcatggtttg     240
ttccaacacg gtaccaactg gctgacggt ccagctttcg tgactcaatg tccaatcgtc     300
accggtgatt ccttcgttta cgacttcact gttccagacc aagctggtac cttctggtac    360
cactcccact tggctttaca atactgtgat ggtttgagag gtccattggt cgtttacgac    420
ccacacgatc catacgctca cttatacgac gtcgatgacg aatctactgt tattacttta    480
gccgaatggt accacactgc tgccgacaac ttacgtccac cagaagaagc taactccact    540 tgatcaacg gtttaggtag atacgctggt ggtccagcct ctccattgtc cgttatcact     600
gttgaacacg gtaagagata cagattcaga ctggttagta tggcttgtga cccttcctac    660
aacttcacta tcgacggtca acatgacc gttattgaag tcgacggtgt caaccacttg     720
ccattgactg ttgacaagat ccaaattttt gttgctcaaa gatactcttt catcttggat    780
gctaaccaac caattggtaa ctactggatc catgctatcc caaacggtca atctcaattg    840
gttggtgtcg ctaacggtat caactccgcc atcttgagat acgttggtgc tccaaacaag    900
gaaccaacta ctcaaacccc accatccgtt gccccattgc aagaagtcaa cttacaccca    960
ttggttaacg ctgccgctcc tggtaagcca ttcccaggtg gtgctgacca agtcatccca    1020
ttcaacttgt cttttgttggg tgctaacttc ttgatcaaca cgctactttt ctcccctcca   1080
accgttccag ttttgttgca atcttgtct ggtgctaaga ctcctcaaca attgttgcca     1140
ccaggttcta tctactcctt gaagagaaac tctgttattg aaatcgtcat tccaccaggt    1200
accgctccag gtggtccaca cccttttccac ttgcacggtc acactttctc tgtcgttaga    1260
tccgctggtt cttctgttta caactttaag aacccagttc aacgcgacgt tgtttccatc    1320
ggtactggtg ctaacgattc cgttaccatc agattcgtta ctgacaaccc aggtccatgg    1380
ttcatccact gtcacatcga cttccacttg aacgctggtt tggctgctgt tatggctgag    1440
gacattccag acattaagtt ggctaaccct gttccagccg aatgggaaca attgtgtcca    1500
atttacgacc aaaaggtctt gcatgaacac gaacaaaagt tgatttctga agaggatttg    1560
tgataa                                                              1566

<210> SEQ ID NO 55
<211> LENGTH: 1602
<212> TYPE: DNA
<213> ORGANISM: Artificial Sequence
```

<220> FEATURE:
<223> OTHER INFORMATION: Codon Optimized

<400> SEQUENCE: 55

```
tacccatacg acgttcctga ttacgcttct attggtccaa gaggtacctt gaacatcgct      60
aacgaagtta ttaagccaga tggtttcagc agatccgctg tcttggccgg tggtagttac     120
ccaggtccat tgatcaaggg tgaaactggt gacagattcc aaattaacgt cgtcaacaag     180
ttggctgaca cttcaatgcc tgtcgatact tctatccatt ggcacggtat ttttgttaga     240
ggtcacaact gggccgacgg tccagctatg gtcacccaat gtccaatcgt cccaggtcac     300
tccttcttgt acgactttga aattccgat caagccggta ctttctggta ccactctcac     360
ttgggtaccc aatactgtga cggtttgaga ggtccattcg ttgtctactc caagaacgac     420
ccacacaaaa gattgtacga tgtcgacgac gaatctactg tcctaaccgt tggtgactgg     480
tatcacgctc cttctttgtc cttgtctggt gtcccacacc cagactccac tttgttcaac     540
ggtttgggta gatccttgaa cggtccagcc tccccattat acgtcatgaa cgttgtcaag     600
ggtaagagat acagaatcag attgattaac acttcttgtg attctaatta ccaattttcc     660
attgacggtc acgctttcac tgtcatcgaa gctgatggtg aaaacaccca accattgcaa     720
gtcgaccaag tccaaatctt cgctggtcaa cgttactcct tggttttgaa cgctaaccaa     780
gctgttggta actactggat cagagctaac ccaaactctg gtgatccagg tttcgctaac     840
caaatgaact ccgctatctt gagatacaag ggcgctagaa acgttgaccc tactacccca     900
gaaagaaacg ctactaaccc attgagagaa tacaacttgc gtccattgat caaggaacca     960
gctccaggta accattccc aggtggtgct gatcacaaca tcaacctaaa ctttgccttc    1020
gacccagcta ccgttttatt cactgctaac aactatacct tgtcccacc tactgttcca    1080
gttctgttgc aaattttgtc tggtactcgt gatgcccatg atttggctcc agctggtagt    1140
atctacgaca tcaagtttggg tgacgtcgtt gaagttacta tgccagcctt ggttttcgct    1200
ggtccacacc caatgcattt gcacggccac tcctttgccg tcgttcgttc tgctggttcc    1260
tccacctaca actacgaaaa cccagtcaga cgtgatgttg tttcaattgg tgacgatcca    1320
actgataacg ttactatcag attcgtcgct gacaacgctg tccatggtt cttgcactgt    1380
cacatcgact ggcacttgga cttgggtttt gctgtcgtct ttgctgaagg tgttaaccaa    1440
accgctgtcg ctaacccagt ccctgaagct tggaacgatc tttgtccaat ctacaactct    1500
tccaacccat ccaaattgtt gatgggtact aacgctattg gtagattgca cgccccattg    1560
aaggctgaac aaaagttgat ttctgaagag gatttgtgat aa                      1602
```

<210> SEQ ID NO 56
<211> LENGTH: 1557
<212> TYPE: DNA
<213> ORGANISM: Artificial Sequence
<220> FEATURE:
<223> OTHER INFORMATION: Codon Optimized

<400> SEQUENCE: 56

```
tacccatacg acgttcctga ttacgctgcc atcggtccag ttaccgattt ggaaattact      60
gacgcttttg tttcacctga cggtccaggt ttgggtagaa agctgttttt ggccggtggt     120
acctttccag gtcccttaat ccaaggtaac aagggtgata cttccaaat caacgttgtc     180
aacaacttga ccaaccacac catgttgaaa accacctcca ttcactggca cggtttgttt     240
caacacggta ctacctgggc cgacggtcct gctttcgttt ctcaatgtcc aattgcttct     300
```

```
ggtaactcct tcttgtacaa cttcaacgtc ccagatcaag ccggtacctt ctggtaccat    360
tctcacttgg ctactcaata ctgtgacggc ttgagaggtc ctttggttgt ctacgaccca    420
aacgacccac acgctgactt gtacgatgtt gacgatgaat ccaccgtcat caccttgtcc    480
gactggtacc acgccgccgc ttctaccttg actttcccaa cctttgatac caccctaatt    540
aacggtttgg gtagattcgc tggtaccggt ggtagtgact ctaacttgac cgttatcact    600
gtcgaacaag gtaagagata cagattcaga ttagtttcta tttcttgtga tccaaactgg    660
gtctttagta tcgatcaaca cgaattgacc gttattgaag ttgacggtgt taacgccgtt    720
cctttgaccg tcgatgctat tcaaatcttc gccgctcaaa gatactccct cgttttgaac    780
gccaaccaaa ctgttgataa ctactggatc agagctaacc caaataacgg taacatgggt    840
ttcgctaacg gtatcaactc tgctatcttg agatacgttg gtgccgatga cgtcgaacca    900
acttctaccg gtactactgc taacttgttg aacgaagctg acttgtcccc attggttcct    960
gctgccgctc caggtgcccc aaaccaggac ttcgatgccg ttgatgttcc tatgaacttg   1020
aacttcacct tcaacggtac taacttgttc attaacggtg ctactttcgt tccaccatcc   1080
gttcctgttt tgactcaaat tttgtctggt gccatgactg ctcaagaatt gttgccagcc   1140
ggttccgttt acaccttacc aagaaacgct accgttcaat gtccttgcc tggtaacatc   1200
attgctggtc acacccttt ccacttgcac ggtcatacct tctctgtcat tagatccgct   1260
ggtcaatctg actacaacta cgtcgatcca attcaaagag atgtcgtttc cattggtggt   1320
gctactgaca acgttaccat tagattcact accgataacc caggtccatg gttcttccac   1380
tgtcacattg attggcattt gcaagctggt ttcgctatcg tttttgctga agaaactgcc   1440
gacgttgctt ccgctaaccc agttccagct gactggtctg ccttgtgtcc aacctacgat   1500
gctttgtctg acgctgacca cgaacaaaag ttgatttctg aagaggattt gtgataa    1557

<210> SEQ ID NO 57
<211> LENGTH: 1602
<212> TYPE: DNA
<213> ORGANISM: Artificial Sequence
<220> FEATURE:
<223> OTHER INFORMATION: Codon Optimized

<400> SEQUENCE: 57
tacccatacg acgttcctga ttacgcttct atcggtccaa gaggtacctt gaacatcgcc     60
aacaaggtca ttcaaccaga cggtttctac agatctactg tcttggctgg tggttcttac    120
ccaggtccat tgattaaggg taagactggt gatagattcc aaatcaacgt cgtcaacaag    180
ttggctgaca cttccatgcc agttgacact tccattcatt ggcacggttt gttcgtcaag    240
ggtcacaatt gggctgacgg tccagctatg gtcacccaat gtccaatcgt tcctggtcac    300
tcttctcttgt acgatttcga agttccagac caagccggta ctttctggta ccactcccac    360
ttgggtactc aatactgcga cggttttgaga ggtccattgg tcgtttacag caaaaacgat    420
ccacacaagc gtttgtacga tgttgacgat gaatctaccg ttttgactgt cggtgactgg    480
taccacgctc catccttgtc tttgaccggt gttccacacc cagactccac cctatttaac    540
ggttgggta gatctttgaa cggtccagct tccccattgt acgtcatgaa cgtcgttaag    600
ggtaagagat acagaatcag acttatcaac acttcctgtg actccaacta ccaattctct    660
attgacggtc acaccttcac tgttatcgaa gctgacggtg aaaacactca accattgcaa    720
gttgatcaag ttcaaatctt cgccggtcaa agatactctt tggttttgaa cgctaaccaa    780
gctgttggta actactggat cagagctaac ccaaactctg gtgacccagg cttcgaaaac    840
```

```
caaatgaact ccgctatttt gagatacaag ggtgctagat ctatcgatcc aaccactcca      900
gaacaaaacg ctaccaaccc actacacgaa tacaaccttc gtccgttgat caagaaacca      960
gctccaggta agccattccc tggcggtgct gatcataaca ttaatttgaa cttcgctttc     1020
gacccagcta ccgctttgtt cactgctaac aaccacactt tcgtcccacc aaccgttcca     1080
gttttattgc aaattttgtc cggtactcgc gacgcccatg acttggcccc agctggttct     1140
atttacgata ttaagttggg tgatgtcgtt gaaatcacca tgccagcttt ggttttcgct     1200
ggtccacacc caatccactt gcatggtcac accttcgccg ttgttagatc cgccggttcc     1260
tctacttaca actacgaaaa cccagtccgt cgtgatgtag tttccattgg tgacgaccca     1320
actgacaacg ttaccattag attcgtcgct gacaacgcag gtccatggtt cttgcactgt     1380
catatcgact ggcacttgga cttgggtttt gccgttgtct ttgctgaagg tgttaaccaa     1440
actgctgctg ctaacccagt tccagaagcc tggaataact tgtgtccaat tacaactct      1500
tccaacccat ctaagttgtt gatgggtact aacgctattg gtagattgcc agctccattg     1560
aaggctgaac aaaagttgat ttctgaagag gatttgtgat aa                        1602
```

<210> SEQ ID NO 58
<211> LENGTH: 1581
<212> TYPE: DNA
<213> ORGANISM: Artificial Sequence
<220> FEATURE:
<223> OTHER INFORMATION: Codon Optimized

<400> SEQUENCE: 58

```
tacccatacg acgttcctga ttacgctgct atcggtccaa ccggtgacat gtacattgtt       60
aacgaggatg tttccccaga cggtttcacc cgttccgctg tcgtcgccag atctgatcca      120
accactaacg gtaccagcga aactttgacg ggtgttttgg ttcaaggtaa caagggtgac      180
aactttcaat tgaacgtttt gaaccaattg tccgacacca ctatgttaaa gaccacctct      240
atccattggc atggtttctt ccaatctggt tccacttggg ctgatggtcc agctttcgtc      300
aaccagtgcc caatcgcttc tggtaactcc ttcttgtacg actttaacgt tccagaccaa      360
gctggtactt tctggtatca ctcccacttg tccacccaat actgtgacgg tttgagaggt      420
ccattcattg tttacgaccc atctgatcca cacttgtctt tgtacgacgt tgataacgct      480
gacaccatca tcactttgga agattggtac acgtcgttg ctccacaaaa cgctgtcttg      540
ccaaccgctg actctacttt tgatcaatggt aagggtagat cgccggtgg tccaacctct      600
gctttggccg ttattaacgt cgaatccaac aagagataca gattcagatt gatctctatg      660
tcctgcgatc caaactttac cttctccatt gacggtcact ccttgcaggt tatcgaagct      720
gacgccgtta acattgttcc aattgtcgtt gactccatcc aaatcttcgc tggtcaaaga      780
tactctttcg tcttgaacgc caaccaaact gttgacaact actggatcag agctgaccca      840
aacttgggtt ccaccggttt cgacggtggt attaactctg ccattttgag atacgccggc      900
gctaccgagg atgaccctac caccacttcc tctacctcca ctccattgga agaaaccaac      960
ttggttccat ggaaaaccc tggtgctccc ggtccagccg ttccaggtgg tgctgacatt     1020
aacatcaact tggccatggc tttcgatgtc accaacttcg aattgaccat caacggttct     1080
ccattcaagg ctcctaccgc cccagtcttg ttgcaaatct gtctggtgc taccaccgct     1140
gctagtttgt tgccatccgg ttctatctac tccttggaag ccaacaaggt tgtcgaaatc     1200
tccatcccag ctttggctgt tggtggtcct caccccattcc atttgcacgg tcacactttc     1260
```

```
gacgtcatca gatccgctgg ttctaccacc tacaacttcg acaccccgc tagaagagat      1320 gttgttaaca ctggtaccga cgctaacgac aatgttacca tcagattcgt taccgataac     1380
cctggtcctt ggttttgca ctgtcacatc gattggcact tggaaatcgg tttggctgtc      1440 gttttgctg aagatgttac ctccattact gctccaccag ccgcttggga cgatttgtgc      1500
ccaatctacg acgctttgtc tgattctgac aagggtggta ttgctgaaca aaagttgatt    1560
tctgaagagg atttgtgata a                                                1581

<210> SEQ ID NO 59
<211> LENGTH: 1593
<212> TYPE: DNA
<213> ORGANISM: Artificial Sequence
<220> FEATURE:
<223> OTHER INFORMATION: Codon Optimized

<400> SEQUENCE: 59
tacccatacg acgttcctga ttacgctgct attggtccag ctggtaacat gtacattgtc       60
aacgaagatg tttctccaga cggtttcgcc cgttctgctg ttgttgctag atctgttcca      120
gctaccgatc caaccccagc taccgcttct atcccaggtg tcttggttca aggtaacaag      180
ggtgataact ccaattgaa cgtcgttaac caattgtctg ataccactat gttaaaaact      240
acttctattc attggcacgg tttctttcaa gcgggcagta gttgggctga tggtccagct      300
ttcgtcaccc aatgtccagt cgcttccggt gattccttct tgtacaactt caacgttcca      360
gaccaagccg tactttttg gtaccactcc catttgtcca cccaatactg tgacggtttg      420
cgtggtccat tcgtcgttta cgatccatct gacccacatt tgtctttgta cgacatcgac      480
aacgccgata ctgtcattac cttggaggat tggtaccaca tgttgctcc acaaaacgct      540 gctatcccta ctccagattc caccttgatt aacggtaagg tcgttacgc cggcggtcct      600 acttccccat tggctatcat taacgttgaa tctaacaaga gatacagatt cagattggtt      660
tctatgtcct gtgacccaaa cttcaccttc agtatcgatg ccactctttt gctagtcatc      720
gaagccgacg ctgttaacat cgtcccaatt actgttgact ctatccaaat ttttgctggt      780
caaagatact ccttcgtttt gaccgctaac caagccgtcg ataactactg gattcgtgct      840
aacccaaact ggggttctac cggtttcgtt ggtggtatca actccgctat ttttgcgttac     900 gctggtgcca ccgaagatga cccaaccacc acctcttcca cctctacccc attgttggaa      960
accaacttag tcccattgga aaacccaggt gctccaggtc cacctgttcc aggtggtgct     1020
gatatcaaca ttaacttggc catggctttc gatttcacca ccttcgaatt gactattaac    1080
ggtgtcccat tcttaccacc aaccgctcct gttttgttgc aaattttgtc tggtgcttcc    1140
actgctgctt ccttgttgcc atccggttcc atctacgaat ggaagctaa caaggttgtc    1200 gaaatctcta tgccagccct ggctgtcggt ggtccacacc cattccactt gcatggtcac    1260
accttcgacg ttattagatc cgctggttct accacctaca acttcgacac cccagctaga    1320
cgtgatgtcg ttaacactgg tactggtgct aacgacaacg tgaccatcag attcgttact    1380
gacaacccag gtccatggtt cttgcactgt cacatcgact ggcatttgga aatcggtttg    1440
gccgttgttt cgctgaaga tgttacctct atttctgccc caccagctgc ttgggacgac     1500
ttgtgtccca tctacaacgc cttgtcagac aacgataagg gtggtattgt tccatcggaa    1560
caaaagttga tttctgaaga ggatttgtga taa                                  1593

<210> SEQ ID NO 60
<211> LENGTH: 1557
```

<212> TYPE: DNA
<213> ORGANISM: Artificial Sequence
<220> FEATURE:
<223> OTHER INFORMATION: Codon Optimized

<400> SEQUENCE: 60

```
tacccatacg acgttcctga ttacgctgcc atcggtcccg ttactgactt gaccatctct    60
aacgctgatg tcagtccaga cggtttcacc agagctgctg tcttggccaa cggtgttttc   120
ccaggtccat tgattactgg caacaaaggt gacaacttcc aaatcaacgt cattgataac   180
ttgtctaacg aaaccatgtt aaagtctact tctatccact ggcacggttt cttccaaaag   240
ggtactaact gggccgacgg tgctgctttc gtcaaccaat gtccaattgc taccggtaac   300
tctttcttat acgacttcac tgctaccgat caagctggta ccttctggta ccactcccac   360
ttgtctactc aatactgtga cggtttgaga ggtccaatgg tcgtttacga tccatccgac   420
ccacatgctg acttatacga tgttgacgat gaaactacta ttatcacttt gtccgactgg   480
taccacaccg ctgcttctct tggtgctgct tcccaattg ttccgattc cacttgatc     540
aacggtttag gtagattcgc cggtggtgac tccactgact ggctgttat tactgtcgaa    600
caaggtaaga gatacagaat gagattgtta tctttgtctt gtgacccaaa ctacgttttc   660
tctatcgacg gtcacaacat gaccattatc gaagctgacg ctgtcaacca cgaaccattg   720
accgtcgatt ccatccaaat ttacgctggg caaagatatt ccttcgtttt gactgctgac   780
caagatatcg acaattactt catccgtgct ttaccttctg ctggtaccac ctctttcgac   840
ggtggtatca actctgctat tttgagatac tccggtgcct ccgaagtcga cccaactact   900
actgaaacca cttctgtttt gccattggac gaagctaact tagtcccatt ggattctcca   960
gccgccccgg tgacccaaa tattggtggt gtcgactacg ctttgaactt ggatttcaac  1020
tttgacggta ctaacttctt catcaacgac gtttctttcg tttctccaac cgttccagtc  1080
ttgttgcaaa ttttatccgg tactacctcc gctgctgact gttgccttc tggttctttg  1140
ttcgctttgc catctaactc caccatcgaa atttccttcc caatcactgc taccaacgcc  1200
ccaggtgccc cacatccatt ccatttacac ggtcacactt tctctattgt cagaaccgct  1260
ggttccactg atactaactt cgttaaccca gtcagacgag atgtcgttaa caccggtacc  1320
gccggtgata cgtcaccat cagattcact accgacaacc caggtccatg gttcttgcac  1380
tgtcacatcg acttccactt ggaagccggt tttgctattg ttttctctga agataccgcc  1440
gatgtttcca acactactac cccttctact gcttgggaag atttgtgtcc aacttacaac  1500
gctttagatt cttctgactt ggaacaaaag ttgatttctg aagaggattt gtgataa    1557
```

<210> SEQ ID NO 61
<211> LENGTH: 1560
<212> TYPE: DNA
<213> ORGANISM: Artificial Sequence
<220> FEATURE:
<223> OTHER INFORMATION: Codon Optimized

<400> SEQUENCE: 61

```
tacccatacg acgttcctga ttacgctggt attggtccag ttgctgactt gaccattact    60
aacgctgcgg tcagccctga tggtttctcc agacaagctg ttgttgtcaa cggtggtacc   120
ccaggtccat tgatcactgg taacatgggt gacagatttc aattgaacgt tatcgataac   180
ttaaccgacc acactatgtt gaagtctact tctatccact ggcacggttt cttccaaaag   240
ggtaccaact gggccgatgg tccagctttt attaatcaat gcccaatctc ttctggtcac   300
```

```
tccttcttgt acgacttcca agttccagat caagctggta cgttttggta ccactcccac    360
ttgtctaccc aatactgtga cggtttaaga ggtccattcg ttgtttacga cccaaacgat    420
ccagccgctg acttgtacga cgtggacaac gacgataccg ttattacctt agccgactgg    480
taccacgttc tgctaagttg ggtccagctt tttccattgg gtgccgacgc cactttgatc    540
aacggtaagg gtagatcccc atctaccacc accgctgatt tgactgtcat ctctgttacc    600
ccaggtaaga gatacagatt cagattggtt tccttgtcct gtgacccaaa ccacactttc    660
tctattgacg gtcacaacat gaccattatc gaaactgact ccatcaacac tgcccctttg    720
gtcgttgact caattcaaat cttcgctgct caaagatact ccttcgtctt ggaagctaat    780
caagctgttg ataactactg gattcgtgct aacccatcct tggtaacgt cggtttcacc     840 ggtggtatca actctgccat tttgagatac gacggtgctg ccgctattga accaactacc    900
acccaaacta cctctactga accattgaac gaagttaact acacccatt agttgccacc     960 gctgttccag ttctccagc cgctggtggt gtcgatttgg ctattaacat ggctttcaat    1020
ttcaacggta ctaacttctt tatcaacggt gcttccttca cccctccaac cgttccagtt   1080
ttgttgcaaa ttatttccgg tgcccaaaac gcccaagact tattgccatc tggttccgtc    1140
tactctttgc catctaacgc tgatatcgaa atctctttcc cagccactgc tgctgccca     1200 ggcgccccac atccattcca cttgcacggt cacgctttcg ctgttgttag atccgctggt    1260
tccaccgtct acaactacga caacccaatc ttcagagatg ttgtttctac tggtaccca    1320 gctgccggtg acaatgtcac cattagattc agaaccgata acccaggtcc atggttttg    1380 cattgtcaca tcgatttcca cttggaagcc ggtttcgctg ttgttttgc cgaagatatt    1440 cctgacgttg cttctgctaa cccagttcca caagcttgga gcgacttgtg tccaacttac    1500
gatgcccgag atccatctga ccaagaacaa aagttgattt ctgaagagga tttgtgataa   1560
```

<210> SEQ ID NO 62
<211> LENGTH: 1560
<212> TYPE: DNA
<213> ORGANISM: Artificial Sequence
<220> FEATURE:
<223> OTHER INFORMATION: Codon Optimized

<400> SEQUENCE: 62

```
tacccatacg acgttcctga ttacgctgct atcggtccag ttgcttcttt ggttgtcgcc     60
aacgccccag tttccccaga tggtttctta agagatgcta ttgttgttaa cggtgttgtt    120
ccatccccat tgatcactgg taagaagggg gacagatttc aattgaacgt cgttgacact    180
ttgactaacc attccatgtt gaagtccacc tctattcact ggcacggttt tttccaagcc    240
ggtaccaact gggctgacgg tccagccttc gtcaaccaat gtccaatcgc ctctggtcat    300
tccttcttgt acgatttcca cgttccagat caagctggta ctttctggta ccactctcac    360
ttatctactc aatactgtga cggtttgaga ggtccattcg ttgtttacga cccaaaggac    420
ccccacgctt ccagatacga tgtcgacaac gaatccactg ttattacttt gactgactgg    480
taccataccg ctgctagatt gggtccaaga tttccattgg gtgctgacgc cactttgatc    540
aacggtttgg gtcgttccgc ttctacccca accgctgcct ggctgtcat taacgttcaa    600 cacggtaaga gataccgttt cagattagtt tccatttctt gtgatccaaa ctacactttc    660
tctatcgacg gtcacaactt gactgttatt gaagttgacg gtattaacag ccaaccattg    720
ttggttgact ccatccaaat cttcgctgcc caaagatact ccttcgtttt gaacgctaac    780
caaaccgttg gtaactactg ggtcagagct aacccaaact tcggtactgt tggttttgcc    840
```

```
ggtggtatta actctgctat tttgagatac caaggtgccc cagttgctga gccaaccact      900
acccaaactc catctgtcat tcctttaatc gaaaccaact tgcacccatt ggccagaatg      960
ccagttccag gtagcccaac tccaggtggt gtcgacaagg ctttgaactt agccttcaac     1020
ttcaacggta ctaactttt cattgacaac gcctccttta ctccaccaac tgtcccagtc     1080
ttgttgcaaa tcttgtccgg tgctcaaacc gctcaagaat tgttgccagc cggttccgtt     1140
tacccattgc cagcccattc taccatcgaa attacttta ctgctactgc tttagctcca      1200
ggtgctccac acccattcca cttgcacggt cacgccttcg ctgttgttag atctgctggt     1260
tctaccacct acaactacaa cgatccaatc ttccgtgacg ttgtctctac cggtactcca     1320
gctgctggtg acaacgttac tattagattc caaactgaca acccaggtcc ttggttcttg     1380
cattgtcaca ttgatttcca tttggaagcc ggtttcgcta tcgttttcgc tgaggacgtt     1440
gctgatgtta aggctgctaa cccagttccc aaggcttggt ctgacttgtg tcctatctac     1500
gacggtttgt ccgaagccaa ccaagaacaa aagttgattt ctgaagagga tttgtgataa     1560
```

<210> SEQ ID NO 63
<211> LENGTH: 1575
<212> TYPE: DNA
<213> ORGANISM: Artificial Sequence
<220> FEATURE:
<223> OTHER INFORMATION: Codon Optimized

<400> SEQUENCE: 63

```
tacccatacg acgttcctga ttacgctgct attggtccag tcactgactt gaccatctct       60
aacgccgatg tcactcctga cggtatcacc agagctgccg ttttggctgg tggtgttttt      120
ccaggtccat tgatcacggg caacaagggt gatgaattcc aaattaacgt catcgacaac      180
ttgaccaacg aaaccatgtt aaagtctacc accatccact ggcatggtat ctttcaagct      240
ggtaccaatt gggctgacgg tgctgctttc gttaaccaat gtccaatcgc cactggtaac      300
tccttcttgt acgacttcac tgtcccagat caagccggta ccttctggta ccactctcac      360
ttgtccaccc aatactgcga cggttttgaga ggtccattgg tcgtctacga cccagatgac      420
gccaatgctt ctctatatga cgtcgatgac gatactaccg ttatcacttt ggccgactgg      480
taccacactg ccgctaagtt gggtcctgcc ttcccagcag gtccagattc cgtcttaatc      540
aacggttggg gtagattctc tggtgatggt ggtggtgcca ccaacttgac cgttatcacc      600
gtcactcaag gtaagcgtta cagattcaga ttggtttcca tctcttgtga cccaaacttc      660
actttcagca ttgatggtca aacatgacc atcattgaag ttggtggtgt taaccatgaa      720
gctttggacg ttgattccat ccaaattttc gctggtcaaa gatactcttt catcttgaac      780
gccaaccaat ccatcgataa ctactggatt cgtgctatcc aaacactgg taccactgat      840 actactggtg gcgtcaactc cgccatcttg agatatgata ccgccgaaga aattgaacca      900
accaccaacg ctaccacctc tgttatccca ttaactgaaa ccgacttggt cccattagac      960
aacccagccg ccccaggtga tccacaagtc ggtggtgttg acttggccat gtccttggat     1020 tttttctttca acggttctaa cttcttcatc aacaacgaaa cctttgttcc acccaccgtc     1080
ccagttttgt tgcaaatctt gtccggtgct caagacgccg cttccttgtt gcctaatggt     1140
tctgtctaca ctttgccatc caacagcacc atcgaaatct cttttcccaat catcaccacc     1200 gacggtgcct tgaacgctcc aggtgcccca caccccattcc acttgcacgg tcacactttc     1260
tctgttgtta gatctgccgg ttcctctact ttcaactacg ctaacccagt cagaagagac     1320
```

```
accgttttcca ccggtaactc tggtgacaac gtcactatca gatttaccac tgacaaccca   1380
ggtccatggt tcttacactg tcacatcgat ttccacttgg acgccggttt cgctatcgtt   1440
tttgctgaag ataccgctga cactgcttcc gctaacccag ttccaaccgc tggtccgac    1500 ttgtgtccaa cttacgacgc cttggattcc tccgacttgg aacaaaagtt gatttctgaa   1560
gaggatttgt gataa                                                   1575
```

<210> SEQ ID NO 64
<211> LENGTH: 1560
<212> TYPE: DNA
<213> ORGANISM: Artificial Sequence
<220> FEATURE:
<223> OTHER INFORMATION: Codon Optimized

<400> SEQUENCE: 64

```
tacccatacg acgttcctga ttacgctgct atcggtccaa ctgctgattt gaccatttct     60
aacgctgaag tctccccaga cggtttcgct agacaagctg ttgtcgtcaa caacgttact    120
ccaggtccat tggttgctgg taacaaaggt gacagattcc aattgaatgt tatcgataac    180
ttgaccaacc acaccatgtt gaagtcaact tctatccact ggcacggttt cttccaaaag    240
ggtaccaact gggctgatgg tccagctttc gtcaaccaat gtccaatctc ctctggtcac    300
tccttcttgt acgacttcca agtcccagat caagctggta ccttctggta ccactctcac    360
ttgtccactc aatactgtga cggtttgaga ggtcccttcg tcgtttacga tcccaacgac    420
ccacatgctt ccttgtacga cgttgacaac gatgacaccg tcatcacctt ggccgactgg    480
taccacactg ctgctaaatt gggtccagct ttccctttgg gtgccgacgc taccttgatc    540
aacggtttag gtagaagtcc atctactacc gctgctgact tggccgttat caatgtcacc    600
aagggtaaga gatacagatt tagattggtc agcttgtcct cgacccaaa ccacactttc     660 agcattgatg gtcacgactt gaccatcatc gaagttgatt ctatcaacag ccaaccattg    720
gtcgtcgact ccatccaaat cttcgctgcc aacgttact ccttcgtctt gaacgctgat     780
caagacgttg gtaactattg gattagagct aacccaaact tcggtaacgt cggtttcgcc    840
ggtggtatca actctgctat tttgagatac gacggtgccg atccagttga accaaccacc    900
actcaaacca ctccaaccaa gccattgaac gaagtcgact tgcacccatt ggctactatg    960
gccgtcccag ctccccagt tgcgggtggt gtcgacaccg ctatcaacat ggcttttaac    1020
ttcaacggta ctaatttctt cattaacggt gcttctttcg tcccacctac cgtcccagtt   1080
ttgttgcaaa tcatttctgg tgctcaaaac gctcaagact tgttgccaag tggttctgtc   1140
tactccttgc caagtaacgc tgacatcgaa atttccttcc cagccaccgc tgctgctcca   1200
ggtgccccac acccattcca cttgcacggt cacgctttcg ccgttgttag atctgctggt   1260
tccactgttt acaactacga taacccaatc ttccgtgatg tagtttctac cggtaccct   1320 gccgctggtg ataacgtcac tattagattc cgtactgaca cccaggtcc atggttcttg    1380 cactgtcaca tcgatttcca cttggaagct ggtttcgctg tcgtctttgc tgaggacatt   1440
cccgatgttg ccagcgctaa cccagtccca aagcttggt ctgacttatg tccaatctac    1500
gacgctttgg acgttaacga ccaagaacaa aagttgattt ctgaagagga tttgtgataa   1560
```

<210> SEQ ID NO 65
<211> LENGTH: 1554
<212> TYPE: DNA
<213> ORGANISM: Artificial Sequence
<220> FEATURE:
<223> OTHER INFORMATION: Codon Optimized

<400> SEQUENCE: 65

```
tacccatacg acgttcctga ttacgctgct atcggtccag tcgctgactt gactttgacc    60
aacgctgctg tttctccaga cggtttctcc agagaagctg ttgttgtcaa cggtattact   120
ccagctccat tgatcgccgg tcaaaagggt gacagattc aattgaacgt catcgacaac    180
ttgaccaacc acactatgtt aaaaaccacc tccatccact ggcacggttt cttccaacac   240
ggtaccaact gggccgacgg tgtttctttc gtcaaccaat gtccaatcgc ttccggtcac   300
tctttcttat acgatttcca agttccagac caagctggta ctttctggta ccactctcac   360
ttgtctaccc aatactgtga tggtttgaga ggtccattcg tcgtttacga cccaaacgat   420
ccacaagctt ctttgtatga tattgacaac gatgatactg ttattacctt ggccgactgg   480
taccacgtcg ctgctaagtt gggtccaaga ttcccattgg gtgctgatgc aaccttgatc   540
aacggtttgg gtagatcccc aggtaccacc actgctgact ggctgttat caaggttact     600
caaggtaaga gatacagatt cagattggtt tctttgtcct gtgatccaaa tcacaccttc   660
tccattgacg gtcacactat gaccgtcatc gaagccgact ctgttaacac tcaaccattg   720
gaagttgact ctatccaaat cttcgctgct caaagatact ccttcgtttt ggacgcctcc   780
caaccagtcg ataactactg gatcagagct aacccagctt tcggtaacgt tggtttcgct   840
ggtggtatca actccgccat tttgcgttac gacggtgccc cagaagttga accaaccacc   900
acccaaacta cttctaccaa gccattgaac gaagctgatt tgcatccatt gactccaatg   960
ccagtcccag gtagaccaga agctggtggt gttgacaagc cattgaacat ggtgttcaac  1020
ttcaacggta ccaacttctt cattaacaac cactccttcg ttccaccatc tgtcccagtt  1080
ttgttgcaaa tcttgtccgg tgcccaagct gctcaagatt tggttccaga cggttccgtc  1140
tacgtcttgc aagcaactc ttccatcgaa atttccttcc cagccactgc aaacgcccca    1200
ggtaccccac acccattcca tttgcatggt cacaccttcg ctgttgtcag atctgctggt  1260
tcctccgaat acaactacga caatcctatc ttccgtgacg ttgtttccac tggtcaacca  1320
ggtgataacg tcactatcag attccaaacc aacaacccag tccatggtt cttgcactgt   1380
cacatcgact ccacttgga agctggtttt gccgttgtct tggccgaaga tactccagac  1440
accgctgctg ttaacccagt cccacaatcc tggtccgact tgtgtccaat ttacgacgcc  1500
ttagacccat ctgacttgga acaaaagttg atttctgaag aggatttgtg ataa        1554
```

<210> SEQ ID NO 66
<211> LENGTH: 1818
<212> TYPE: DNA
<213> ORGANISM: Artificial Sequence
<220> FEATURE:
<223> OTHER INFORMATION: Codon Optimized

<400> SEQUENCE: 66

```
tacccatacg acgttcctga ttacgctaag gtcccaggta tggacatcaa gtacgacgtc    60
gttattgtcg gttccggtcc aatcggttgt acttacgcta gagaattggt tgaagctggt   120
tacaaagtcg ctatgttcga catcggcgaa atcgactctg gtttgaagat tggtgctcac   180
aagaaaaaca ctgttgaata ccaaaagaac atcgacaagt tgtcaacgt catccaaggt    240
caattgatgt ctgtctctgt tccagttaac acttagtca ttgacaccctt gtctccaact   300
tcctggcaag cttcctcttt cttcgttaga aacggttcta acccagaaca agacccatta   360
agaaacttgt ccggtcaagc tgtcactaga gttgtcggtg gtatgtctac tcactggacc   420
```

```
tgtgctactc cacgtttcga tagagaacaa agaccattgt tggtcaagga tgaccaagac    480
gctgatgacg ctgaatggga tagattgtac accaaggctg aatcatattt caagactggt    540
accgaccaat tcaaggaatc catcagacac aacttggtct tgaacaagtt ggctgaagaa    600
tacaagggtc aaagagactt ccaacaaatt ccattggctg ccactagaag atctccaacc    660
ttcgtcgaat ggtcaagtgc taacactgtt ttcgacttgc aaaacagacc aaacactgat    720
gctccaaacg aaagattcaa cttgtttcca gctgtcgctt gtgaaagagt tgttcgtaac    780
acttccaact ccgaaatcga atctttgcat atccacgact tgattagcgg tgacagattc    840
gaaatcaagg ctgacgtttt cgttttgact gctggtgctg ttcacaacgc ccaattgtta    900
gtcaactccg gtttcggtca attgggtaga ccagacccag ctaacccacc acaattgttg    960
ccctctttgg gttcttacat cactgaacaa tctttggtat tttgtcaaac cgttatgagc   1020
actgaattga tcgattccgt caagtctgac atgattatca gaggtaaccc aggtgacttg   1080
ggttactccg tcacctacac tccaggtgcc gaaactaaca agcatccaga ctggtggaac   1140
gaaaaagtta agaaccacat gatgcaacat caagaagatc cattgcctat cccattcgag   1200
gaccctgaac acaagttac accttattc aaccatctc acccatggca cacccaaatt   1260
caccgtgatg ccttctccta cggtgccgtc aacaatcaa tcgacagccg tttgatcgtc   1320
gactggagat tcttcggtag aactgaacca aggaagaaa acaaattgtg gttctccgat   1380
aaaattactg atacctacaa catgccacaa ccaactttcg acttcagatt cccagctggt   1440
agaacctcta aggaagctga agatatgatg actgacatgt gtgttatgtc tgccaagatc   1500
ggtggttttt tgccaggttc cttgccacaa ttcatggaac aggttttggt cttgcacttg   1560
ggtggtaccc atagaatggg tttcgacgaa caagaagata agtgttgtgt gaatactgac   1620
tccagagttt tcggtttcaa gaacttattc ttgggtggtt gtggtaacat cccaaccgct   1680
tacggtgcta accctacttt gactgctatg tccctagcta ttaaatcttg tgaatacatt   1740
aagaacaact tcaccccatc cccattcacc gatcaagctg aagaacaaaa gttgatttct   1800
gaagaggatt tgtgataa                                                 1818
```

<210> SEQ ID NO 67
<211> LENGTH: 1761
<212> TYPE: DNA
<213> ORGANISM: Artificial Sequence
<220> FEATURE:
<223> OTHER INFORMATION: Codon Optimized

<400> SEQUENCE: 67

```
tacccatacg acgttcctga ttacgctgcc gacttcgatt acgttgtcgt cggtgctggt     60
aacgccggta acgttgtcgc tgccagacta accgaggacc cagatgtctc tgtcttggtt    120
ttagaagctg gtgtttctga cgaaaacgtt ttgggtgctg aagctccatt gttggcccca    180
ggtttagtcc caaactctat cttcgattgg aactacacta ccaccgctca agctggttac    240
aacggtcgtt ccattgctta cccaagaggt agaatgttgg gtggttcttc ctctgtccac    300
tacatggtta tgatgagagg ttctaccgag gatttcgata gatacgccgc tgtcaccggt    360
gatgaaggtt ggaactggga caacatccaa caattcgtta gaaagaacga atggtcgtt    420 ccaccagctg acaaccacaa cacttccggt gaattcattc ccgctgttca cggtactaac    480
ggttctgtct ccatctcttt gccaggtttt cctaccccat ggatgacag agttttggcc    540 accacccaag aacaatccga agaattcttc ttcaacccag atatgggtac tgggcatcct    600
ttgggtatct catggtccat tgcttctgtc ggtaacggtc aaagatcctc ctcttctacc    660
```

```
gcctacttgc gtccagccca atccagacca aacttgtccg ttttgatcaa cgcccaagtc      720
accaagttgg tcaactccgg tactaccaac ggtttgcctg cttttagatg tgtcgaatac      780
gccgaacaag aaggtgctcc aactaccact gtctgtgcta agaaggaagt cgttttgtct      840
gctggttccg tcggtacccc aatcttgttg caattgtcag gtatcggtga tgaaaacgac      900
ttgtcaagtg tcggtattga caccatcgtc aacaacccat ctgttggtag aaacttgtct      960
gaccacttgt tgttgccagc cgctttcttc gtcaactcca accaaacttt cgataacatt     1020
tttcgtgact cttctgaatt caacgtcgac ttggaccaat ggaccaacac cagaaccggt     1080
ccattgactg ctttgatcgc taaccacttg gcttggttga gattgccttc caactctagt     1140
atcttccaaa ctttcccaga tccagccgct ggtccaaact ccgctcactg ggaaaccatc     1200
ttctctaacc aatggttcca cccagctatc ccaagaccag acactggttc cttcatgagc     1260
gttaccaacg ctttgatctc cccagtcgct agaggtgaca tcaagttggc cacctctaac     1320
ccattcgata agccattgat taacccacaa tacttgtcta ctgaattcga cattttacc      1380 atgattcaag ctgttaagtc taacttgaga ttcttgtctg gtcaagcctg gctgatttc      1440 gtcatcagac cattcgaccc aagattgcgt gacccaactg acgatgccgc catcgaatcc     1500
tacattagag ataacgctaa caccattttc cacccagtcg gtactgcttc tatgtctcca     1560
cgtggtgctt cttggggtgt cgtcgatcca gacttgaagg tcaagggtgt cgacggtttg     1620
agaattgttg acggttccat tttgccattc gctccaaacg ctcacaccca aggtccaatc     1680
tacttggtcg gtaagcaagg tgccgatttg atcaaggctg atcaagaaca aaagttgatt     1740
tctgaagagg atttgtgata a                                              1761
```

<210> SEQ ID NO 68
<211> LENGTH: 1764
<212> TYPE: DNA
<213> ORGANISM: Artificial Sequence
<220> FEATURE:
<223> OTHER INFORMATION: Codon Optimized

<400> SEQUENCE: 68

```
tacccatacg acgttcctga ttacgctaac tctttcgact acgttgtcgt tggtggtggt       60
accgccggcg ctgttatcgc taacagatta actgaaaacc caagagtcac tgttttattg      120
ttggaagctg tccatccaa cattaacgtt accaactcta tcgttccatt gttgcacaac       180
ttcttgattc caaacacccc atacgactgg aacttcacca cgactaacca agttggtttc      240
aacggtagaa acatcagctt cccacgtggt cacatgttgg gtggttcttc ttctgttaac      300
ggtttggttt tcaccagagg ttcctctgac gactgggatg cctacgctgc tattgctgaa      360
gatccatctt ggacctggga aaacatccaa cgttacttgc cattaattga acaattcacc      420
gaacctatcg aaccatacaa cattaccggt gatttcattc catccttgca cggtaccgac      480
ggtaaaatcc aaacctctgt tgccaactac agaatcccat ggacgagca catcatcgaa       540 gcttcccaag aattgggtga cgaattccca ttcaacccag atatgggtgg tgtgaaaat      600 gttttgggtt tgggttggac cgtcagtacc atcggtagag tgttagatc ttcttccgct       660 accggttact ggcccccaga atacttgtcc agaccaaact gcatgtcttt ggttcatgct     720
caagttacca agttgattca aaccggtacc agaaacagat tgccatcttt ccactccttg     780
caattcacgt ccaccttggc tgctcgtcca atcaccgtca ccggtcgtcg tgcggttgtt     840
ttgagcgctg gtgcagtcgg tactccacac attttgcaat tgtctgggat cggtgacaga    900
```

| | |
|---|---|
| tccttgttag aatccgttgg tattagaacc attgttcaca acccatctgt tggtagaaac | 960 |
| ttgtctgatc acccattgtt ggcttgtgtt tactcggtcc atgacaactc ttcttacgac | 1020 |
| atcttattca gagaaccagc tgttttcaa gccgctatgg accaatggaa cgctaaccac | 1080 |
| accggtccag gtgccgccag tgtctttaat caagttggtt tcttcagatt gccagacaac | 1140 |
| gctaccattt ttgaaaccac tccagaccca gcttccggtc caaagtccgg tcacttcgaa | 1200 |
| atcatgttct caaacttcta caacttacca ggtttggccg ctccaacctc tggtaccacc | 1260 |
| atctctttcg acgtcgctgt tattccagct acttccagag gttctgtcga attaacctct | 1320 |
| accgacccat cgctgctcc agctatcgac ccagcttacc tacaatccga attcgatatt | 1380 |
| ttcactatgt tggaagctgt taaggctgtc agaagattcg ccgaagctca aaccttcgac | 1440 |
| ggttacatca ttgaaccatt cggtgaattc ggtgctgcta ccactgatga attgttggaa | 1500 |
| accttcgcta gaggtaacgc cgccactgtt tttcacccag tcggtacctc ttccatgtct | 1560 |
| ccaaaaggtg ctaactgggg tgtcgttgac ccagatttga gagttaaggg tgttgaaggt | 1620 |
| ttgtttatca ttgacgctgg tgttatcaac aagttgccaa ccgcccacac catggctcca | 1680 |
| actttcatcg tcgctgaaag aggtgctgaa ttacttaagg ctttgaccga caaaagttg | 1740 |
| atttctgaag aggatttgtg ataa | 1764 |

<210> SEQ ID NO 69
<211> LENGTH: 1092
<212> TYPE: DNA
<213> ORGANISM: Artificial Sequence
<220> FEATURE:
<223> OTHER INFORMATION: Codon Optimized

<400> SEQUENCE: 69

| | |
|---|---|
| tacccatacg acgttcctga ttacgctgcc acttgcgcaa atggtaagac cgttggtgac | 60 |
| gcaagctgct gtgcctggtt tgatgtacta gacgatattc aggcaaacat gttccatgga | 120 |
| ggtcagtgcg gagcggaggc acacgagtca attcgccttg tatttcacga ctctatcgcg | 180 |
| atcagcccgg ctatggaggc gaaaggcaag ttcggtggcg gtggggccga tggttcaatt | 240 |
| atgattttcg acacaatcga gactgcattc caccccaaca tcggcctgga tgaagtcgtt | 300 |
| gctatgcaga aaccgttcgt tcaaaagcac ggagttacac ccggcgactt tattgccttc | 360 |
| gcgggagcgg tcgccctgag caattgtcca ggcgcgccgc agatgaactt cttcaccggg | 420 |
| cgcaaaccgg caacacaacc cgcccccgac ggcctggtgc cggagccatt ccacacggta | 480 |
| gaccagatca tcgcaagagt caacgatgcc ggggagttcg acgagctgga gctcgtatgg | 540 |
| atgctgtcag ctcattcggt cgcagcagtc aacgacgtgg atcccaccgt tcagggattg | 600 |
| ccattcgaca gcactccggg gattttcgac tctcaatttt tcgttgagac tcagttcagg | 660 |
| ggaacattgt tcccaggttc cggggcaac cagggtgaag tcgagtcagg tatggctggg | 720 |
| gaaatacgga tacagactga tcacacttta gcccgtgact cgcgcacggc ctgcgagtgg | 780 |
| cagtcttttg tcggtaacca atcgaagctc gtcgatgatt ttcagttcat ctttcttgca | 840 |
| ctgacccagc ttggccagga tcccaacgca atgactgatt gcagtgacgt tattccattg | 900 |
| tccaaaccaa ttccggggaa cgggcccttc tcattcttcc cacctgggaa aagccattct | 960 |
| gatatagaac aggcttgtgc cgagacaccg ttcccttctc ttgtcacact gccaggtccc | 1020 |
| gcaacttcag ttgctaggat tccaccacac aaagcagaac aaaagttgat ttctgaagag | 1080 |
| gatttgtgat aa | 1092 |

<210> SEQ ID NO 70
<211> LENGTH: 1077
<212> TYPE: DNA
<213> ORGANISM: Artificial Sequence
<220> FEATURE:
<223> OTHER INFORMATION: Codon Optimized

<400> SEQUENCE: 70

```
tacccatacg acgttcctga ttacgctgcg acatgcccag acggtaacac cgtcacgaat      60
gaagcttgct gctttctctt tcccattctt gaagatattc aggccaacct ctttaatggc     120
ggggagtgcg gctcggaggc tcatgagtcc ctgcggctca cgttccatga cgcaatcggc     180
ttctctccag ccctgacagc tcagggtcaa ttcggcggtg gtggcgccga tggttcggta     240
attacctttg cttctattga gactgcttac gctgcgaatg caggcatcga agatatagtc     300
gccgaacaag cgcagtttgt cgcgaagtat aacgtgtcag ccggggactt tgtacagttc     360
gctggggccg tgggcttgtc gaactgccct ggagccccac agctcgattt tgttatcggt     420
cgtccggcgg ccacggctgc atcaccggac ggtttagtcc ctgagccttt cgataacgtt     480
acttcgatct tggcccgttt caacgatgct ggcgggttcg acccacaaca tgtcgtctgg     540
ctcttaagta gtcattccgt tgcagctgct gagctggtcg accctagtat ccccggcgcc     600
ccgtttgata gtactcctgg cttgtttgac acacagttct ttattgagac acaactgacc     660
gggaccctct ggccaggtac ggcaaataac aaggggagg tcgagtcccc gctcctgggc     720
gaaattcggc ttcaatccga ttttctgctg ccagagata accgcaccgc atgcgagtgg     780
caatcgttcg ctaacgattt gtccaggcag cagacgcttt taaggcggc aatgtcaacg     840
ctggccacaa taggtcaaga tacgtccaca ctgactgact gttcggatgt gattcccgta     900
ccagctgctc cggttggcac cccacatttc cctgccggtt tgactaatgc tgacgtagac     960
caagcctgca cgaccgcagc ctttcccacg cttttccacgg atccaggccc cgctacatct    1020
gtggcacccg tccccacggc tgaacaaaag ttgatttctg aagaggattt gtgataa      1077
```

<210> SEQ ID NO 71
<211> LENGTH: 1101
<212> TYPE: DNA
<213> ORGANISM: Artificial Sequence
<220> FEATURE:
<223> OTHER INFORMATION: Codon Optimized

<400> SEQUENCE: 71

```
tacccatacg acgttcctga ttacgctgtc gcgtgccctg atggcgttaa caccgcaaca      60
aatgctgctt gttgccaact cttcgcggtc cgtgaggatc tccaacagaa tctgttccac     120
ggagggctct gtactgctga ggctcatgag agcctgcgac tcacattcca tgatgctatt     180
gcgatcagtc cggctttgga ggcgcaagga atcttcggcg gaggtggcgc tgatggttcg     240
attgctatat cccagagat cgagactaat ttccacccga atataggggct cgatgagata     300
attgaactcc aaaagccatt tatcgcacgc cataatatct ctgttgccga cttcattcaa     360
ttcgccggtg ccattggcgc cagtaactgt gccggagctc cccaactagc ggctttcgtg     420
gggcgtaagg atgcgaccca accccccccg gatggactag ttcctgagcc atttcacacg     480
cctgaccaaa tattcgaccg tcttgctgat gcatcgcagg gggagttcga tcctatactc     540
acagtttggc tcctcactgc gcatacagta gctgcagcca atgatgtgga ccccacgaag     600
tcgggcctcc ccttcgatag cacacccgag ctatgggata ctcaattctt cctcgagaca     660
cagctcaggg gaacctcttt tccaggttca ggcggaaatc aaggcgaggt tgagtcccct     720
```

| | |
|---|---|
| ctggccgggg aaatgagact ccagtcagac cacacaatcg ctcgcgacag tcgtactgct | 780 |
| tgcgagtggc agtccttcgt cgacaaccaa ccgaaggcgc agcaaatgtt ccaattcgta | 840 |
| ttccacgatc tcagcatctt cggccaggat atcaacactc tagttgactg taccgaagtc | 900 |
| gttcctatcc ccgcagatcc tcaaggacat acacattttc ctgcagggtt gtcaaacgca | 960 |
| gatatcgaac aggcgtgtgc tgagactccc ttcccgacct tccccacgga cccaggacct | 1020 |
| aaaactgcag tcgctccggt ccctaagcct cctgcggccc gtaaggaaca aaagttgatt | 1080 |
| tctgaagagg atttgtgata a | 1101 |

<210> SEQ ID NO 72
<211> LENGTH: 1056
<212> TYPE: DNA
<213> ORGANISM: Artificial Sequence
<220> FEATURE:
<223> OTHER INFORMATION: Codon Optimized

<400> SEQUENCE: 72

| | |
|---|---|
| tacccatacg acgttcctga ttacgctgct acctgtgacg atggtaggac aacggcaaac | 60 |
| gcagcctgct gcatcctttt ccccatcctc gatgacatac aagagaacct gttcgacggt | 120 |
| gcccagtgtg gcgaagaggt ccacgagagt ctgcgcctca cttttcatga tgcaattggg | 180 |
| ttcagcccca cactaggcgg cggcggagcc gacggctcta tcatcgcgtt cgatacgatc | 240 |
| gaaaccaatt tcccggccaa tgcgggcatt gacgagattg tgtcagcaca gaaacctttc | 300 |
| gttgcaaagc ataatatcag cgcgggagat tttattcagt tcgctggtgc agttggtgtg | 360 |
| tcaaattgcc ctggcggcgt ccgtatcccg ttttcctcg gcaggccaga cgcagtggca | 420 |
| gcgagccctg accaccttgt ccccgaaccc ttcgatagcg ttgattccat tcttgcgaga | 480 |
| atggggggacg ccggctttc cccggtggag gtggtctggc tgctcgcttc gcattccatc | 540 |
| gcggcagcgg ataaagttga tccgtccatt cctggtacgc cttttgattc aaccctggt | 600 |
| gttttcgaca gccaattctt catagaaacc caactgaaag gccgtctgtt cccgggcacg | 660 |
| gcagataaca agggtgaggc acagtcgcct ttgcaaggcg aaatccgttt gcagagcgat | 720 |
| catctgcttg caagggaccc acagacagcc tgtgaatggc aatcaatggt gaacaatcag | 780 |
| ccgaagattc agaaccgctt cgctgccacg atgtcgaaga tggctctgct tggtcaggat | 840 |
| aaaacgaaac tgatcgactg ctccgatgtt atcccaactc cgcccgcttt ggttggcgca | 900 |
| gcgcaccttc cagctgggtt ctccctcagc gatgttgagc aggcgtgcgc agctacccct | 960 |
| ttccggctc tgaccgcaga ccccggcct gtcacctcag ttccgcccgt tcctggatcc | 1020 |
| gaacaaaagt tgatttctga agaggatttg tgataa | 1056 |

<210> SEQ ID NO 73
<211> LENGTH: 1134
<212> TYPE: DNA
<213> ORGANISM: Artificial Sequence
<220> FEATURE:
<223> OTHER INFORMATION: Codon Optimized

<400> SEQUENCE: 73

| | |
|---|---|
| tacccatacg acgttcctga ttacgctgcc gtctgcccgg atggaacaag ggtgtcgcac | 60 |
| gccgcttgtt gcgcgttcat tcctttagcc caggacctcc aagagactat attccagaac | 120 |
| gaatgcggtg aggacgcaca cgaggttatc cgtttgacct tccatgatgc catcgcgatt | 180 |
| tcccgctctc aaggtccaaa ggccggcggc ggtgcggacg gatccatgct actattcccc | 240 |
| acagttgaac cgaacttttc cgccaataat ggcatagacg atagtgtcaa caatctgatt | 300 |

```
cctttcatgc aaaagcacaa cacgatatcc gctgctgacc tcgttcagtt tgcaggcgct    360
gtcgccctga gcaactgccc cggtgcccct cgacttgaat ttctcgccgg ccgtccaaac    420
aagactatcg ctgcagttga cggcctcatc cccgagcccc aggacagtgt cacgaagatc    480
ctacagcgct tcgaggatgc cggggggtttt actcccttg aagtagtctc gctgctcgca    540
tctcactctg tcgctagggc cgacaaagtt gatcaaacca tcgatgcagc ccctttgac    600 tccacaccct tcacttttga tacgcaagtg ttcttggagg tcctgctcaa gggcgtgggt    660
ttcccgggat cagctaataa cacaggtgaa gttgccagcc ccttccgct tggctctggt    720 agcgatactg gtgaaatgag gctgcaaagc gactttgccc tcgcgcatga ccctcgaacc    780
gcctgtattt ggcagggatt cgtcaatgag caggcattta tggctgcctc gttccgcgca    840
gctatgagca agcttgcggt cctcggccat aatcgaaact ctttaatcga ttgttccgac    900
gtagtacccg tcccgaaacc tgctaccggt cagccagcaa tgttccctgc ctcgacgggt    960
cctcaagacc tggagttatc gtgcccatcc gagcgatttc ctaccctgac aactcagcct   1020
ggtgctagcc aatcgctcat tgcccattgc cctgacggct caatgtcctg cccaggagtc   1080
cagttcaatg gtccggcgga acaaaagttg atttctgaag aggatttgtg ataa         1134
```

<210> SEQ ID NO 74
<211> LENGTH: 1059
<212> TYPE: DNA
<213> ORGANISM: Artificial Sequence
<220> FEATURE:
<223> OTHER INFORMATION: Codon Optimized

<400> SEQUENCE: 74

```
tacccatacg acgttcctga ttacgctgcc acttgcgcgg gtggccaggt tacggcgaac     60
gcggcttgtt gcgtgctttt ccccctcatg gaagatctgc agaagaatct tttcgatgac    120
ggggcatgcg gagaggatgc gcatgaagcc ctgcgtctta catttcatga cgcaattggc    180
ttcagtccta gccgaggagt catgggtggc gctgatggaa gcgttatcac gttttccgat    240
acagaagtta atttttccagc aaacctaggc attgacgaga ttgttgaagc ggagaaacct    300
tttcttgcaa ggcacaacat tcggcgggg gatctcgtcc atttcgcagg aacgctcgct    360
gtaaccaact gccccggagc gccacgaatt cctttttttc tcggccggcc gcccgctaag    420
gcagccagcc caatcgggct ggtgccgag cctttcgaca ccatcactga cattctcgca    480
agaatggatg atgcgggatt tgtgtccgtg gaggttgtgt ggctgctctc agcccatagt    540
gtcgcagcag ctgaccatgt cgatgagaca atccccggca ccccttttga ctctacgcca    600
aacctgtttg actcccaaat ctttatcgag actcaattgc gaggaattag ctttcctggc    660 acggaggaa accacggaga agttcagagc ccctcaaag gagaaatgcg actccaatcc    720
gatcacctct tcgcccgcga cgaccgtaca agttgtgagt ggcaaagcat gacaaatgac    780
caacagaaaa tccaggatcg cttagcgat acgctgttca agatgtcgat gctcggtcaa    840
aatcaggacg ccatgatcga ttgctcagac gtaattcctg tcccggcagc gctcgtcaca    900
aaacctcatc ttcccgcggg caagtctaaa accgacgttg agcaggcatg tgcgacggga    960
gcttttccgg ctttaggagc ggatccaggt cctgtgacct ccgttccgcg cgtgcccccc   1020
gccgaacaaa agttgatttc tgaagaggat ttgtgataa                          1059
```

<210> SEQ ID NO 75
<211> LENGTH: 2328
<212> TYPE: DNA

<213> ORGANISM: Artificial Sequence
<220> FEATURE:
<223> OTHER INFORMATION: Codon Optimized

<400> SEQUENCE: 75

```
tacccatacg acgttcctga ttacgctcag tccgcatcgc aatttacgga tccgaccacg    60
ggtttccagt ttactggaat caccgatccc gtgcatgatg tcacgtacgg tttcgtgttt   120
ccaccgctcg ccactagtgg ggctcaaagc accgaattca tcggcgaggt tgtcgcaccc   180
atcgcgtcta aatggatcgg aatcgcccta ggtggtgcga tgaacaacga cttactcctg   240
gtcgcctggg caaatggcaa ccagatcgtc agcagcacgc gctgggctac cggttacgtc   300
cagcccacgg cctatactgg tactgctacg ctgaccactc ttccagaaac gacgatcaat   360
agtacacact ggaagtgggt ctttcgttgc caaggatgta ctgaatggaa caatggcggt   420
ggcattgacg tgacaagcca gggtgttcta gcctgggcat ttagcaatgt cgctgttgat   480
gacccgtcgg atccacagtc aacttttcca gagcacacgg atttcgggtt ctttggcatc   540
gactacagca ccgcccacag cgccaactat cagaattacc tgaatgggga ttctggcaat   600
cctacgacaa cgtccacaaa accgacatct acgagctcca gcgtcactac ggggcccacc   660
gtttctgcca ccccatacga ttatattatt gtcggggcag gccaggtgg aatcatcgcc   720
gccgatcgac tgagcgaggc cggcaagaag gtccttctgc tcgaaagagg tggtccaagc   780
acgaaacaaa ccggcggtac ttatgtggcg ccatggctac cttcctcagg gctgacgaaa   840
tttgacatcc cgggcttgtt cgagtccctc ttcacagata gcaatccatt ctggtggtgc   900
aaggatatta ccgtctttgc cggttgtctg gttggagggg gtactagcgt caacggcgca   960
ctatactggt atcctaacga cggagatttc agcagcagtg tcgggtggcc gtcctcatgg  1020
actaatcatg ccccttacac cagtaaactg agcagcagac taccatccac cgaccatcct  1080
tctacggatg gtcaacgcta tctggaacaa gcttcaacg ttgtcagtca acttctcaag  1140
ggccagggtt acaatcaggc tacgatcaac gacaatccga attataagga tcatgtcttt  1200
ggatacagcg ccttcgactt tctgaacggc aagcgtgctg gtccagtcgc cacgtacctt  1260
caaactgctt tggcgcgtcc taatttcact ttcaagacga acgtcatggt ttctaatgtc  1320
gtccgcaacg gctcccagat tctcggagtc caaaccaatg atccaaccct aggcccgaac  1380
ggattcattc cagtaacgcc aaagggtaga gtaatcctct cggctggcgc tttcggtaca  1440
tcccgcatac tattccaaag tggcatagga ccgactgata tgatccagac cgtccagtcc  1500
aatcctacgg ctgcggccgc gctgcccccg caaaatcagt ggattaatct tccagtgggt  1560
atgaatgccc aagacaatcc ttccataaat ttagtattta cccatccgag tatcgacgcc  1620
tatgagaact gggcggatgt ctggtcaaac cccaggccag ccgatgctgc acaatacttg  1680
gcaaatcaga gcggcgtttt cgcgggcgct tcccctaagc ttaatttctg gagagcttat  1740
agtggctccg acggatttac acgatacgcc caaggcactg taaggccagg agctgcgtcc  1800
gtcaactctt cccttccgta taacgccagt caaatcttca ccataacggt ttatctgtct  1860
acaggcattc aatcacgtgg tcgaataggc atcgatgcgg ccctgagagg caccgtactc  1920
acgccccctt ggctgcttaa tccagttgat aaaacagtat tgcttcaggc gctccacgac  1980
gtcgtcagca acataggttc cattccaggc ctaactatga ttacgccaga tgtcactcaa  2040
acccttgaag agtacgtaga tgcatatgac cctgctacta tgaactcaaa ccattgggtt  2100
tcctcgacca ctatcggatc ctcaccccag tctgcgcgtgg tcgattccaa cgtgaaggtt  2160
tttggcacta ataacctctt catcgtggat gcgggtataa tcccacatct tcctacaggt  2220
``` aaccccccaag gtacgctcat gtcggccgct gagcaagctg ccgcaaagat actcgcgctg    2280 gccggggggac cagaacaaaa gttgatttct gaagaggatt tgtgataa                 2328

<210> SEQ ID NO 76
<211> LENGTH: 1602
<212> TYPE: DNA
<213> ORGANISM: Artificial Sequence
<220> FEATURE:
<223> OTHER INFORMATION: Codon Optimized

<400> SEQUENCE: 76
tacccatacg acgttcctga ttacgctagc atcggccctc gtggtacgct gaacatcgca      60
aacgaagtga ttaagccaga cggcttcagt cgttcggcgg tactagccgg tggctcatac     120
ccggggcctc ttatcaaagg cgaaaccggt gaccgctttc agatcaatgt cgtaaacaag     180
ctcgcggaca cttccatgcc ggtagatacg tccatccatt ggcatgggat ctttgtaagg     240
gggcacaact gggccgacgg acctgcgatg gtgactcagt gtccgattgt tccaggtcac     300
agcttccttt acgatttcga atccccgac caggccggca cattctggta ccattcccac      360
cttggtaccc aatactgcga tggattgcgc ggtccgttcg tggtttattc taaaaatgac     420
cctcataagc gactctacga cgtggatgac gagtcaacgg tactgacggt cggcgactgg     480
tatcacgcac cttcgttgtc gttatccgga gttccgcacc cggacagcac tttatttaac     540
ggtttgggca gatcgctaaa tggtcccgct tctccattat acgtcatgaa cgtcgttaag     600
ggcaagcgtt ataggattcg cctgatcaac acgagctgtg attcaaacta ccaattcagc     660
atcgacggtc acgcattcac tgtgatcgag gcggacggag aaaatacaca acctcttcaa     720
gtcgatcaag tccagatttt cgctggccag aggtacagct tggtacttaa tgccaaccaa     780
gcggtcggca attactggat ccgggctaac cctaactccg ggaccctgg ctttgcaaac      840 caaatgaact cagccattct ccgatataaa ggtgccagga acgttgatcc gactacacca     900
gaacgtaacg cgacaaaccc gttgcgggaa tacaacttgc gcccgctaat aaaggaaccg     960
gctcccggaa agccttttcc tggcggcgcg gaccacaaca ttaatcttaa cttcgccttc    1020
gatccagcga ctgtgctttt tacggccaac aattatacct tcgtgccgcc aacggtgccc    1080
gtccttctcc agatcctatc gggcacccgc gacgctcatg atttggcacc cgctgggagt    1140
atctacgaca ttaagttggg cgacgtggtc gaggtgacaa tgcctgcact tgttttttgcg   1200 ggaccgcacc ccatgcactt gcacggtcat tcatttgccg ttgtcaggag cgcaggatcc    1260
tctacataca actatgaaaa cccggtgcgg cgggatgtag tgagcatcgg cgacgatcca    1320
actgacaacg ttacaattcg cttcgtggcg gataacgcgg ggccttggtt tttacactgc    1380
catattgatt ggcaccctcga cctgggattc gcggtggttt ttgcagaagg cgtgaaccaa    1440
acagcagtgg cgaacccggt gccggaagca tggaacgacc tctgccccat ttacaactcg    1500
tcgaacccga gtaaacttct gatgggtacg aatgcaattg gccgcctcca cgcccctttg    1560
aaggcggaac aaaagttgat ttctgaagag gatttgtgat aa                       1602

<210> SEQ ID NO 77
<211> LENGTH: 1761
<212> TYPE: DNA
<213> ORGANISM: Artificial Sequence
<220> FEATURE:
<223> OTHER INFORMATION: Codon Optimized

<400> SEQUENCE: 77

```
tacccatacg acgttcctga ttacgctgcg gattttgatt atgtggttgt cggtgctggg    60
aatgctggca acgtggttgc agcgcggttg acagaggacc ctgatgtgtc ggtcttggtt   120
ctggaagcgg gagtctcgga cgagaatgtg ctcggtgcag aggccccct ccttgccccg    180 ggcctggtcc cgaactcaat cttcgattgg aattacacga cgactgctca agcgggatat   240
aatgggagat cgatcgctta cccgagggga cgcatgctcg gcggttcctc aagcgtccac   300
tatatggtta tgatgcgtgg ttcgaccgag gattttgaca ggtatgctgc ggtgacaggg   360
gatgaaggtt ggaattggga caacattcag caattcgtcc gaaaaaatga gatggttgtc   420
cctcctgctg ataaccacaa cacgtctggc gaatttatcc cggcggtaca tggaactaat   480
ggctccgtca gcatatcact tcccggtttc ccgacaccgt tggatgaccg cgtcctcgct   540
actacccaag agcagagcga ggaattcttc tttaacccgg acatgggaac gggccatcca   600
ctgggtataa gctggtcgat tgcctcggtg ggaaacggcc agcggtctag ctcgtcgacg   660
gcgtatctcc gccctgcaca gagccgtccg aacctgtcgg tcctcataaa tgcccaggtg   720
accaagttag taaacagcgg tacaaccaat ggactgccgg catttcgatg tgtcgagtac   780
gctgagcagg agggggcccc aactactacg gtatgcgcaa agaaggaggt tgtcctttcc   840
gctggatccg tcggaactcc aatcctactt caacttagcg gcatcgggga tgaaaacgac   900
ctgtcctcag ttgggattga tacgatagtc aataacccctt ccgttgggcg caatctctct   960
gaccatcttc tcctccccgc agcttttctt gtcaattcca accagacgtt cgataacatc  1020
ttccgcgact cttctgagtt caatgtggac cttgaccaat ggaccaacac gcgcactggt  1080
ccattgactg ccctgattgc taaccacctc gcatggttgc gcctgccgtc gaattccagc  1140
atcttccaga cattccccga tccggccgcc gggccaaact ctgctcattg ggaaactata  1200
ttctcaaatc agtggttcca ccctgcaatt ccgcggcccg acacgggctc atttatgtcg  1260
gttacgaatg ccctgatcag ccctgttgcc cgtggagata taaagctcgc cactagcaat  1320
ccgttcgaca agcctctcat caatccccaa tatctctcta ctgaattcga cattttcact  1380
atgattcagg ccgtgaagtc aaacttgaga tttctctcag gtcaagcttg ggctgacttc  1440
gtcatacgtc cgttcgaccc ccggctccgc gacccaactg atgacgcggc tatcgagagc  1500
tacattcgtg ataatgcgaa cacgatcttc catccagtcg ggactgcttc aatgtccccg  1560
agaggcgctt cgtgggggtgt cgttgaccca gatcttaagg tcaaaggagt tgatgggtta  1620
cggatcgtcg acggctcaat cctgccattc gcccctaatg cacataccca agggccgatc  1680
tatttggtcg gcaaacaggg agccgatcta ataaaggccg atcaggaaca aaagttgatt  1740
tctgaagagg atttgtgata a                                            1761
```

<210> SEQ ID NO 78
<211> LENGTH: 81
<212> TYPE: DNA
<213> ORGANISM: Sinopodophyllum hexandrum

<400> SEQUENCE: 78

```
atgggaggag aaaaagcttt cagtttcatt ttcctcctct tcgtgtgctt cttcctagcc    60
aacctctctg ggtcttcagc t                                              81
```

<210> SEQ ID NO 79
<211> LENGTH: 75
<212> TYPE: DNA
<213> ORGANISM: Nicotiana benthamiana

<400> SEQUENCE: 79

```
atggaaaagc taaacctaat tctattgctt tcctccattg ctattaccat atcatcaatt    60
ccgtttgctc atgcc                                                     75

<210> SEQ ID NO 80
<211> LENGTH: 57
<212> TYPE: DNA
<213> ORGANISM: Nicotiana benthamiana

<400> SEQUENCE: 80
atgtcttgta aattagtact agctcttatg gttagtgctt ttgctattgc aactgcg       57

<210> SEQ ID NO 81
<211> LENGTH: 27
<212> TYPE: DNA
<213> ORGANISM: Artificial Sequence
<220> FEATURE:
<223> OTHER INFORMATION: N-terminal HA antibody staining tag

<400> SEQUENCE: 81
tacccatacg acgttcctga ttacgct                                        27

<210> SEQ ID NO 82
<211> LENGTH: 36
<212> TYPE: DNA
<213> ORGANISM: Artificial Sequence
<220> FEATURE:
<223> OTHER INFORMATION: C-terminal Myc antibody staining tag

<400> SEQUENCE: 82
gaacaaaagt tgatttctga agaggatttg tgataa                              36

<210> SEQ ID NO 83
<211> LENGTH: 75
<212> TYPE: DNA
<213> ORGANISM: Artificial Sequence
<220> FEATURE:
<223> OTHER INFORMATION: Myc tag with hexahistidine

<400> SEQUENCE: 83
gctagcgaac aaaaactcat ctcagaagag gatctgaata gcgccgtcga ccatcatcat    60
catcatcatt gataa                                                     75
```

METHODS AND SYSTEMS TO PRODUCE LIGNIN-MODIFYING ENZYMES AND USES THEREOF

CROSS REFERENCE TO RELATED APPLICATIONS

This application claims priority to U.S. Provisional Application Ser. No. 62/736,191, entitled "Heterologous Production of Fungal Lignin-Modifying Enzymes in *Nicotiana Benthamiana*" to Khlystov et al., filed Sep. 25, 2018, which is incorporated herein by reference in its entirety.

STATEMENT REGARDING FEDERALLY SPONSORED RESEARCH OR DEVELOPMENT

This invention was made with Governmental support under Grant No. DE-SC0014112 awarded by the U.S. Department of Energy. The government has certain rights in the invention.

SEQUENCE LISTING

This application hereby incorporates by reference the material of the electronic Sequence Listing filed concurrently herewith. The material in the electronic Sequence Listing is submitted as a text (.txt) file entitled "05832_SeqList_ST25.txt" created on Sep. 25, 2019, which has a file size of 140 KB, and is herein incorporated by reference in its entirety.

FIELD OF THE INVENTION

The present invention is directed to lignin-modifying enzymes, including methods of synthesis and applications thereof, more particularly, lignin-modifying enzymes generated in living tissue, which are created at a high rate and possess a high level of activity.

BACKGROUND OF THE INVENTION

Lignocellulose is the most abundant biopolymer on Earth, consisting of primarily two components: carbohydrate polymers collectively termed as cellulose and hemicellulose; and the random heterogeneous polymer that encapsulates them from pathogenic attack, lignin. Together, lignin and cellulose represent an attractive renewable source for commodity chemicals and fuels. Extensive efforts are underway to achieve lignin deconstruction through inorganic catalytic means; these processes however rely on aggressive chemical treatment and remain difficult to tune and engineer for the capture of valuable intermediate breakdown products. While the conversion of cellulosic biomass has been readily achieved in the industry, scalable and tunable valorization of lignin remains elusive.

SUMMARY OF THE INVENTION

Systems and methods to produce lignin-modifying enzymes in accordance with embodiments of the invention are disclosed. In one embodiment, a vehicle for gene expression includes an organism capable of expressing a gene transformed with an expression vector containing a lignin-modifying enzyme.

In a further embodiment, the lignin-modifying enzyme is isolated from a fungus.

In another embodiment, the lignin-modifying enzyme is isolated from a basidiomycete fungus.

In a still further embodiment, the lignin-modifying enzyme is isolated from a species selected from the group consisting of *Bjerkandera adusta, Ceriporiopsis subvermispora, Dichomitus squalens, Phanerochaete chrysosporium, Pleurotus eryngii, Pleurotus ostreatus, Phlebia radiata, Trametes cinnabarina, Trametes hirsuta,* and *Trametes versicolor.*

In still another embodiment, the lignin-modifying enzyme is selected from the group consisting of lignin peroxidases, versatile peroxidases, manganese peroxidases, laccases, aryl alcohol oxidases, sugar oxidases, and cellobiose dehydrogenases.

In a yet further embodiment, the expression vector further contains a signal peptide.

In yet another embodiment, the signal peptide guides the cell to export the lignin-modifying enzyme from a cell of the organism.

In a further embodiment again, the signal peptide is selected from the group consisting of SEQ ID NOs: 78-80.

In another embodiment again, the expression vector further contains a tag.

In a further additional embodiment, the tag is one or more of the group consisting of an HA tag, Myc tag, and hexahistidine tag.

In another additional embodiment, the tag is selected from the group consisting of SEQ ID NOs: 81-83.

In a still yet further embodiment, the organism is a yeast.

In still yet another embodiment, the organism is a plant.

In a still further embodiment again, the organism is *N. benthamiana.*

In still another embodiment again, the lignin-modifying enzyme is selected from the group consisting of SEQ ID NOs: 1-77, the expression vector further contains a signal peptide selected from the group consisting of SEQ ID NOs: 78-80, the expression vector further contains a tag selected from the group consisting of SEQ ID NOs: 81-83, and the organism is *N. benthamiana.*

In a still further additional embodiment, a method to produce lignin-modifying enzymes includes obtaining an expression vector containing a lignin-modifying enzyme, transforming an organism with the expression vector, allowing the organism to express the lignin-modifying enzyme contained within the expression vector, and extracting the lignin-modifying enzyme.

In still another additional embodiment, the extracting step utilizes vacuum infiltration and centrifugation to extract the lignin-modifying enzyme.

In a yet further embodiment again, the method further includes quantifying the lignin-modifying enzyme.

In yet another embodiment again, the lignin-modifying enzyme is selected from the group consisting of lignin peroxidases, versatile peroxidases, manganese peroxidases, laccases, aryl alcohol oxidases, sugar oxidases, and cellobiose dehydrogenases.

In a yet further additional embodiment, the organism is *N. benthamiana.*

Additional embodiments and features are set forth in part in the description that follows, and in part will become apparent to those skilled in the art upon examination of the specification or may be learned by the practice of the invention. A further understanding of the nature and advantages of the present invention may be realized by reference to the remaining portions of the specification and the drawings, which forms a part of this disclosure.

BRIEF DESCRIPTION OF THE DRAWINGS

These and other features and advantages of the present invention will be better understood by reference to the following detailed description when considered in conjunction with the accompanying drawings where:

FIG. 2 illustrates a chart of various classes of various lignin-modifying enzymes and origin species in accordance with various embodiments.

DETAILED DISCLOSURE OF THE INVENTION

Figure 1:
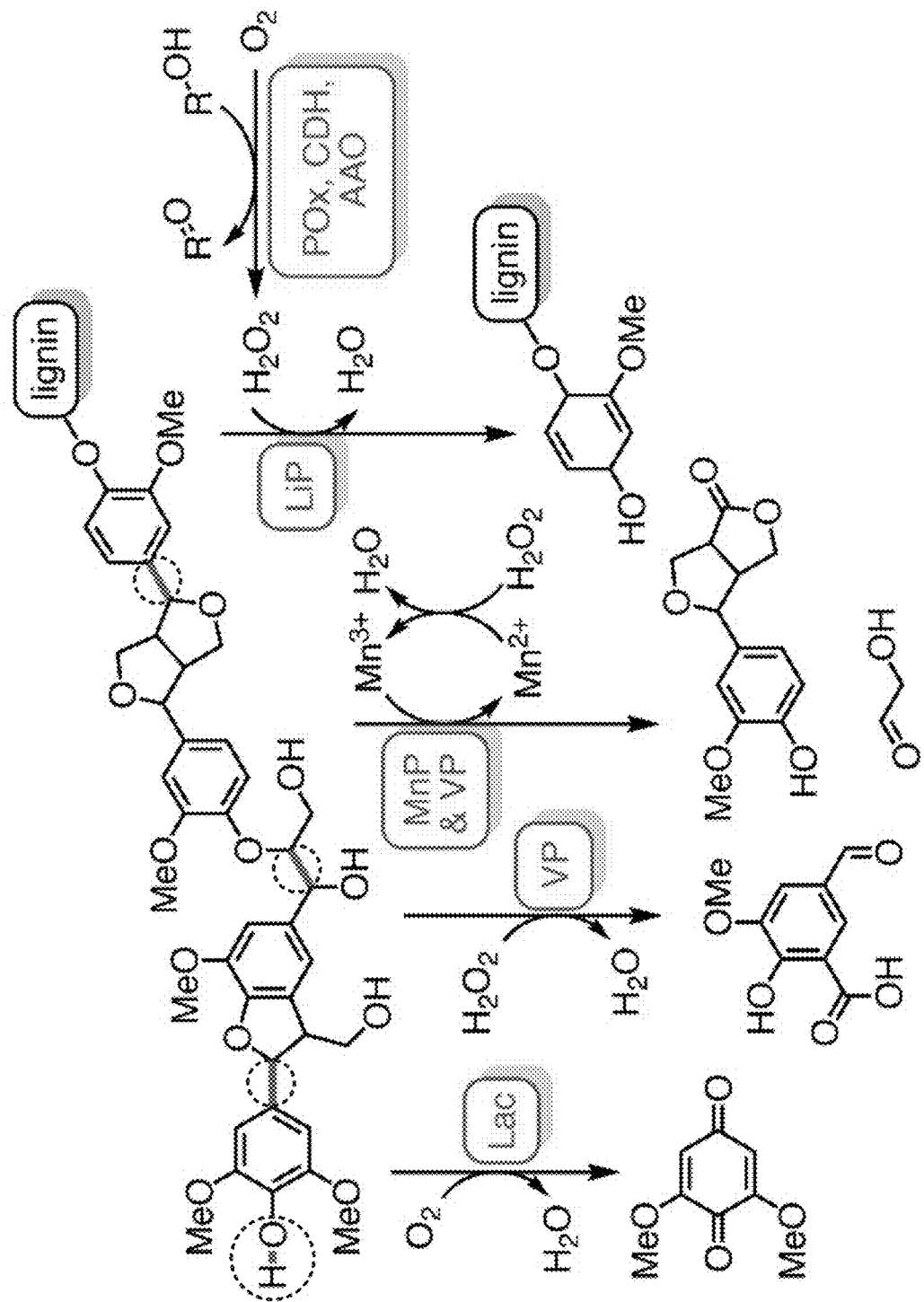
FIG. 1 illustrates lignin breakdown by various lignin-modifying enzymes in accordance with various embodiments.

Turning now to the diagrams and figures, embodiments of the invention are generally directed to lignin-modifying enzymes and systems and methods of their manufacture. In many embodiments, the lignin-modifying enzymes are lignin-degrading enzymes capable of breaking down lignin into component parts that are usable for other purposes. Several embodiments are directed to systems for producing lignin-modifying enzymes in vivo, including in yeast and/or plant species, and certain embodiments are directed to methods of creating these systems, including transfecting the species to produce lignin-modifying enzymes.

Fifty million tons of lignin are available each year through the paper pulping industry, but due to a lack of viable breakdown strategies, the vast majority is incinerated on-site to provide heat and electricity. Niche applications of whole lignin such as the production of phenolic resins and sustainable composites have been established, but the potential utility of lignin-derived components in the biofuels economy remains untapped. (See Li et al., A lignin-epoxy resin derived from biomass as an alternative to formaldehyde-based wood adhesives, Green Chem., 2018,20, 1459-1466; the disclosure of which is incorporated herein by reference in its entirety.)

Nature has evolved a biological path to lignin valorization through bacteria and especially basidiomycete fungi. Several bacterial species have been shown to be capable lignin metabolizers but are dwarfed by the lignin degradation rates of fungi. (See Ahmad et al., Development of novel assays for lignin degradation: comparative analysis of bacterial and fungal lignin degraders, Mol. BioSyst., 2010,6, 815-821; the disclosure of which is incorporated herein by reference in its entirety.) Thanks to recent major advances in genetics and bioinformatics, previous studies have elucidated the genomic origins of fungal lignin mineralization. (See Riley et al., Comparative genomics of biotechnologically important yeasts, Proc. Nat'l Acad. Sci. August 2016, 113 (35) 9882-9887; the disclosure of which is incorporated herein by reference in its entirety.) Several key enzyme families have been identified, and their lignin-degrading activity has been demonstrated through in vitro experiments. (See Hammel et al., Ligninolysis by a Purified Lignin Peroxidase, J. Biol. Chem., June 1993, 268 (17), 12274-81; and Warishii et al., In vitro depolymerization of lignin by manganese peroxidase of *Phanerochaete chrysosporium*, Biochem Biophys Rsch Comms, 1991 176(1) 269-75; the disclosures of which are incorporated herein by reference in their entireties.)

Many questions remain unanswered in regard to the specific mechanistic roles of the numerous individual lignin-modifying enzyme isoforms, and how these different enzymes concomitantly improve and/or alter the process of lignin metabolism in basidiomycetes., including why some ligninolytic fungi feature as many as 26 different peroxidase genes, including 13 MnP isoforms and how the activity is coordinated across the lignin polymer and during different stages in the deconstruction process. (See Fernandez-Fueyo, et al., Lignin-degrading Peroxidases from Genome of Selective Ligninolytic Fungus Ceriporiopsis subvermispora, J. Biol. Chem., 2012, 287, 16903-16916; the disclosure of which is incorporated herein by reference in its entirety.)

By far the greatest roadblock to accelerating the study of biological lignin degradation is the production of fungal lignin-modifying enzymes, particularly the important heme peroxidases. Previous research has relied primarily on enzymes purified from the native basidiomycete host or refolded from recombinant *E. coli*. Limited progress has been achieved in genetic engineering of basidiomycetes to homologously over-express lignin-degrading enzymes, but these hosts remain largely genetically intractable and more difficult to cultivate relative to microbial platforms. (See Lopez et al., Homologous and Heterologous Expression of Basidiomycete Genes Related to Plant Biomass Degradation, Homologous and Heterologous Expression of Basidiomycete Genes Related to Plant Biomass Degradation. In: Schmoll M., Dattenböck C. (eds) Gene Expression Systems in Fungi: Advancements and Applications. Fungal Biology. Springer, 2012; and Gelpke, et al., Homologous Expression of Recombinant Lignin Peroxidase in *Phanerochaete chrysosporium*, Applied and Enviro Microbio., 1999, 65(4), 1670-74; the disclosures of which are incorporated herein by reference in their entireties.) Moreover, any expression strategy in basidiomycete hosts suffers from the background of natively-produced lignin-degrading enzymes, requiring extensive purification to study individual members of the enzymatic milieu. (See Lambertz et al., Progress and obstacles in the production and application of recombinant lignin-degrading peroxidases, Bioengineered 2016 7(3); the disclosure of which is incorporated herein by reference in its entirety.) Their study by traditional methods such as reverse genetics also remains inaccessible due to the lack of genetic tools for basidiomycetes. Lignin-modifying enzymes produced from *E. coli* commonly suffer misfolding problems and must be refolded in vitro, an inherently lengthy and inefficient process with yields of at most 28%.

A major challenge in the production of these enzymes is their post-translational features, including four disulfide bonds, two calcium atoms, and a heme cofactor. Recombinant hosts such as *S. cerevisiae* are ill-equipped to handle this class of foreign enzymes; yeast do not natively secrete any peroxidases. Bacterial hosts likewise are poorly suited for post-translational modifications such as disulfide bonds and heme cofactor incorporation given their lack of specialized organelles; lignin-degrading enzymes produced in *E. coli* require in vitro refolding for these reasons. Without genetic tools for basidiomycete manipulation, the requirements of specialized cellular functions such as chaperones and transporters remain unknown, ruling out the possibility of importing these requirements into more amenable production hosts. The evolution or optimization of lignin-modifying enzymes for better production in model hosts is not a viable approach either. Oxidation of small molecule substrates commonly used to represent activity towards lignin involves different mechanisms and optimizing enzyme activity towards these substrates does not necessarily translate to improved lignin degradation. Screening for lignin degradation has not been yet achieved in a high-throughput manner.

In many embodiments, lignin-modifying enzymes are utilized as specialized catalysts for the oxidation of carbon-carbon bonds and phenolic functional groups that comprise lignin (FIG. 1). Of these, three classes of heme peroxidases, termed lignin peroxidase (LiP), manganese peroxidase (MnP), and versatile peroxidase (VP), undertake powerful oxidative roles in the initial stages of lignin metabolism. LiP catalyzes the single-electron oxidation of nonphenolic substrates such as lignin and related metabolites via long-range electron transfer (LRET) through a surface-exposed tryptophan. MnP lacks this tryptophan but instead features a manganese(II)-binding pocket, catalyzing lignin breakdown through oxidation of Mn(II) to Mn(III), which is readily chelated by organic acids and serves as a diffusible oxidative mediator. VP is an "evolutionary-hybrid" of MnP and LiP, having both the Mn-binding pocket and the surface tryptophan, allowing for multiple routes to lignin oxidation. Copper oxidases, termed laccases (lac), are also major contributors in lignin degradation in some fungi, particularly in the absence of LiP. Auxiliary enzymes such as flavin-dependent glucose and pyranose oxidases (GOx, POx) and cellobiose dehydrogenases (CDH) help facilitate the roles of the lignin-degrading enzymes through generation of peroxide and other, yet-undiscovered means. FIG. 1 illustrates a representative schematic of bond cleavage catalyzed by different families of lignin-modifying enzymes. In FIG. 1, the dashed circles indicate bonds cleaved by various enzymes of embodiments. Specifically, carbon-carbon bonds can be cleaved by heme peroxidases (e.g., MnP, VP, LiP), while phenolic bonds that can be cleaved by laccases (e.g., Lac). Additionally, pyranose oxidase (PDX) is an example of a peroxide-generating enzyme that can be coupled to peroxidase activity on lignin bonds.

Numerous embodiments are directed to heterologous expression platforms to produce fungal lignin-degrading heme peroxidases. In many these embodiments, the heterologous expression platform, or vehicle, is an organism capable of expressing a gene. Several embodiments will transform a vehicle with an expression vector containing a lignin-modifying enzyme, such as those described within this disclosure. Many embodiments will use yeast, such as *Saccharomyces cerevisiae* or other fungus, such as *Aspergillus nidulans*, as a vehicle, while certain embodiments will use a plant. Plants present an attractive candidate for the production of lignin-modifying enzymes given that they naturally produce numerous extracellular heme peroxidases for cell wall biosynthesis and morphogenesis. A number of embodiments are directed to tobacco plants (*N. benthamiana*). In many of these embodiments, the tobacco plants are capable of producing multiple isoforms of six major classes of lignin-degrading enzymes with high yields. Plant-based embodiments are capable of producing a number of these enzymes from numerous species including 58 lignin-degrading heme peroxidases, 10 fungal laccases, and representatives from other important classes of enzymes implicated in lignin degradation. Many embodiments produce heme peroxidases and a peroxide-generating oxidase, such as pyranose oxidase, glucose oxidase, and/or aryl alcohol oxidase, sourced from white-rot basidiomycetes and demonstrate cleavage of a model lignin dimer through their combination in vitro.

Lignin-Modifying Enzymes

Turning to FIG. 2, many embodiments are directed to lignin-modifying enzymes. The term lignin-modifying enzymes includes lignin-degrading enzymes and other enzymes that may aid in enzyme degradation or modification, including any fungal class II heme peroxidases. In number of embodiments, the class II heme peroxidase is selected from lignin peroxidases (LiP) (e.g., SEQ ID NOs: 1-17 and 69-71), versatile peroxidases (VP) (e.g., SEQ ID NOs: 18-24 and 72), manganese peroxidases (MnP) (e.g., SEQ ID NOs: 25-49 and 73-74). Additional embodiments will include a fungal cellobiose dehydrogenase (CDH) (e.g., SEQ ID NOs: 50-53 and 75), a fungal laccase (Lac) (e.g., SEQ ID NOs: 54-65 and 76), a fungal sugar oxidase (such as pyranose oxidase (Pox) (e.g., SEQ ID NO: 66), an aryl alcohol dehydrogenases (AAO) (e.g., SEQ ID NOs: 67-68 and 77), and/or any combination of peroxidases, dehydrogenases, laccases, or oxidases.

In a number of embodiments, the gene sequences for the various lignin-modifying enzymes are isolated from basidiomycete species. A number of embodiments will isolate the gene sequence from at least of species selected from the group consisting of *Bjerkandera adusta*, *Ceriporiopsis* (also known as *Gelatoporia*) *subvermispora*, *Dichomitus squalens*, *Phanerochaete chrysosporium*, *Pleurotus eryngii*, *Pleurotus ostreatus*, *Phlebia radiata*, *Trametes cinnabarina*, *Trametes hirsuta*, and *Trametes versicolor*.

FIG. 2 illustrates a chart of various classes of lignin-modifying enzymes (columns) along with a limited risk of fungal species from which each class arises (rows). The numbers in the chart indicates the number of isozymes transformed into plant embodiments and the total number of isozymes for that class in that species (i.e., isozymes transformed/total isozymes). The bolded and boxed number indicate successful heterologous expression of one or more isozyme from the category and species in an enzyme-expressing embodiment.

In further embodiments, an isolated gene will be codon optimized for a particular species. One of skill in the art is capable of optimizing sequences for preferred codons in a host organism or vehicle. Certain embodiments will codon optimize for *S. cerevisiae* (e.g., SEQ ID NOs: 1-68), while some embodiments will codon optimize for *Aspergillus nidulans* (e.g., SEQ ID NOs 69-77). Further embodiments will codon optimize for *N. benthamiana*, or any other species used as an expression vehicle (e.g., plant, fungus, etc.).

Lignin-Modifying Enzyme Constructs

In many embodiments, one or more lignin-modifying enzymes are placed in an expression vector to allow an expression vehicle to express the one or more lignin-modifying enzymes. In some of these embodiments, the expression construct is comprised of DNA, while other embodiments will utilize RNA (e.g., mRNA) for the construct. Using an RNA construct will allow for embodiments to bypass transcription and directly translate the gene into a peptide followed by protein folding. RNA-based constructs can further include modified or artificial bases to increase the half-life of the construct and/or increase translation of the gene to a peptide. Using DNA for the construct, the vehicle will transcribe the one or more lignin-modifying genes to an mRNA intermediate followed by translation into a peptide strand and protein folding.

Figure 3A:
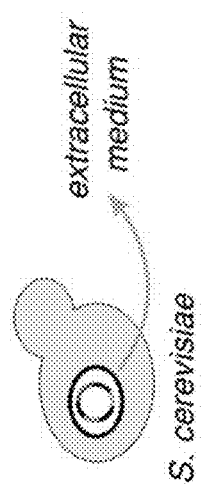
FIGS. 3A-3B illustrate schematics of expression vectors in accordance with various embodiments.
Figure 3A:
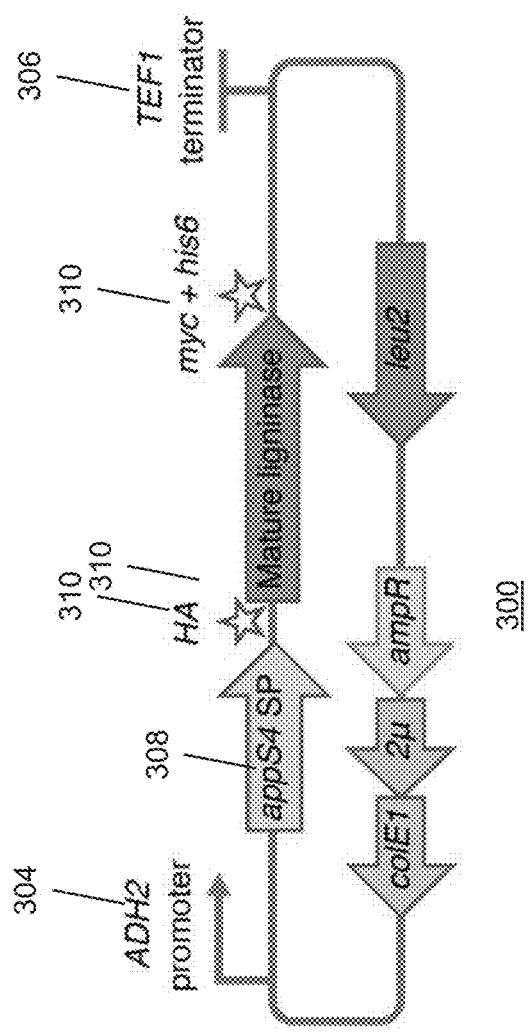
Figure 3B:
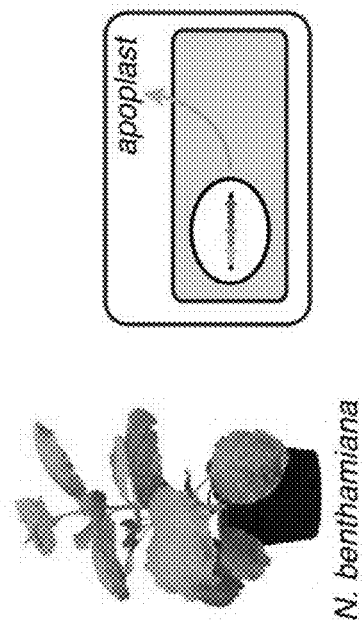
Figure 3B:
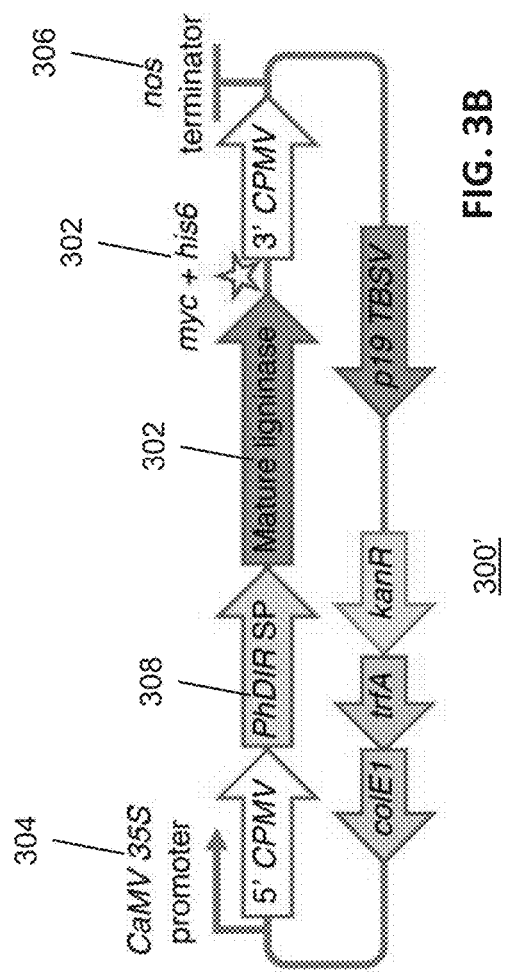

Turning to FIGS. 3A-3B, embodiments of expression vectors are illustrated. In particular, FIG. 3A illustrates a representative expression vector 300 for embodiments using yeast (e.g., *S. cerevisiae*) for expression, while FIG. 3B illustrates a representative expression vector 400' for embodiments using a plant (e.g., *N. benthamiana*) for expression. Embodiments of these vectors include a lignin-modifying enzyme 302 (e.g., SEQ ID NOs: 1-77) in addition to a number of other elements to assist in expression of the enzyme and/or replication of the vector. Many embodiments will include a promoter 304 and a terminator 306 to start and end (respectively) transcription of the enzyme 302. Promoters and terminators in accordance with many embodiments will be specific or optimal for the specific vehicle being used (e.g., yeast versus plants). Additional embodiments will utilize constitutive promoters (e.g., CAMV 35S promoter), while some embodiments will utilize inducible promoters, and further embodiments will use tissue specific promoters. Additionally, terminators can be selected based on efficacy or organismal specificity. As such, many embodiments will utilize TEF1 terminators, while certain embodiments will use a nos terminator.

Figure 4:
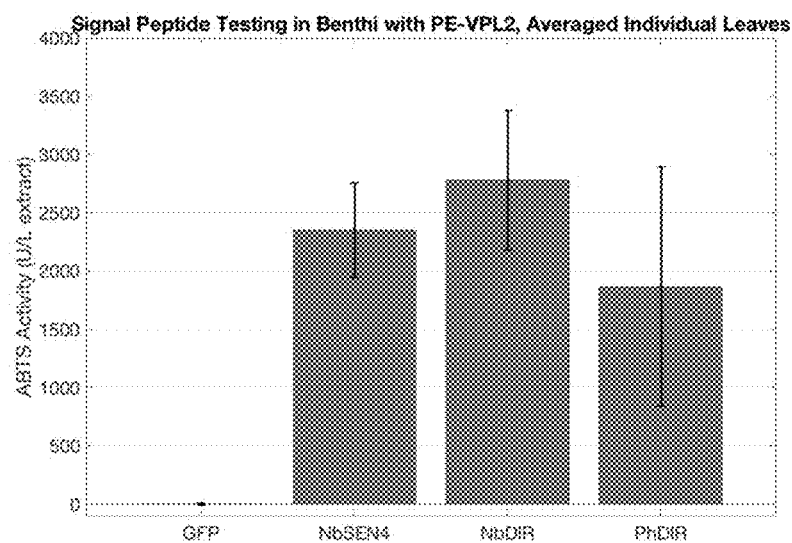
FIG. 4 illustrates a graph of enzyme activity of apoplast extracted lignin-modifying enzymes in accordance with various embodiments.

Further embodiments will include f peptide gene 308 to guide the final enzyme to transport a mature enzyme to a specific area of the cell (e.g., membrane and/or organelle) or to be exported from the cell (e.g., into media and/or apoplast). Many embodiments will use a PhDIR (SEQ ID NO: 78), NbDIR (SEQ ID NO: 79), and/or NbSEN4 (SEQ ID NO: 80) for the signal peptide. FIG. 4 illustrates the activity of various embodiments of a versatile peroxidase, PE-VPL2 (SEQ ID NO:22), attached to signal peptides NbSEN4 (SEQ ID NO: 80), NbDIR (SEQ ID NO: 79), and PhDIR (SEQ ID NO: 78), and GFP from apoplastic extraction. FIG. 4 illustrates that the inclusion of certain signal peptides allows exportation of mature enzymes of many embodiments to the apoplast of a cell.

Numerous embodiments will include tags 310 to assist for many purposes including to purify, identify, and/or localize the position of a mature enzyme. Many embodiments will utilize Myc tag (e.g., SEQ ID No: 82), hexahistidine tag (e.g., SEQ ID No: 83), HA tag (e.g., SEQ ID No: 81), and/or any other applicable tag.

Additional embodiments will include elements to assist in expression (e.g., transcription and/or translation), replication of the vector, and/or selection of specific vectors. Additional elements can include antibiotic resistance genes, gene enhancers, replication start sites, and/or any combination thereof. When using additional elements (such as promoters, terminators, etc.), one in the skill of the art will know where to position these elements in relation to the coding sequence of a lignin-modifying gene (e.g., whether the coding sequence for the signaling peptide and/or coding sequence for the tags is placed 5' or 3' in relation to the coding sequence of the lignin modifying gene).

Many embodiments will utilize a combination of a promoter, a signaling peptide, and a terminator; for example, some embodiments will possess a 35S promoter, and ER signaling peptide, a lignin-modifying enzyme gene, and a Nos terminator. Further embodiments will also include tags, including an HA tag (SEQ ID NO: 81), a hexahistidine tag (SEQ ID No: 83, a Myc tag (SEQ ID No: 82), and/or a GFP appended to the transcribed and/or translated sequence. Additional embodiments will include more than one enzyme-encoding gene within the construct, such that two enzymes will be expressed based from the construct.

Certain DNA-based constructs will be loaded into a replication and/or expression vector to allow for bacterial amplification or replication of the construct. Typically, these vectors are plasmids that are known in the art and can be purchased commercially. In many embodiments, the DNA construct will be integrated into a pEAQ vector to allow for replication and expression of the construct.

Producing Lignin-Modifying Enzymes in vivo

Figure 5:
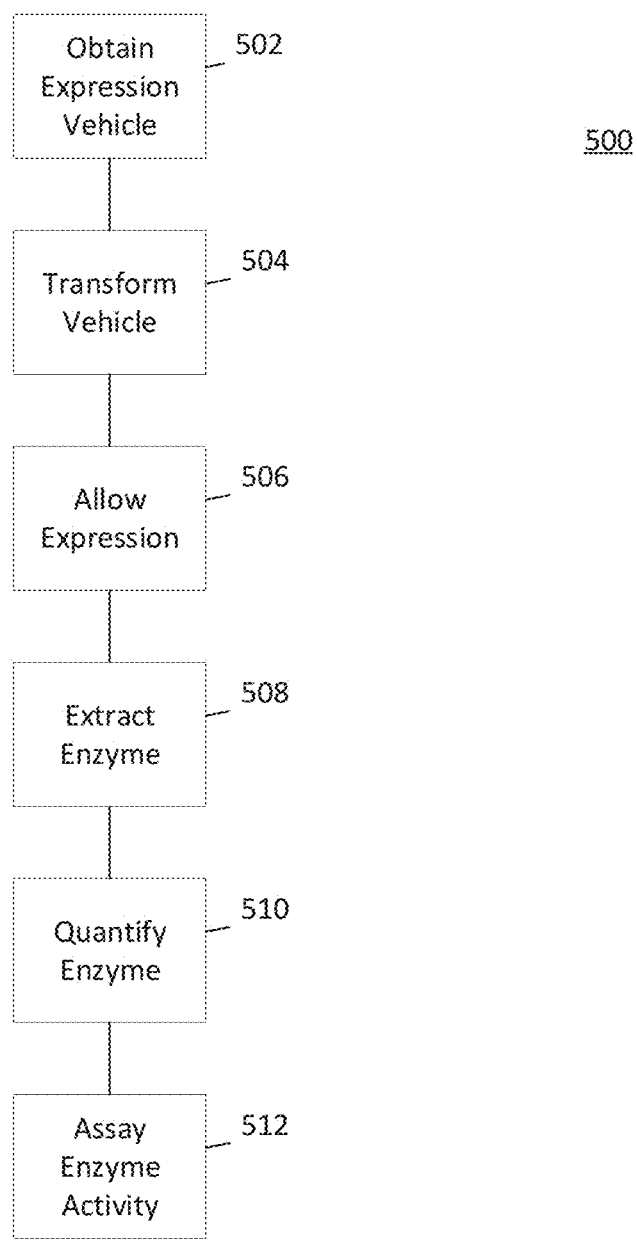
FIG. 5 illustrates a method for generating lignin-modifying enzymes in accordance with various embodiments.

Turning to FIG. 5, several embodiments are directed to methods of producing lignin-modifying enzymes in vivo. For example, method 500 illustrates a number of steps that many embodiments may utilize to produce lignin-modifying enzymes in vivo. At step 502 of many embodiments, an expression vehicle is obtained. In certain embodiments, the expression vehicle is a single- or multi-cell living organism capable of producing proteins. For example, the expression vehicle can be bacteria, archaea, yeast (e.g., *A. nidulans* and/or *S. cerevisiae*), animal, or plant (e.g., *N. benthamiana, Zea mays, Glycine max, Brassica* spp., etc.). In many of these embodiments, the obtained vehicle will be cultured or grown to a certain stage to allow for genetic transformation. For example, for cultured cells, the cells may be grown to a certain amount of growth on media and/or concentration of cells in liquid culture. For plants or larger organisms, the vehicle can be grown to a certain age or amount of growth, such as approximately 3 weeks, 4 weeks, 5 weeks, or 6 weeks. In some embodiments, the vehicle is *N. benthamiana* and is grown for approximately 5 weeks.

At step 504, the vehicle of many embodiments is transformed with a construct including a gene encoding a lignin-modifying enzyme (e.g., SEQ ID Nos: 1-77), such as described herein. Many methods of transforming are known in the art, which can be used in these embodiments. For example, embodiments will utilize transformation methods including *Agrobacterium tumefaciens*, particle bombardment, electroporation, any other method for introducing DNA into cells, or any combination thereof.

In some embodiments, two or more genes will be transformed into the vehicle. In such embodiments with multiple genes are transformed into the vehicle, some embodiments will perform a single transformation but include a mixture of the two constructs. In additional embodiments, two transformation steps will be performed, where each step only transforms a single gene into the vehicle.

At step 506, the vehicle is allowed to express the gene in a number of embodiments. In many embodiments, allowing expression involves growing the vehicle for a period of time. In cultured cells, such as yeast, bacteria, and/or cell lines, step 506 involves incubating the vehicle in culture for a period of time under optimal conditions for the culture. For full organisms, step 506 involves growing the vehicle in an environment for a period of time. For plants, the growth can occur in a controlled environment, such as a greenhouse or growth chamber, or plants can be grown outside, such as in a field or garden. The expression time can range in time from a number of hours to a number of days. For example, some embodiments will allow gene expression to last for 3 hours, 6 hours, 12 hours, 18 hours, 24 hours, 2 days, 3 days, 4 days, 5 days, 7 days, 10 days, or 15 days. Additionally, some embodiments will manipulate light cycles for optimal growth, if needed (e.g., plants), thus some embodiments will utilize a light cycle of approximately 9 hours, approximately 12 hours, approximately 13 hours, approximately 14 hours, approximately 15 hours, approximately 16 hours, approximately 17 hours, approximately 18 hours, approximately 20 hours, approximately 22 hours, or approximately 24 hours. In some embodiments using an *N. benthamiana* vehicle, the *N. benthamiana* plants are grown for 4 days with a 16-hour light cycle.

After the genes are allowed to express for a period of time, many embodiments will extract the lignin-modifying enzyme at step 508. The extraction process entails a number of methods as known in the art, including ion-exchange chromatography, size-exclusion chromatography, immuno-affinity chromatography (e.g., using a tag), vacuum infiltration, centrifugation, any other method of isolation, and any combination thereof. Certain embodiments will utilize vacuum infiltration and centrifugation to extract lignin-modifying enzymes.

Many embodiments will quantify the extracted enzymes at step 510. Many quantification methods are known in the art that are satisfactory for this purpose, including western blotting, ELISA, and/or spectroscopy methods, such as fluorescence or UV-Vis spectroscopy.

A number of embodiments will test the extracted lignin-modifying enzyme for activity at step 512. In some embodiments, the extracted enzymes will be tested against an applicable substrate, such as a colorimetric dye (e.g., ABTS), or a model lignin dimer (e.g., β-O-4). Further embodiments will also test activity against lignin-related substrates, such as veratryl alcohol (VA) and/or Manganese. Such testing can be performed a number of ways known in the art, which are satisfactory for measuring the activity, such as ELISA.

The above steps of the flow diagrams of FIG. 5 may be executed or performed in any order or sequence not limited to the order and sequence shown and described in FIG. 5. Some of the above steps of the flow diagrams of FIG. 5 may be executed or performed substantially simultaneously where appropriate—for example, some embodiments may quantify and assay activity simultaneously or as a single step. Some of the above steps of the flow diagrams of FIG. 5 may be omitted, such as omitting assaying the activity.

Lignin-Modifying Enzyme Activity

Figure 6A:
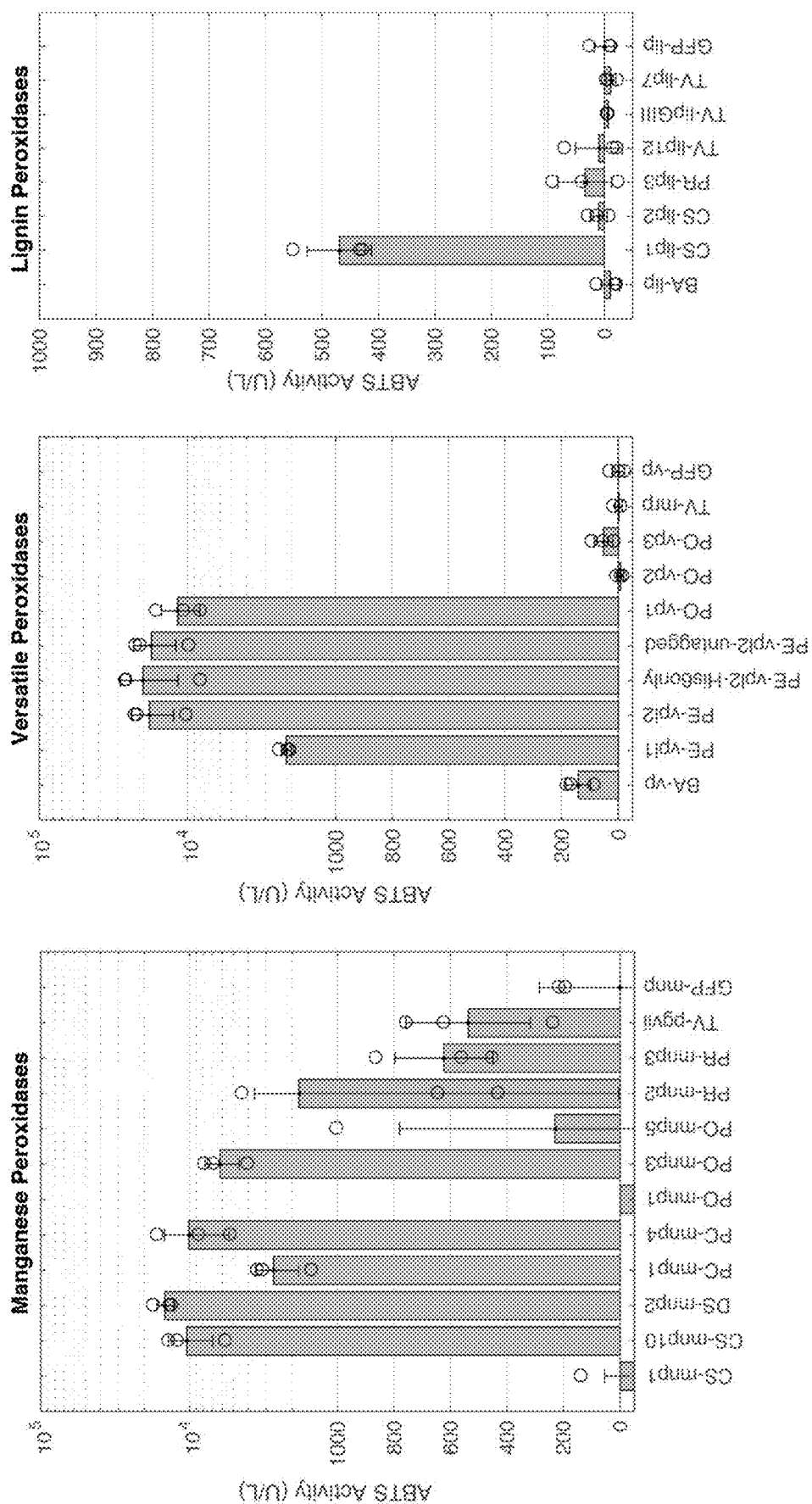
FIGS. 6A-6B illustrate charts of enzymatic activity against ABTS, manganese, and veratryl alcohol from lignin-modifying enzymes isolated from *N. benthamiana* in accordance with various embodiments.
Figure 6B:
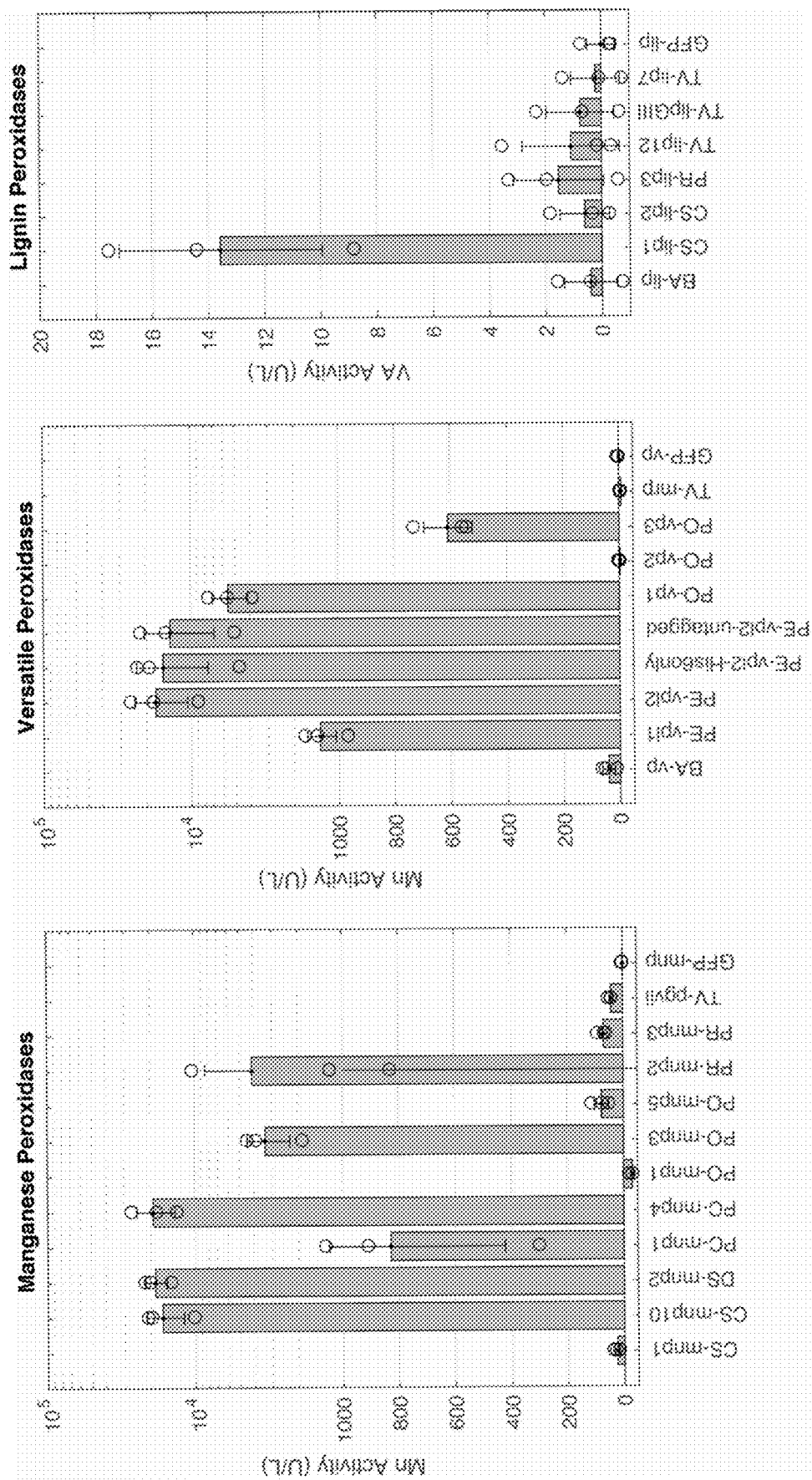

As described above in reference to FIG. 5, certain embodiments are directed to assaying the activity of lignin-modifying enzymes extracted from additional embodiments. Turning to FIGS. 6A-6B, the activities of certain embodiments are illustrated. For example, FIG. 6A illustrates the activity of various manganese peroxidases, versatile peroxidases, and lignin peroxidases against the colorimetric dye, ABTS, from embodiments using *N. benthamiana* for expression. Similarly, FIG. 6B illustrates the activity of various manganese peroxidases and versatile peroxidases against manganese (oxidation of Mn(II) to Mn(III)) and lignin peroxidases against veratryl alcohol (VA). The activities (U/L) in these figures represent 1 μM of oxidized product formed per minute per liter and show that certain embodiments are able to produce functional lignin-modify enzymes capable of oxidizing ABTS and Mn(II) of at least 200 U/L, 1000 U/L, and 10,000 U/L, as well as oxidizing VA at levels of at least 2 U/L, 5 U/L, 10 U/L, and 12 U/L.

Figure 7A:
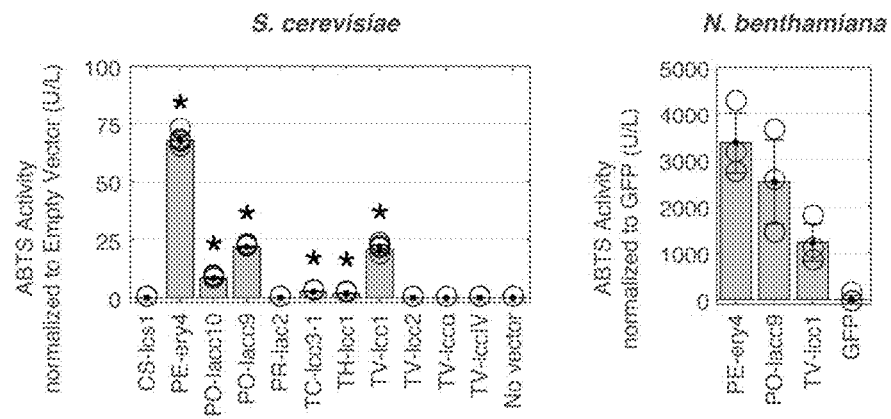
FIGS. 7A-7C illustrate charts of enzymatic activity against ABTS and DCIP from lignin-modifying enzymes isolated from *S. cerevisiae* and *N. benthamiana* in accordance with various embodiments.
Figure 7B:
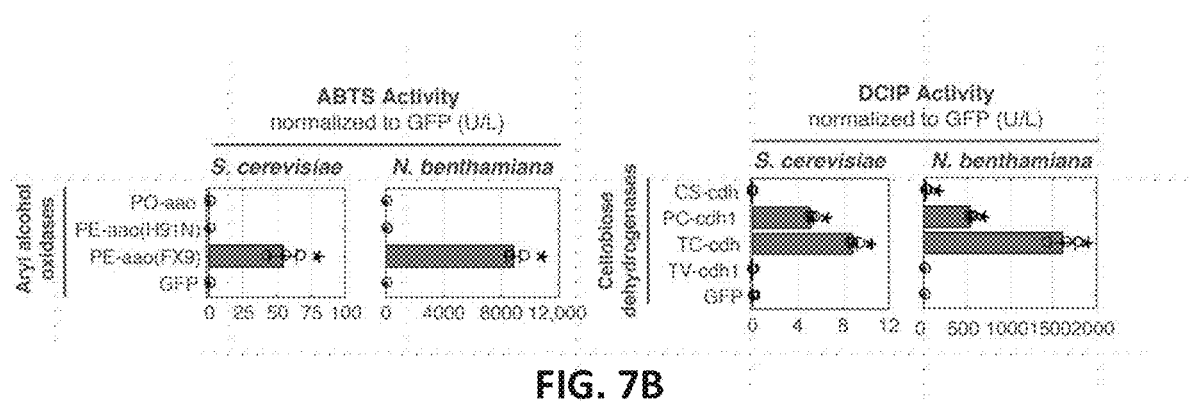
Figure 7C:
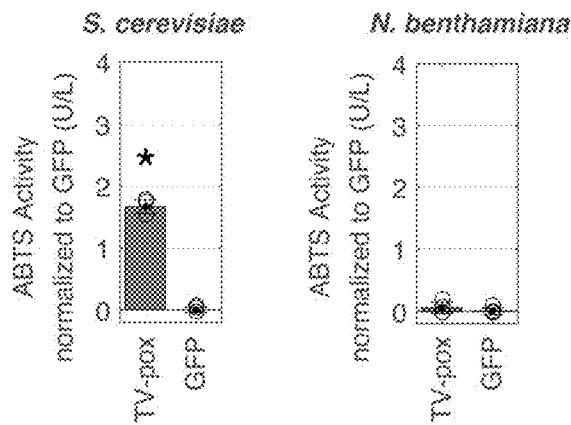

Turning to FIGS. 7A-7C, enzymatic activity of laccases, aryl alcohol oxidases, and pyranose oxidases are illustrated for many embodiments. In particular, FIG. 7A illustrates the ability of various laccases against ABTS from enzymes expressed in yeast *S. cerevisiae* and *N. benthamiana*. As illustrated, many embodiments are able to produce enzyme with activity of approximately 25 U/L or greater from expression in yeast (*S. cerevisiae*) and of approximately 1000 U/L or greater from expression in *N. benthamiana*. FIG. 7B shows the activity of aryl alcohol oxidases against ABTS and cellobiose dehydrogenases against DCIP (another colorimetric dye) expressed in yeast and *N. benthamiana*, which show that embodiments are capable of producing aryl alcohol oxidases with activity of at least about 50 U/L in yeast and of at least about 8000 U/L in *N. benthamiana*. Similarly, embodiments of yeast expression can produce cellobiose dehydrogenases with at least 4 U/L in yeast and at least 500 U/L in *N. benthamiana*. FIG. 7C illustrates the activity of embodiments of pyranose oxidases expressed in yeast and *N. benthamiana*, which show that embodiments are capable of producing pyranose oxidases with an activity of at least approximately 1.5 U/L in yeast.

Figure 8:
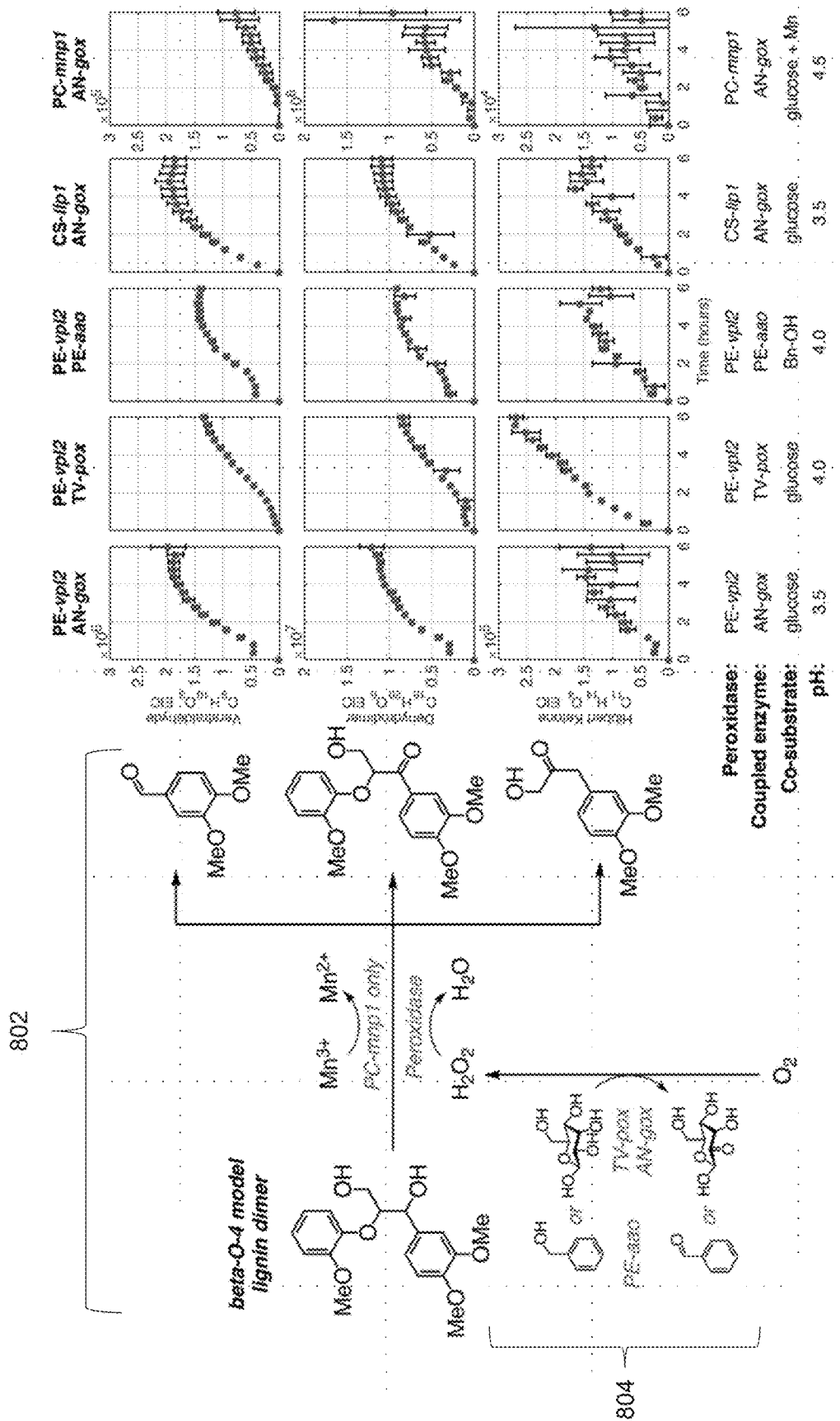
FIG. 8 illustrates enzymatic activity of coupled enzymes against a model lignin dimer, β-O-4, in accordance with various embodiments.

Turning to FIG. 8, enzyme kinetic activity of various embodiments as measured by LC-MS are illustrated. Specifically, FIG. 8 illustrates a lignin breakdown reaction 802 using peroxidases of various embodiments to break down β-O-4 and reduce hydrogen peroxide to water and/or Mn(III) to Mn(II). Specifically, β-O-4 is broken down into the products veratraldehyde, dehydrodimer, and Hibbert Ketone. As seen in FIG. 8, the production of each product increases over the time the reaction is allowed to proceed, showing that embodiments are able to measure real-time or near real-time production of breakdown products from β-O-4.

Systems Using Coupled Lignin-Modifying Enzymes

Many embodiments are directed to systems coupling lignin-modifying enzymes. FIG. 8 further shows the activities of embodiments that couple multiple enzymes to breakdown the model lignin dimer, β-O-4. In particular, FIG. 8 illustrates how certain embodiments will couple multiple enzymes to breakdown lignin without having to supplement media with resources, such as a peroxide. FIG. 8 shows a peroxide-generating reaction 804 catalyzed by a coupled oxidase to generate hydrogen peroxide for use in the lignin breakdown reaction 802. In many embodiments, the peroxide-generating reaction 804 uses a sugar oxidase enzyme to oxidize a sugar molecule, such as glucose, to produce hydrogen peroxide, while other embodiments will use a benzyl alcohol oxidase to generate the hydrogen peroxide from a benzyl alcohol.

Figure 9A:
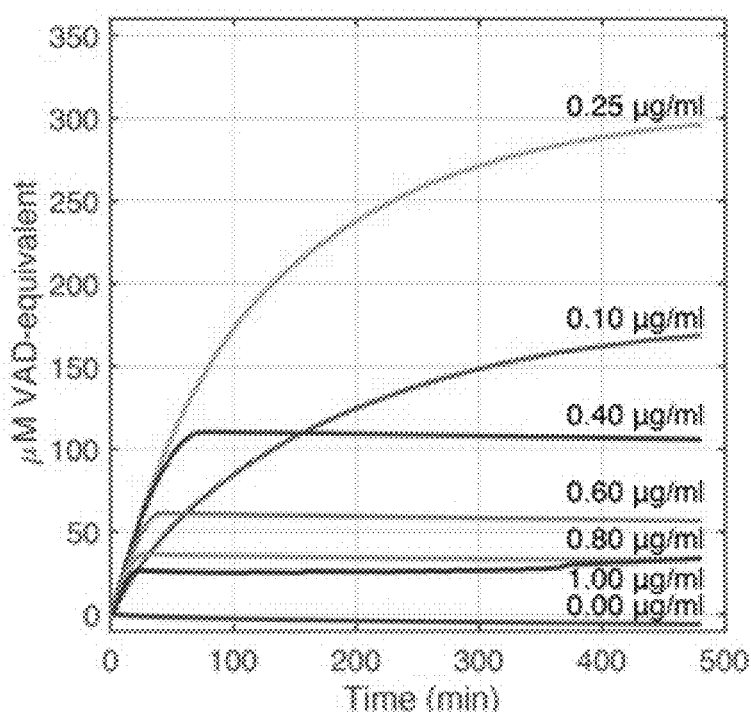
FIGS. 9A-9F illustrate enzyme kinetics and activity of coupled enzymes against a model lignin dimer, β-O-4, in accordance with various embodiments.
Figure 9B:
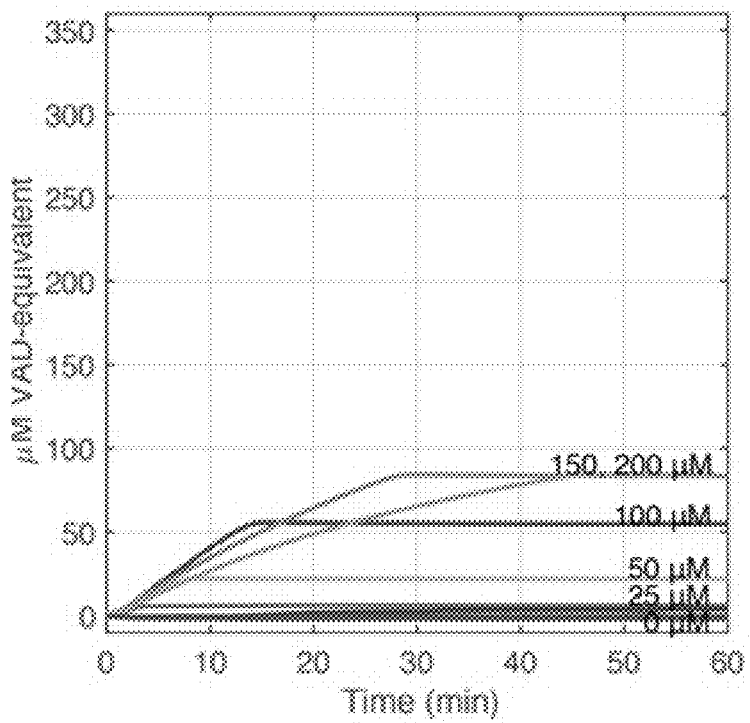
Figure 9C:
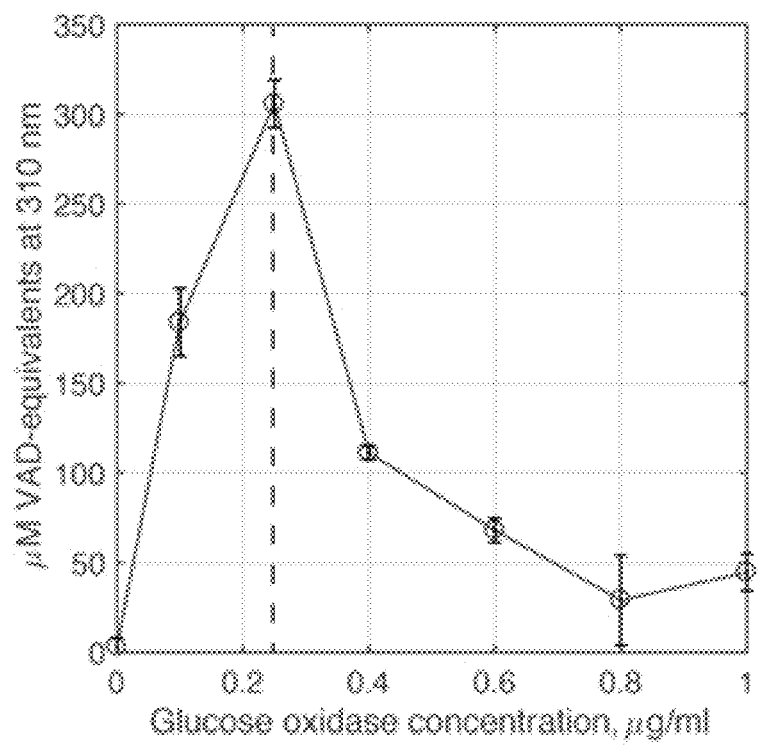
Figure 9D:
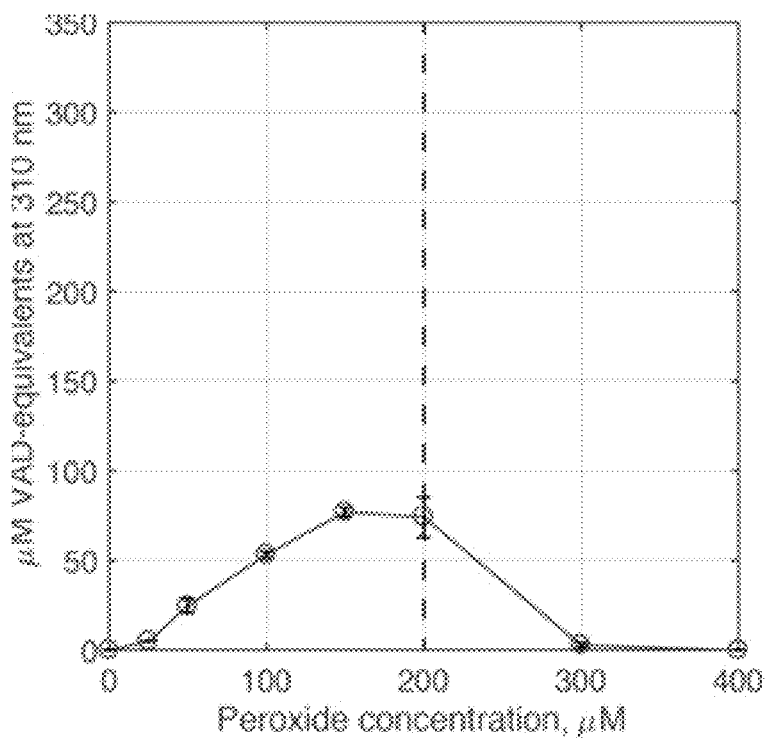
Figure 9E:
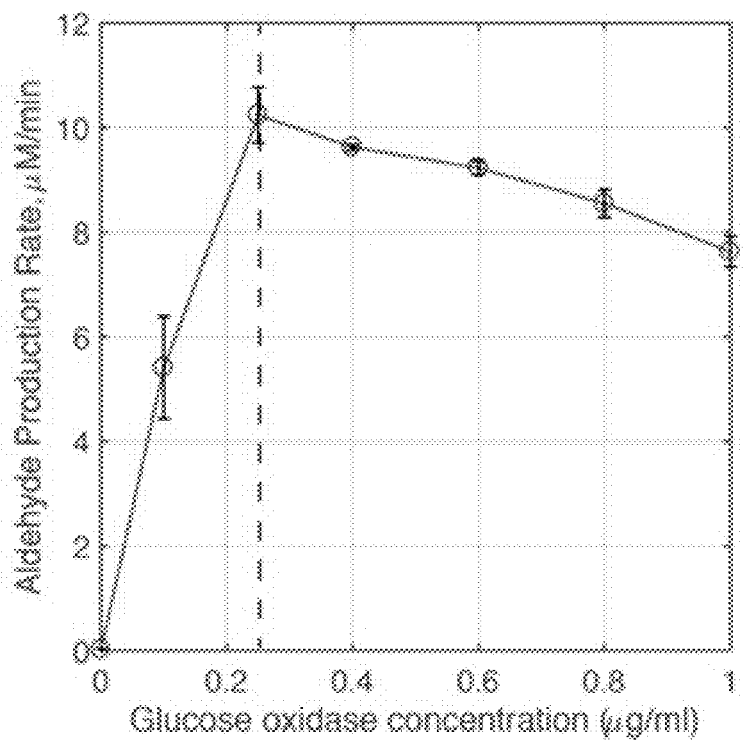
Figure 9F:
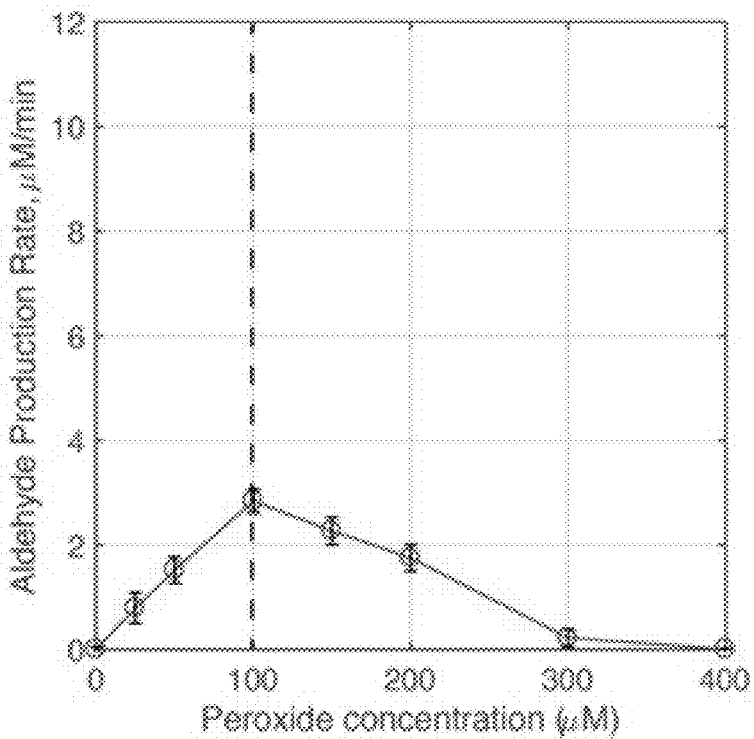

Turning to FIGS. 9A-9F, a number of embodiments will optimize the concentration of the hydrogen peroxide generating enzyme (e.g., a sugar oxidase or benzyl alcohol oxidase) to maximize the activity of the coupled peroxidase. In particular FIG. 9A illustrates the reaction kinetics of a versatile peroxidase of some embodiments coupled with various concentrations of a glucose oxidase, while FIG. 9B illustrates the kinetics of a versatile peroxidase of certain embodiments at various levels of hydrogen peroxide concentrations. Additionally, FIGS. 9C-9D illustrates maximal substrate conversion as a function of glucose oxidase concentration (FIG. 9C) and hydrogen peroxide concentration (FIG. 9D) in a variety of embodiments. Further, FIGS. 9E-9F illustrate substrate oxidation rate as a function of glucose oxidase concentration (FIG. 9E) and hydrogen peroxide concentration (FIG. 9F) in a number of embodiments.

The systems and methods described herein can be scaled up in a straightforward manner, as, in many embodiments, expression is reliable between batches, and larger numbers of plants can be used to obtain greater amounts of enzymes.

Furthermore, in a variety of embodiments, the fungal lignin-modifying enzymes produced by *N. benthamiana* have a single, well-defined glycosylation form.

Exemplary Embodiments

Although the following embodiments provide details on certain embodiments of the inventions, it should be understood that these are only exemplary in nature, and are not intended to limit the scope of the invention.

EXAMPLE 1

Expressing Lignin-Modifying Enzymes in *S. cerevisiae*

Background: Eukaryotic expression of genes can be advantageous due to proper protein folding.

Methods: *S. cerevisiae* strain JHY693 was used as the background strain for all yeast protein expression. Genes for lignin-modifying enzymes were synthesized de novo from previously-published or otherwise inferred DNA sequences coding for the mature enzymes, codon-optimized for expression in *S. cerevisiae*. For single-copy expression vectors, a pRS415-based cassette was used, with transcription driven by the ADH2 promoter, while for multi-copy expression vectors, the 2p cassette pCHINT2AL was used. Yeast transformation was carried out using the Frozen-EZ Yeast Transformation II Kit (Zymo Research). Transformant selection was performed using SD-leu plates. Single colonies were picked into 0.5 mL SD-leu media in a 96-well culture plate and incubated overnight with orbital shaking (400 rpm, 30° C.). After centrifugation (600xg, 10 min), the supernatant was removed, and the cell pellets resuspended in supplemented YPEG media (2% ethanol, 3% glycerol, 0.01 mM hemin, 70 mM potassium phosphate pH 6.0, 1 mM $CaCl_2$) and incubated for 48 hours with orbital shaking (400 rpm, 20° C.). After centrifugation (600xg, 10 min), the culture supernatant was used for subsequent activity assays at 10% v/v.

*Agrobacterium*-mediated transient expression was performed as described in previous studies, including incubating transformed *Agrobacterium* for 2 days at 30° C. (See Lau and Sattely; Six enzymes from mayapple that complete the biosynthetic pathway to the etoposide aglycone; Science. 2015 Sep 11;349(6253):1224-8; the disclosure of which is incorporated by reference in its entirety.) *Agrobacterium* colonies were collected and washed once with 0.75 mL LB medium, and resuspended in 0.5 mL *Agrobacterium* induction buffer (10 mM sodium succinate, pH 5.6, 10 mM magnesium chloride, 0.15 mM acetosyringone) and incubated for 4 to 6 hours statically at room temperature. The induced *Agrobacterium* is then diluted to an optical density at 600 nm of 0.3 per 1 ml in induction buffer. Using needleless plastic syringes, this *Agrobacterium* dilution is infiltrated into the three youngest leaves of a 5- to 7-week-old *N. benthamiana* plant. Following established methods, the transformed plants are maintained under a 16-hour light cycle at room temperature.

The signal peptide of the dirigent protein of *Sinopodophyllum hexandrum* (SEQ ID NO: 78) was used to direct protein export to the apoplast. Four days post-infiltration, apoplastic contents were extracted as previously described. (See O'Leary, et al., The Infiltration-centrifugation Technique for Extraction of Apoplastic Fluid from Plant Leaves Using Phaseolus vulgaris as an Example, www.jove.com/video/52113/the-infiltration-centrifugation-technique-for-extraction-apoplastic; the disclosure of which is incorporated herein by reference in its entirety.) Briefly, leaves were detached and submerged in 0.1 M sodium acetate, 0.3 M NaCl, pH 5.5 in a vacuum flask. It was observed that MES buffer has an inhibitory effect on peroxidase activity so sodium acetate was used instead.

Leaves expressing different enzymes can be contained within the same flask without cross-contamination issues. Leaves were weighed down within the flask using heavier objects, such as weighing spatulas, and the flask was placed in an ice bath. The leaves were vacuum infiltrated of at least 26 inches Hg for at least 3 minutes, with a slow release (at least 5 minutes) of the vacuum after. Some embodiments vacuum infiltrated the leaves for 2 additional cycles of vacuum and slow release.

After vacuum infiltration, the leaves were removed from the flask and blotted try using paper towels. The leaves were rolled in parafilm against a 1 mL pipette tip and placed inside a plunger-less plastic 5 mL syringe. This assembly was placed inside a 15 mL Falcon tube and centrifuged at 1600xg for 10 minutes at 4° C. The extracted liquid was transferred to microcentrifuge tubes and clarified by centrifugation at 14000xg for 10 minutes at 4° C. Apoplast extracts were pooled and diafiltrated at least 500-fold using extraction buffer with 10% v/v glycerol and Amicon Ultra-4 10-kDa MWCO centrifugal filters units (EMD Millipore).

ABTS activity assays were performed using 4 mM ABTS, 100 μM $H_2O_2$, 50 mM sodium tartrate, pH 3.5. In assays for Mn-dependent oxidation, 1.0 mM $MnSO_4$ was included in the above reaction, and 50 mM sodium malonate, pH 4.5, was substituted for the tartrate buffer. ABTS oxidation kinetics were observed at 414 nm (extinction coefficient 36000 1/M 1/cm) using a Synergy HTX plate reader at 25° C. Veratryl alcohol activity was measured as the production of veratraldehyde at 310 nm (extinction coefficient 9300 1/M 1/cm [Tien and Kirk]) using 20 mM veratryl alcohol, 100 μM $H_2O_2$, 50 mM sodium tartrate, pH 3.5, at 25° C. Manganese-dependent activity was measured by Mn(III)-malonate complex formation using 1.0 mM $MnSO_4$ and 100 μM $H_2O_2$ in 50 mM sodium malonate (270 nm, 11590 1/M 1/cm) at 25° C. Cellobiose dehydrogenase activity was measured at 522 nm using 10% w/v cellobiose, 0.3 mM dichloroindophenol, and 50 mM sodium tartrate, pH 5.0, at 25° C. Pyranose oxidase activity was measured by coupling to ABTS as above with the inclusion of 1 μg commercial horseradish peroxidase (HRP) and 2% w/v D-glucose in 50 mM sodium acetate, pH 6.0. For all assays, 1 unit of activity is defined as 1 μmol of observable product per liter per minute, and activities are calculated as the maximum observed rate during the initial phase of the enzyme assays.

In model lignin dimer LC-MS kinetic assays, all reactions contained 20 mM β-O-4 dimer and peroxidase-containing diafiltrated extract from *N. benthamiana* to 0.2 μM total heme content. Glucose oxidase assays contained 0.4% D-glucose and either 1.0 ng/μl glucose oxidase and 50 mM sodium tartrate pH 3.5, or 0.574 ng/μl glucose oxidase and 50 mM sodium malonate pH 4.5 with 1.0 mM $MnSO_4$. Glucose oxidase concentration was adjusted between the two pH conditions to keep the rate of peroxide generation constant. Aryl alcohol oxidase assays contained 10 mM benzyl alcohol, 40 U/L (HRP-coupled ABTS activity) of diafiltrated extract of PE-aao(FX9) from *N. benthamiana*, and 50 mM sodium tartrate pH 4.0. Pyranose oxidase assays contained 0.4% w/v D-glucose, 10 U/L (HRP-coupled ABTS activity) of diafiltrated supernatant of TV-pox from *S. cerevisiae*, and 50 mM sodium tartrate pH 4.0. Reactions were clarified (21000xg, 5 min) and initiated by the addition of peroxide-generating enzyme.

Model lignin dimer LC-MS kinetic assays were performed using an Agilent 6545 Q-TOF running in positive mode with a 6-minute water-acetonitrile gradient (0 min, 95% A; 0.2 min, 95% A; 3.65 min, 37.5% A; 3.66 min, 5% A; 4.11 min, 5% A; 4.15 min, 95% A; 5.18 min, 95% A; A: water +0.1% formic acid, B: acetonitrile +0.1% formic acid; flow rate 0.8 ml/min) on an Agilent RRHD EclipsePlus 95 Å C18 column (2.1×50 mm, 1.8 µm, 1200 bar). Reaction product profiles were measured every 24 minutes by 1 µl direct injection of reaction vials, which were maintained at 22° C. in the autosampler. Extracted ion counts (EIC) were obtained using the 'Find by Formula' function in Agilent MassHunter Qualitative Analysis software, using 35 ppm mass tolerance, 35, 500, and 35 ppm symmetric expansion of values for chromatogram extraction, and -electron, +H, +Na, +K, +NH$_4$, and –H$_2$O as possible charge carriers and neutral losses.

For coupled reactions (e.g., contain both a peroxidase and a peroxide generating oxidase), the reactions contained 20 mM β-O-4 dimer and 0.4% w/v D-glucose. Reactions assaying direct substrate oxidation contained 50 mM sodium tartrate, pH 3.5, and 1.0 ng/µl glucose oxidase; those assaying Mn-mediated substrate oxidation contained 50 mM sodium malonate, pH 4.5, 1 mM MnSO$_4$ and 0.574 ng/µl glucose oxidase (adjusted to keep reaction rate similar). The amounts of diafiltrated extracts of PO-vpl and PO-vp3 used in the reactions was normalized to the Mn activity of PC-mnp1 at a reaction concentration of 0.2 µM (total heme content; ~6 U/L). The amounts of diafiltrated extracts of PE-vpl2 and CS-lip1 used in the reaction were normalized to PC-mnp1 by total heme content. Diafiltrated extract of GFP-expressing *N. benthamiana* was used as a negative control at 1% v/v (total heme content ~0.07 µM) with the addition of 33.3 ng/µl commercial horseradish peroxidase in order to prevent peroxide accumulation. Reactions were clarified (21000 xg, 5 min) prior to initiation by addition of glucose oxidase or hydrogen peroxide. After 9 hours incubation at room temperature, samples were moved to the LC-MS autosampler maintained at 10° C. and analyzed by 1 µl direct injection of the reaction contents on an Agilent 6545 Q-TOF running in positive mode with a 6-minute water-acetonitrile gradient (as above) and an Agilent RRHD EclipsePlus 95 Å C18 column (2.1×50 mm, 1.8 µm, 1200 bar). EIC values were obtained as above.

Results: Even with thorough testing and optimization of promoters, ER signal peptides, and media supplements, *S. cerevisiae* was found to be ill-suited for the production of lignin-modifying enzymes. Low levels of activity towards the model, non-lignin-derived substrate ABTS were detected for few of the peroxidases tested. Activity towards lignin-related substrates veratryl alcohol and Mn(II) is undetectable, even after affinity purification. Western blotting reveals extracellular protein even where no activity is detected; the higher-than-expected molecular weight of the detected proteins suggests misprocessing and subsequent hyper-glycosylation, a common issue in yeast-based protein secretion. Furthermore, using commercially-available purified lignin peroxidase from *P. chrysosporium*, we observed that yeast metabolites competitively inhibit activity towards veratryl alcohol, and diafiltration of the yeast culture supernatant is required to regain activity towards veratryl alcohol and model lignin dimers.

For expression in *N. benthamiana*, the crude apoplastic extract of transgenic plants contained substantial levels of peroxidase activity as measured by ABTS. Activity was also observed towards veratryl alcohol and Mn(II), indicating the crude apoplastic extract could be directly applied for lignin deconstruction. This activity was further enhanced by diafiltration that eliminated enzyme lag due to competitive inhibition by plant-derived small molecules in the extract. In contrast to protein secreted by *S. cerevisiae*, Western blotting revealed a single, well-defined glycoform of each lignin-modifying enzyme, suggesting that *N. benthamiana* is well-suited for folding and processing of these enzymes.

Conclusion: The results indicate that the capacity of *S. cerevisiae* to express the selected panel of lignin-modifying enzymes is severely limited and requires substantial engineering for proper processing and increased secretion of this family of enzymes. Additionally, *N. benthamiana* is shown to be capable of producing a wide range of lignin-modifying enzymes at significant levels through a relatively straightforward expression and extraction process.

EXAMPLE 2

Coupling Peroxide-Generating Oxidase with Lignin-degrading Peroxidase

Background: Coupling a peroxide-generating enzyme with a lignin-degrading enzyme may allow for improved lignin conversion by not requiring the continuous addition of a peroxide, which can cause inactivation of the lignin-degrading enzyme.

Methods: Reactions contained 20 mM β-O-4 dimer, 50 mM sodium tartrate, pH 4.0, and 330 U/L ABTS activity of FPLC-purified PE-vp12 (SEQ ID NO: 19). Coupled reactions additionally contained 0.4% w/v D-glucose. Absorbance corresponding to the formation of dehydrodimer and veratraldehyde was measured at 310 nm using a Synergy HTX plate reader and converted to an estimate of total aldehyde produced using the molar extinction coefficient for veratraldehyde (9300 1/M 1/cm). Reactions were initiated by the addition of peroxide or glucose oxidase.

After completion, 1 µL of the reaction was injected on a 6545 Agilent UHPLC Q-TOF running in positive mode with an 8-minute water-acetonitrile gradient (0 min, 95% A; 0.2 min, 95% A; 5.65 min, 37.5% A; 5.66 min, 5% A; 6.11 min, 5% A; 6.15 min, 95% A; 7.18 min, 95% A; A: water +0.1% formic acid, B: acetonitrile +0.1% formic acid; flow rate 0.8 ml/min) on an Agilent RRHD EclipsePlus 95 Å C18 column (2.1×50 mm, 1.8 µm, 1200 bar).

Results: Coupling successfully overcame the limit on conversion in the case of direct peroxide addition, where increasing peroxide concentration did not result in additional product formation due to peroxidase inactivation (FIGS. 9B & 9D). An optimum glucose oxidase concentration was identified, below which the rate of the coupled reaction limited dimer conversion within the lifetime of glucose oxidase, and beyond which peroxide was generated in excess and resulted in peroxidase inactivation as evidenced by rapid loss of activity (FIGS. 9A & 9C). This maximum concentration could be extended through addition of catalase as well as increasing the concentration of peroxidase to accelerate the rate of reaction to enable greater conversion within the lifetime of glucose oxidase.

Conclusion: Coupling a peroxide-generating oxidase with a lignin-degrading peroxidase is more effective than spiking a reaction with exogenous peroxide. Additionally, this coupling can likely be used to scale the reaction for higher levels of lignin-degradation.

Doctrine of Equivalents

Although specific methods of producing lignin-modifying enzymes are discussed above, many production methods can be used in accordance with many different embodiments of the invention, including, but not limited to, methods that use other plant hosts, other bacterium, and/or any other modification as appropriate to the requirements of specific applications of embodiments of the invention. It is therefore to be understood that the present invention may be practiced in ways other than specifically described, without departing from the scope and spirit of the present invention. Thus, embodiments of the present invention should be considered in all respects as illustrative and not restrictive. Accordingly, the scope of the invention should be determined not by the embodiments illustrated, but by the appended claims and their equivalents.

What is claimed is:

1. A method to produce lignin-degrading enzymes comprising:
   obtaining an expression vector comprised of DNA and encoding a lignin-degrading peroxidase, a signal peptide to export the lignin-degrading peroxidase to an apoplast, and a constitutive promoter to drive transcription of the lignin-degrading peroxidase and the signal peptide, wherein the lignin-degrading peroxidase is encoded by a sequence selected from SEQ ID NO: 1, SEQ ID NO: 49, SEQ ID NO: 69, and SEQ ID NO: 74;
   transforming a plant with the expression vector;
   allowing the plant to express the lignin-degrading peroxidase contained within the expression vector by allowing the plant to grow for up to 15 days; and
   extracting the lignin-degrading peroxidase.

2. The method of claim 1, wherein the extracting step utilizes vacuum infiltration and centrifugation to extract the lignin-degrading peroxidase.

3. The method of claim 1, further comprising quantifying the lignin-degrading peroxidase.

4. The method of claim 3, wherein the lignin-degrading peroxidase is selected from the group consisting of lignin peroxidases, versatile peroxidases, and manganese peroxidases.

5. The method of claim 1, the plant is N. benthamiana.

6. The method of claim 1, wherein the transforming step utilizes Agrobacterium transformation, particle bombardment, or electroporation.

7. The method of claim 1, wherein the extracting step utilizes ion-exchange chromatography, size-exclusion chromatography, or immunoaffinity chromatography.

8. The method of claim 3, wherein quantifying is accomplished via western blotting, ELISA, fluorescence spectroscopy, or UV-Vis spectroscopy.

9. The method of claim 1, further comprising testing the activity of the extracted lignin-degrading peroxidase.

10. The method of claim 9, wherein the testing step is accomplished by testing the activity of the extracted lignin-degrading peroxidase against a colorimetric dye.

11. The method of claim 10, wherein the colorimetric dye is 2,2'-azino-bis(3-ethylbenzothiazoline-6-sulfonic acid) (ABTS) or 2,6-Dichlorophenolindophenol (DCIP).

12. The method of claim 9, wherein the testing step is accomplished by testing the activity of the extracted lignin-degrading peroxidase against a model lignin dimer.

13. The method of claim 12, wherein the model lignin dimer is β-O-4.

14. The method of claim 1, wherein the signal peptide is encoded by a DNA sequence selected from the group consisting of SEQ ID NOs: 78-80.

15. The method of claim 1, wherein the lignin-degrading peroxidase is encoded by SEQ ID NO: 69.

16. The method of claim 1, wherein the lignin-degrading peroxidase is a versatile peroxidase.

17. The method of claim 1, wherein the constitutive promoter is a CAMV 35S promoter.

18. The method of claim 1, wherein the wherein the lignin-degrading peroxidase is encoded by SEQ ID NO: 74.

19. The method of claim 1, wherein the wherein the lignin-degrading peroxidase is encoded by SEQ ID NO: 1.

20. The method of claim 1, wherein the wherein the lignin-degrading peroxidase is encoded by SEQ ID NO: 49.

\* \* \* \* \*